United States Patent
Sung et al.

(10) Patent No.: US 8,283,317 B1
(45) Date of Patent: *Oct. 9, 2012

(54) NANOPARTICLES FOR PROTEIN DRUG DELIVERY

(75) Inventors: Hsing-Wen Sung, Hsinchu (TW); Zi-Xian Liao, Hsinchu (TW); Shu-Fen Peng, Hsinchu (TW); Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/465,793

(22) Filed: May 7, 2012

Related U.S. Application Data

(63) Continuation of application No. 13/356,583, filed on Jan. 23, 2012, now Pat. No. 8,187,570, which is a continuation-in-part of application No. 13/134,798, filed on Jun. 17, 2011, now Pat. No. 8,153,153, which is a continuation-in-part of application No. 12/931,202, filed on Jan. 26, 2011, now Pat. No. 7,993,624, which is a continuation of application No. 12/800,848, filed on May 24, 2010, now Pat. No. 7,879,313, which is a continuation-in-part of application No. 12/321,855, filed on Jan. 26, 2009, now Pat. No. 7,871,988, which is a continuation-in-part of application No. 12/286,504, filed on Sep. 30, 2008, now Pat. No. 7,604,795, which is a continuation-in-part of application No. 12/151,230, filed on May 5, 2008, now Pat. No. 7,541,046, which is a continuation-in-part of application No. 11/398,145, filed on Apr. 5, 2006, now Pat. No. 7,381,716, which is a continuation-in-part of application No. 11/284,734, filed on Nov. 21, 2005, now Pat. No. 7,282,194, which is a continuation-in-part of application No. 11/029,082, filed on Jan. 4, 2005, now Pat. No. 7,265,090.

(60) Provisional application No. 61/269,424, filed on Jun. 24, 2009.

(51) Int. Cl.
*A61K 38/00* (2006.01)

(52) U.S. Cl. ..................................... 514/12.1

(58) Field of Classification Search ................... 514/12.1
See application file for complete search history.

(56) References Cited

U.S. PATENT DOCUMENTS

| 6,649,192 B2 | 11/2003 | Fernandez et al. |
| 6,726,934 B1 | 4/2004 | Prokop |
| 2006/0051423 A1 | 3/2006 | Heppe et al. |

OTHER PUBLICATIONS

Lin YH et al. "Preparation and characterization of nanoparticles shelled with chitosan for oral insulin delivery" Biomacomolecules 2007;8:146-152.
Lin YH et al. "Novel nanoparticles for oral insulin delivery via the paracellular pathway" Nanotechnology 2007;18:1-11.
van der Lubben IM et al. "Chitosan and its derivatives in mucosal drug and vaccine delivery" Euro J Pharma Sci 2002;237:201-207.
Hosny EA et al. "Oral delivery of insulin from enteric-coated capsules containing sodium salicylate" Int J Pharmaceutics 2002;237:71-76.
Thanou M et al. "Chitosan and its derivatives as intestinal absorption enhancers" Adv Drug Deliv Rev 2001;50:S91-S201.
Smith J et al. "Effect of chitosan on epithelial cell tight junctions" Pharmaceutical Research 2004;21:43-49.
Lin YH et al. "Preparation of nanoparticles composed of chitosan/poly-gamma-glutaraldehyde and evaluation of their permeability through Caco-2 cells" Biomacromolecules 2005;6:1104-1112.
Fernandez-Urrusuno R et al. "Enhancement of nasal absorption of insulin using chitosan nanoparticles" Pharmaceutical Research 1999;16:1576-1581.
Mi FL et al. "Oral delivery of peptide drugs using nanoparticles self-assembled by poly(r-glutamic acid) and a chitosan derivative functionalized by trimethylation" Bioconjugate Chem 2008;19:1248-1255.
Minn A et al. "Drug transport into the mammalian brain: the nasal pathway and its specific metabolic barrier" J Drug Targeting 2002;10:285-296.
Vyas TK et al. "Intranasal mucoadhesive microemulsions of clonazepam: preliminary studies on brain targeting" J Pharma Sci 2006;95:570-580.
Hussar P et al. "The glucose transporter GLUT1 and the tight junction protein occludin in nasal olfactory mucosa" Chem Senses 2002;27:7-11.
Ma Z et al. "Uptake of chitosan and associated insulin in Caco-2 cell monolayers: a comparison between chitosan molecules and chitosan nanoparticles" Pharmaceutical Research 2003;20:1812-1819.

*Primary Examiner* — Maryam Monshipouri

(57) ABSTRACT

The invention discloses particulate complexes composed of chitosan, poly-glutamic acid, and at least one bioactive agent, wherein equal moles of the positively charged chitosan and the negatively charged poly-glutamic acid substrate form an electrostatic network enabling improved loading the bioactive agent.

20 Claims, 20 Drawing Sheets

Figure 2
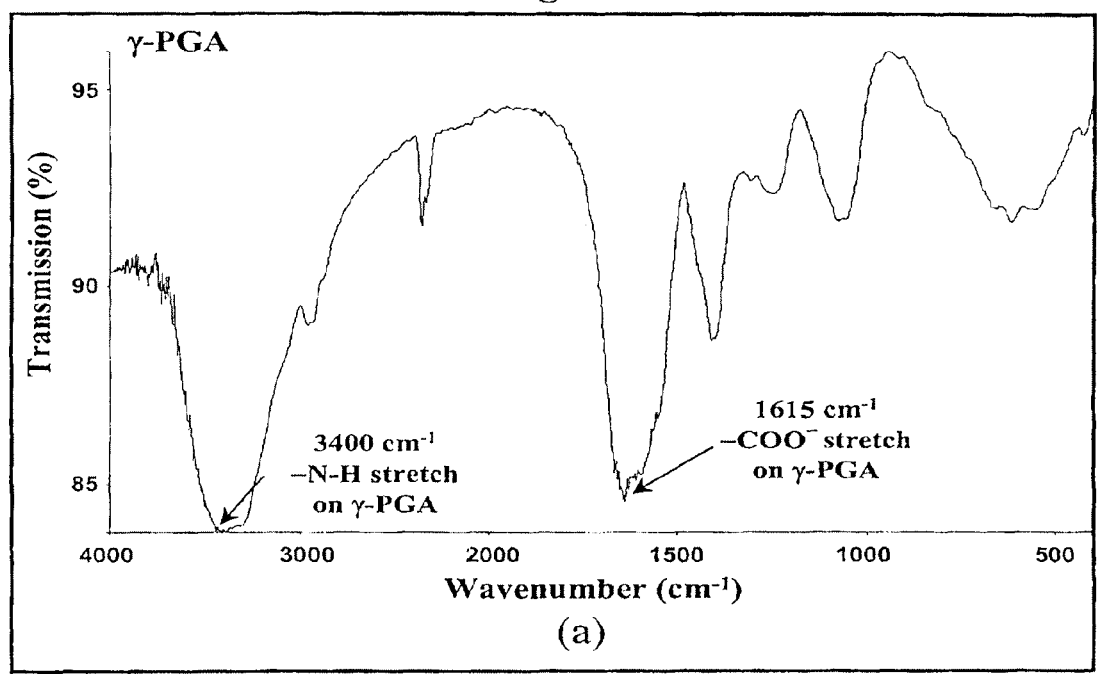
(a)
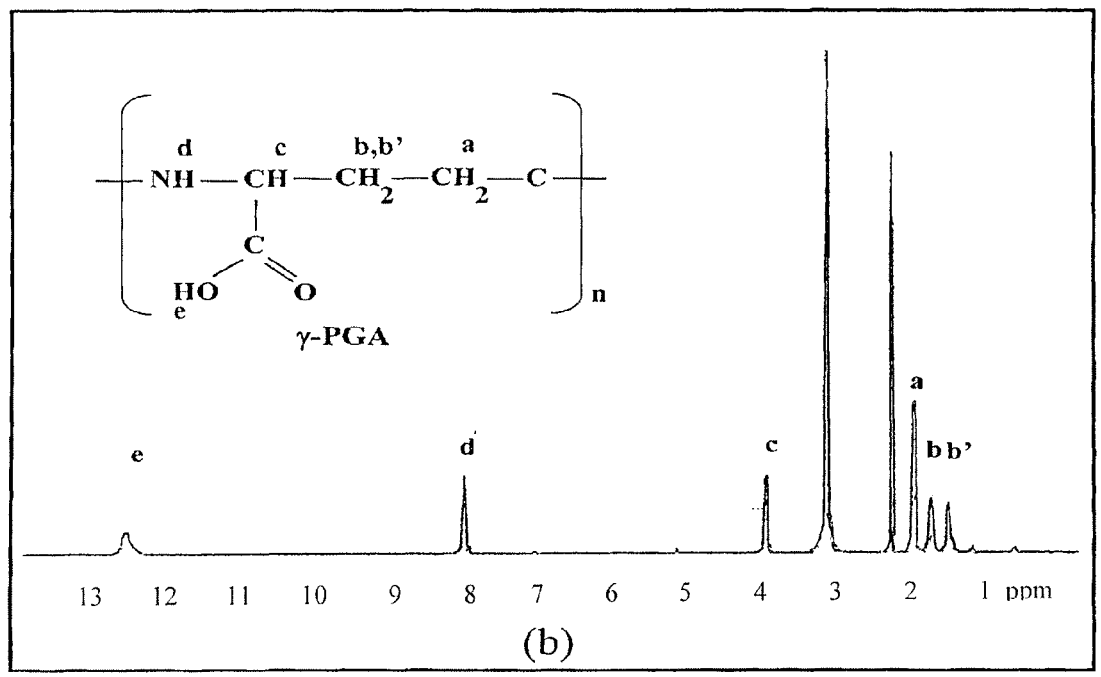
(b)

MU : mucus
EC : enterocytes
MC : M cells
LC : lymphocytes
MP : macrophages
BL : basal lamina
TJ : tight junction A. in the gastric cavity B. entering small intestine C. in the intestinal tract Figure 21. In Vivo Subcutaneous Study

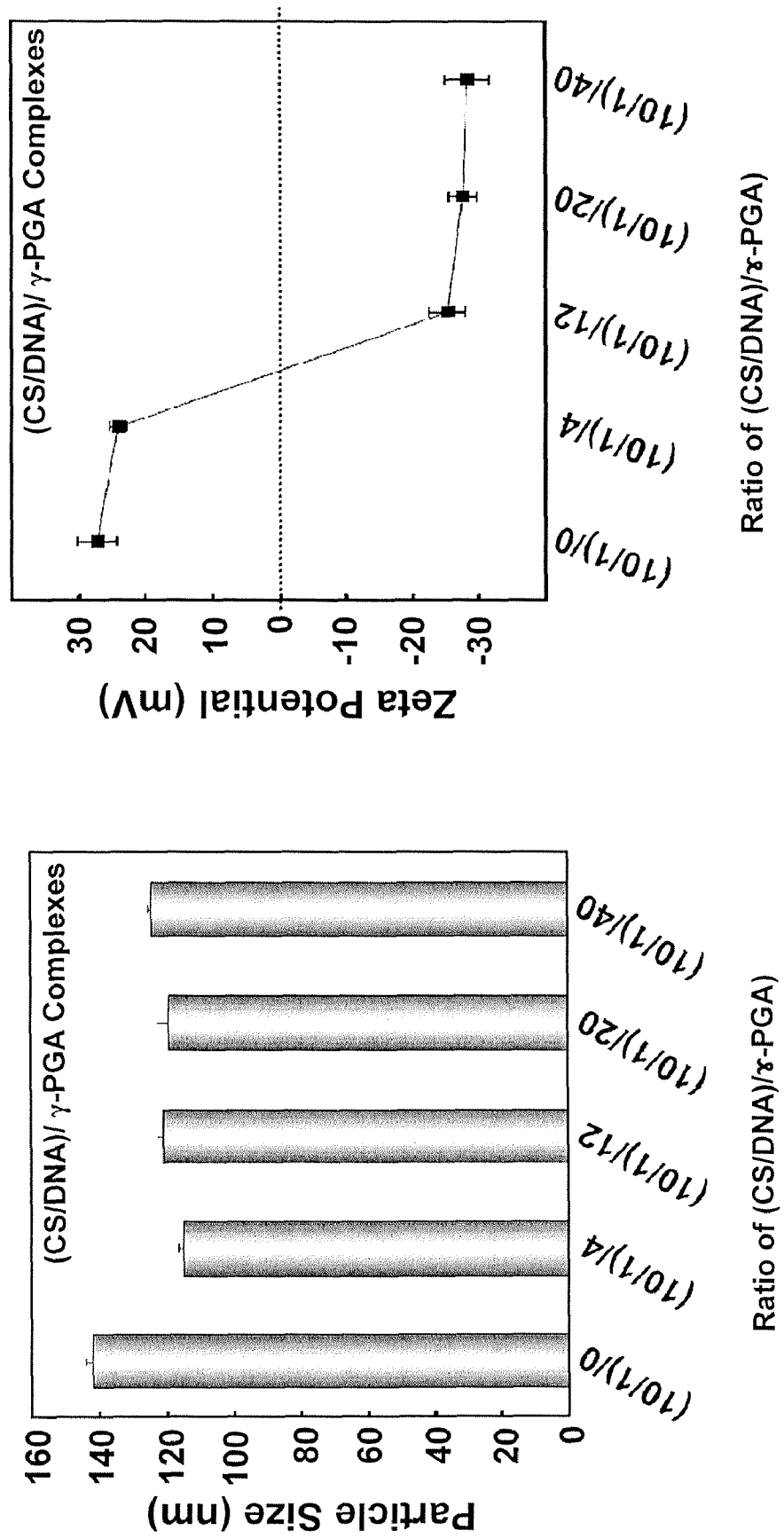
Figure 23. Particle Complex Size and Surface Zeta Potential ized with other molecules results in a release behavior that is intricately depicted to embrace multifaceted parameters. The following applied text shall serve to illustrate.

NANOPARTICLES FOR PROTEIN DRUG DELIVERY

CROSS-REFERENCE TO RELATED APPLICATIONS

This application is a continuation application of U.S. patent application Ser. No. 13/356,583, filed Jan. 23, 2012, now U.S. Pat. No. 8,187,570, which is a continuation-in-part application of U.S. patent application Ser. No. 13/134,798, filed Jun. 17, 2011, now U.S. Pat. No. 8,153,153, which is a continuation-in-part application of U.S. patent application Ser. No. 12/931,202, filed Jan. 26, 2011, now U.S. Pat. No. 7,993,624, which is a continuation application of U.S. patent application Ser. No. 12/800,848, filed May 24, 2010, now U.S. Pat. No. 7,879,313, which is a continuation-in-part application of U.S. patent application Ser. No. 12/321,855, filed Jan. 26, 2009, now U.S. Pat. No. 7,871,988, which is a continuation-in-part application of U.S. patent application Ser. No. 12/286,504, filed Sep. 30, 2008, now U.S. Pat. No. 7,604,795, which is a continuation-in-part application of U.S. patent application Ser. No. 12/151,230, filed May 5, 2008, now U.S. Pat. No. 7,541,046, which is a continuation-in-part application of U.S. patent application Ser. No. 11/398,145, filed Apr. 5, 2006, now U.S. Pat. No. 7,381,716, which is a continuation-in-part application of U.S. patent application Ser. No. 11/284,734, filed Nov. 21, 2005, now U.S. Pat. No. 7,282,194, which is a continuation-in-part application of U.S. patent application Ser. No. 11/029,082, filed Jan. 4, 2005, now U.S. Pat. No. 7,265,090, the entire contents of which are incorporated herein by reference. This application also claims the benefits of a provisional patent application Ser. No. 61/269,424, filed Jun. 24, 2009.

FIELD OF THE INVENTION

The present invention is related to medical uses of nanoparticles having a pharmaceutical composition of chitosan and polyglutamic acid with bioactive agents and delivery means of the pharmaceutical composition with enhanced permeability.

BACKGROUND OF THE INVENTION

Production of pharmaceutically active peptides and proteins in large quantities has become feasible (Biomacromolecules 2004; 5:1917-1925). The oral route is considered the most convenient way of drug administrations for patients. Nevertheless, the intestinal epithelium is a major barrier to the absorption of hydrophilic drugs such as peptides and proteins (J. Control. Release 1996; 39:131-138). This is because hydrophilic drugs cannot easily diffuse across the cells through the lipid-bilayer cell membranes. Attentions have been given to improving paracellular transport of hydrophilic drugs (J. Control. Release 1998; 51:35-46). The transport of hydrophilic molecules via the paracellular pathway is, however, severely restricted by the presence of tight junctions that are located at the luminal aspect of adjacent epithelial cells (Annu. Rev. Nutr. 1995; 15:35-55). These tight junctions form a barrier that limits the paracellular diffusion of hydrophilic molecules. The structure and function of tight junctions is described, inter alia, in Ann. Rev. Physiol. 1998; 60:121-160 and in Ballard T S et al., Annu. Rev. Nutr. 1995; 15:35-55. Tight junctions do not form a rigid barrier but play an important role in the diffusion or translocation through the intestinal epithelium from lumen to bloodstream and vice versa.

Movement of solutes between cells, through the tight junctions that bind cells together into a layer as with the epithelial cells of the gastrointestinal tract, is termed paracellular transport. Paracellular transport is passive. Paracellular transport depends on electrochemical gradients generated by transcellular transport and on solvent drag through tight junctions. Tight junctions form an intercellular barrier that separates the apical and basolateral fluid compartments of a cell layer. Movement of a solute through a tight junction from apical to basolateral compartments depends on the "tightness" of the tight junction for that solute.

Polymeric nanoparticles have been widely investigated as carriers for drug delivery (Biomaterials 2002; 23:3193-3201). Much attention has been given to the nanoparticles made of synthetic biodegradable polymers such as poly-ε-caprolactone and polylactide due to their good biocompatibility (J. Drug Delivery 2000; 7:215-232; Eur. J. Pharm. Biopharm. 1995; 41:19-25). However, these nanoparticles are not ideal carriers for hydrophilic drugs because of their hydrophobic property. Some aspects of the invention relate to a novel nanoparticle system, composed of hydrophilic chitosan and poly(glutamic acid) hydrogels that is prepared by a simple ionic-gelation method. This technique is promising as the nanoparticles are prepared under mild conditions without using harmful solvents. It is known that organic solvents may cause degradation of peptide or protein drugs that are unstable and sensitive to their environments (J. Control. Release 2001; 73:279-291).

Following the oral drug delivery route, protein drugs are readily degraded by the low pH of gastric medium in the stomach. The absorption of protein drugs following oral administration is challenging due to their high molecular weight, hydrophilicity, and susceptibility to enzymatic inactivation. Protein drugs at the intestinal epithelium could not partition into the hydrophobic membrane and thus can only traverse the epithelial barrier via the paracellular pathway. However, the tight junction forms a barrier that limits the paracellular diffusion of hydrophilic molecules.

Chitosan (CS), a cationic polysaccharide, is generally derived from chitin by alkaline deacetylation (J. Control. Release 2004; 96:285-300). It was reported from literature that CS is non-toxic and soft-tissue compatible (Biomacromolecules 2004; 5:1917-1925; Biomacromolecules 2004; 5:828-833). Additionally, it is known that CS has a special feature of adhering to the mucosal surface and transiently opening the tight junctions between epithelial cells (Pharm. Res. 1994; 11:1358-1361). Most commercially available CSs have a quite large molecular weight (MW) and need to be dissolved in an acetic acid solution at a pH value of approximately 4.0 or lower that is sometimes impractical. However, there are potential applications of CS in which a low MW would be essential. Given a low MW, the polycationic characteristic of CS can be used together with a good solubility at a pH value close to physiological ranges (Eur. J. Pharm. Biopharm. 2004; 57:101-105). Loading of peptide or protein drugs at physiological pH ranges would preserve their bioactivity. On this basis, a low-MW CS, obtained by depolymerizing a commercially available CS using cellulase, is disclosed herein to prepare nanoparticles of the present invention.

The γ-PGA, an anionic peptide, is a natural compound produced as capsular substance or as slime by members of the genus *Bacillus* (Crit. Rev. Biotechnol. 2001; 21:219-232). γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer, [poly(α-glutamic acid), α-PGA] has been used for drug delivery (Adv. Drug Deliver. Rev. 2002; 54:695-713; Cancer Res. 1998; 58:2404-2409). α-PGA is usually synthesized from poly(γ-benzyl-L-glutamate) by removing the benzyl protecting group with the use of hydrogen bromide. Hashida et al. used α-PGA as a polymeric backbone and galactose moiety as a ligand to target hepatocytes (J. Control. Release 1999; 62:253-262). Their in vivo results indicated that the galactosylated α-PGA had a remarkable targeting ability to hepatocytes and degradation of a-PGA was observed in the liver.

Thanou et al. reported chitosan and its derivatives as intestinal absorption enhancers (Adv Drug Deliv Rev 2001; 50:S91-S101). Chitosan, when protonated at an acidic pH, is able to increase the paracellular permeability of peptide drugs across mucosal epithelia. Co-administration of chitosan or trimethyl chitosan chloride with peptide drugs were found to substantially increase the bioavailability of the peptide in animals compared with administrations without the chitosan component.

Fernandez-Urrusuno et al. reported that chitosan nanoparticles enhanced the nasal absorption of insulin to a greater extent than an aqueous solution of chitosan (Pharmaceutical Research 1999; 16:1576-1581), entire contents of which are incorporated herein by reference. Insulin-loaded chitosan nanoparticles displayed a high positive charge and a rapid insulin release kinetics properties, which render them very interesting systems for nasal drug delivery.

Heppe et al. in U.S. patent application publication no. 2006/0051423 A1, entire contents of which are incorporated herein by reference, discloses a chitosan-based transport system for overcoming the blood-brain barrier. This transport system can convey active agents or markers into the brain. The transport system contains at least one substance selected from the group consisting of chitin, chitosan, chitosan oligosaccharides, glucosamine, and derivatives thereof, and optionally one or more active agents and/or one or more markers and/or one or more ligands. However, Heppe et al. neither teaches a chitosan-shelled nanoparticle transport system, nor asserts substantial efficacy of chitosan-shelled nanoparticles permeating through blood-brain barriers.

van der Lubben et al. reported that chitosan and its derivatives are effective and safe absorption enhancers to improve mucosal (nasal, peroral) delivery of hydrophilic macromolecules such as protein and peptide drugs and vaccines (Euro J Pharma Sci 2001; 14:201-207), entire contents of which are incorporated herein by reference. Interaction of the positively charged amino group at the C-2 position of chitosan with the negatively charged sites on the cell surface and tight junctions allows paracellular transport of large hydrophilic compounds by opening the tight junctions of the membrane barrier.

Minn et al. reported drug transport into the mammalian brain via the nasal pathway (J Drug Targeting 2002; 10:285-296), entire contents of which are incorporated herein by reference. The rate of entry into and distribution of drugs and other xenobiotics within the central nervous system depends on the particular anatomy of the brain microvessels forming the blood-brain barrier and of the choroids plexus forming the blood-cerebrospinal fluid barrier, which possess tight junctions preventing the passage of most polar substances.

Vyas et al. reported a preliminary study on brain targeting for intranasal mucoadhesive microemulsions of clonazepam (J Pharma Sci 2006; 95:570-580) entire contents of which are incorporated herein by reference. In the rabbit study, it shows more effective brain targeting with intranasal administration than intravenous administration. Rabbit brain scintigraphy also showed higher intranasal uptake of the drug into the brain.

Prokop et al in U.S. Pat. No. 6,383,478 teaches nanoparticles in the range of 1-1000 nm diameter for drug delivery comprising at least two or more polyanions, one or more polycation(s), one or more small cation(s), and the drug. It was disclosed that at least two polyanions (for example, alginate plus other polyanions) are required in a polymeric drug delivery vehicle to deliver protein factors.

However, none of the above prior art teach a pharmaceutical composition of novel nanoparticles in a size less than 400 nanometers for an animal subject, the nanoparticles comprising positively charged chitosan and a negatively charged substrate through the nanoparticle structure, wherein the negatively charged substrate is substantially neutralized with the positively charged chitosan to enhance loading of at least one bioactive agent that is loaded within the nanoparticles.

SUMMARY OF THE INVENTION

It is one object of the present invention to provide a novel nanoparticle system and methods of preparation for paracellular transport drug delivery using a simple and mild ionic-gelation method upon addition of, for example, a poly-γ-glutamic acid (γ-PGA) solution, into regular molecular weight chitosan solution. In one embodiment, the chitosan employed is N-trimethyl chitosan (TMC), EDTA-chitosan, mono-N-carboxymethyl chitosan (MCC), N-palmitoyl chitosan (NPCS), chitosan derivatives, or combinations thereof. In an alternate embodiment, the chitosan employed is low molecular weight chitosan (low-MW CS). In one embodiment, the molecular weight of a low-MW CS of the present invention is about 80 kDa or less, preferably at about 40 kDa, adapted for adequate solubility at a pH that maintains the bioactivity of protein and peptide drugs. It is stipulated that a chitosan particle with about 30-50 kDa molecular weight is kidney inert. The particle size and the zeta potential value of the prepared nanoparticles are controlled by their constituted compositions. The results obtained by the TEM (transmission electron microscopy) and AFM (atomic force microscopy) examinations showed that the morphology of the prepared nanoparticles was generally spherical or spheroidal in shape.

Evaluation of the prepared nanoparticles in enhancing intestinal paracellular transport was investigated in vitro in Caco-2 cell monolayers model. Some aspects of the present invention provide the nanoparticles with CS dominated on the surfaces to effectively reduce the transepithelial electrical resistance (TEER) of Caco-2 cell monolayers. The confocal laser scanning microscopy (CLSM) observations confirm that the nanoparticles or fragments thereof with CS dominating on the surface are able to open the tight junctions between Caco-2 cells and allows transport of the nanoparticles via the paracellular pathways.

Some aspects of the invention relate to a method of enhancing intestinal or blood brain paracellular transport configured for delivering at least one bioactive agent or API (active pharmaceutical ingredient) in a patient comprising administering nanoparticles composed of γ-PGA and chitosan, wherein the step of administering the nanoparticles may be via oral administration (including sublingual, buccal, cheek and the like), nasal instillation, transcutaneous injection, or injection into a blood vessel.

In one embodiment, the surface of the nanoparticles comprises about equal quantity or moles of chitosan and a negatively charged substrate so the surface potential is about neutral or zero. In another embodiment, a substantial surface of the nanoparticles is characterized with a positive surface charge or negative surface charge. In one embodiment, substantially all of the negatively charged substrate conjugates with substantially all of the positively charged chitosan so to maintain a substantially zero-charge (neutral) nanoparticle. The conjugation of the nanoparticle components enhances API loading content for the current nanoparticle system. In one embodiment, at least one bioactive, a protein drug, or a third compound is loaded within the nanoparticle system.

In a further embodiment, the nanoparticles have a mean particle size between about 50 and 400 nanometers, preferably between about 100 and 300 nanometers, and most preferably between about 100 and 200 nanometers. The bioactive nanoparticle fragments resulting from the nanoparticles of the present invention are generally in the range of about 10 to 150 nm, preferably in the range of about 20 to 100 nm, and most preferably in the range of about 20 to 50 nm.

In some embodiments, the nanoparticles are loaded with a therapeutically effective amount of at least one bioactive agent, wherein the bioactive agent is selected from the group consisting of proteins, peptides, nucleosides, nucleotides, antiviral agents, antineoplastic agents, antibiotics, and anti-inflammatory drugs. In another embodiment, the bioactive agent is associated with or entrapped within micelles before being loaded into the nanoparticle structure. In still another embodiment, the bioactive agent is lipophilic, hydrophobic, or hydrophilic. After being associated with micelles (via a physical, chemical, or a biochemical means), the lipophilic hydrophobic or hydrophilic bioactive agent becomes encapsulatable through the affinity of micelles toward the inactive ingredients of chitosan and a negative charged substrate of the nanoparticles. In one embodiment, the micelles are either oil-in-water micelles or water-in-oil micelles.

Further, the bioactive agent may be selected from the group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor, anti tumor necrosis factor, erythropoietin, and melanocyte-stimulating hormone. In one preferred embodiment, the bioactive agent is an Alzheimer antagonist for treating Alzheimer's diseases.

Some aspects of the invention relate to a dose of nanoparticles that effectively enhance intestinal or blood brain paracellular transport comprising a negatively charged component, such as γ-PGA, a-PGA, PGA-DTPA, heparin, or heparan sulfate, in the core and low molecular weight chitosan.

In a further embodiment, the nanoparticles comprise at least one bioactive agent, such as anti-diabetic compound (for example, insulin, insulin analog, GLP-1, GLP-1 analog, and the like), Alzheimer's disease antagonist, Parkison's disease antagonist, or other protein/peptide. The bioactive agent for treating Alzheimer's disease may include memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis). Examples of insulin or insulin analog products include, but not limited to, Humulin® (by Eli Lilly), Humalog® (by Eli Lilly) and Lantus® (by Aventis).

Some aspects of the invention relate to a dose of nanoparticles that effectively enhance intestinal or blood brain paracellular transport comprising a negatively charged substrate and low molecular weight chitosan, wherein the nanoparticles are crosslinked with a crosslinking agent or with light, such as ultraviolet irradiation.

Some aspects of the invention provide a dose of nanoparticles characterized by enhancing intestinal or blood brain paracellular transport, each nanoparticle comprising a first component of at least one bioactive agent, a second component of low molecular weight chitosan, and a third component that is negatively charged. In one embodiment, the third component is γ-PGA, a-PGA, derivatives or salts of PGA, PGA-DTPA, PGA-complexone conjugate, heparin or alginate. In another embodiment, the first component comprises insulin at a concentration range of 0.075 to 0.091 mg/ml, the second component at a concentration range of 0.67 to 0.83 mg/ml, and the third component comprises γ-PGA at a concentration range of 0.150 to 0.184 mg/ml.

Some aspects of the invention provide a dose of nanoparticles characterized by enhancing intestinal or blood brain paracellular transport, each nanoparticle comprising a first component of at least one bioactive agent, a second component of low molecular weight chitosan, and a third component that is negatively charged, wherein the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, insulin, and tacrine hydrochloride. In a further embodiment, the at least one bioactive agent is insulin or insulin analog. In still another embodiment, the at least one bioactive agent is selected from the group consisting of proteins, peptides, nucleosides, nucleotides, antiviral agents, antineoplastic agents, antibiotics, and anti-inflammatory drugs.

Some aspects of the invention provide a dose of nanoparticles characterized by enhancing intestinal or blood brain paracellular transport, wherein the nanoparticles are further encapsulated in a capsule for oral administration. In one embodiment, the nanoparticles are freeze-dried. In one embodiment, the interior surface of the capsule is treated to be lipophilic or hydrophobic. In another embodiment, the exterior surface of the capsules or tablets is enteric-coated.

Some aspects of the invention provide a dose of nanoparticles characterized by enhancing intestinal or blood brain paracellular transport, each nanoparticle comprising a first component of at least one bioactive agent, a second component of low molecular weight chitosan, and a third component that is negatively charged, wherein the second component is crosslinked. In one embodiment, the degree of crosslinking is less than 50%. In another embodiment, the degree of crosslinking is ranged between 1% and 20%.

Some aspects of the invention provide a dose of nanoparticles characterized by enhancing intestinal or blood brain paracellular transport, each nanoparticle comprising a first component of at least one bioactive agent, a second component of low molecular weight chitosan, and a third component that is negatively charged, wherein the second component is crosslinked with a crosslinking agent selected from the group consisting of genipin, its derivatives, analog, stereoisomers and mixtures thereof. In one embodiment, the crosslinking agent is selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers.

Some aspects of the invention provide a dose or a pharmaceutical composition of nanoparticles characterized by enhancing intestinal or blood brain paracellular transport, wherein the low molecule weight chitosan has a molecular weight of 80 kDa or less. In one embodiment, the low molecule weight chitosan is further grafted with a polymer.

Some aspects of the invention provide a method of enhancing intestinal or blood brain paracellular transport comprising administering a dose of nanoparticles, wherein each nanoparticle comprises a first component of at least one bioactive agent, a second component of low molecular weight chitosan, and a third component that is negatively charged. In one embodiment, the step of administering the dose of nanoparticles is via oral administration for enhancing intestinal paracellular transport. In another embodiment, the step of administering the dose of nanoparticles is via venous administration or injection to a blood vessel for enhancing blood brain paracellular transport or mitigating the blood-brain barrier (BBB). In a further embodiment, the step of administrating the dose of nanoparticles is via nasal instillation, buccal or oral administration (including sublingual). In a further embodiment, the step of administrating the dose of nanoparticles is via endocytosis. The nanoparticles of fragments thereof may be in a freeze-dried powder form.

Some aspects of the invention provide a method of treating diabetes of a patient comprising orally administering anti-diabetic compound (for example, insulin, insulin analog, GLP-1, GLP-1 analog, anti-diabetic drugs, and the like) containing nanoparticles with a dosage effective amount of the anti-diabetic compound to treat the diabetes, wherein at least a portion of the nanoparticles comprises positively charged chitosan and a negatively charged substrate in about the equal amount or moles. In another embodiment, the negatively charged substrate is selected from the group consisting of γ-PGA, α-PGA, water-soluble salts of PGA, metal salts of PGA, PGA-complexone conjugate, heparin, heparin analogs, low molecular weight heparin, glycosaminoglycans, and alginate. The molecular formula of the insulin is selected from the group consisting of $C_{254}H_{377}N_{65}O_{75}S_6$, $C_{257}H_{383}N_{65}O_{77}S_6$, $C_{256}H_{381}N_{65}O_{79}S_6$, $C_{267}H_{404}N_{72}O_{78}S_6$, $C_{267}H_{408}N_{72}O_{77}S_6$ (insulin glargine), $C_{267}H_{402}N_{64}O_{76}S_6$ (insulin determir), and the like.

In one embodiment, the orally administering insulin containing nanoparticles comprise a dosage effective amount of the insulin to treat the diabetes comprising an insulin amount of between about 15 international units to 45 units, preferably between about 25 units to 35 units, per kilogram body weight of the patient. In a further embodiment, the insulin-containing nanoparticle comprises a trace amount of zinc or calcium, or is treated with enteric coating. Further, the nanoparticle or particulate complexes are treated with enteric polymer.

In one embodiment, the insulin containing nanoparticles further comprise at least one absorption or permeation enhancer, wherein the enhancer may be selected from the group consisting of chelators, EDTA (ethylenediaminetetraacetic acid), bile salts, surfactants, medium-chain fatty acids, phosphate esters, and the like. In another embodiment, the nanoparticles and the enhancer are co-encapsulated in a capsule or are administrated separately.

Some aspects of the invention provide nanoparticles for oral administration in a patient, comprising positively charged chitosan, a negatively charged substrate, and a bioactive agent conjugated with the substrate, wherein the substrate is selected from the group consisting of heparin, heparin analogs, low molecular weight heparin, glycosaminoglycans, and alginate, the bioactive agent being selected from the group consisting of chondroitin sulfate, hyaluronic acid, calcitonin, vancomycin, growth factor and protein with pharmaceutically effective amount.

Some aspects of the invention provide a method of treating Alzheimer's diseases of a patient comprising intravenously administering or intramuscularly/subcutaneously injecting bioactive nanoparticles with a dosage effective to treat the Alzheimer's diseases, wherein the bioactive nanoparticles comprises positively charged chitosan, a negatively charged substrate, and at least one bioactive agent for treating Alzheimer's disease, wherein the at least one bioactive agent is selected from the group consisting of memantine hydrochloride, donepezil hydrochloride, rivastigmine tartrate, galantamine hydrochloride, and tacrine hydrochloride.

In one embodiment, the dosage effective to treat the Alzheimer's diseases comprises administering the at least one bioactive agent for treating Alzheimer's disease at about 10 mg to 40 mg per day over a period of one month to one year. In another embodiment, at least a portion the nanoparticles is crosslinked, preferably at a degree of crosslinking less than about 50%, or most preferably between about 1% and 20%.

One aspect of the invention provides a pharmaceutical composition of nanoparticles, wherein the nanoparticles may be freeze-dried to form solid dried nanoparticles. The dried nanoparticles may be loaded in a capsule or a tablet/pill for oral administration in a patient, wherein the capsule or tablet/pill may be further enterically coated. The freeze-dried nanoparticles can be rehydrated in solution or by contacting fluid so to revert to wet nanoparticles. In one embodiment, nanoparticles may be mixed with trehalose or with hexan-1,2,3,4,5,6-hexyl in a freeze-drying process. In one embodiment, the interior surface of the capsule is treated to be lipophilic or hydrophobic. In another embodiment, the exterior surface of the capsule, tablet or pill is enteric-coated.

Some aspects of the invention provide a pharmaceutical composition of nanoparticles characterized by enhancing paracellular transport, each nanoparticle comprising a shell component and a core component, wherein at least a portion of the shell component comprises chitosan and wherein the core component is comprised of $MgSO_4$, sodium tripolyphosphate, at least one bioactive agent, and a negatively charged compound, wherein a substantial portion of the negatively charged compound is conjugated to the chitosan. In one embodiment, the negatively charged component of the pharmaceutical composition is γ-PGA or a derivative or salt of PGAs.

Some aspects of the invention provide an orally deliverable capsule to an animal subject comprising: (a) an empty capsule; and (b) bioactive nanoparticles loaded within the empty capsule, wherein the nanoparticles comprise chitosan, a negatively charged substrate, and at least one bioactive agent. In one embodiment, the empty capsule comprises a two-part hard gelatin capsule. In another embodiment, the capsule is treated with an enteric coating.

One object of the present invention is to provide a method of manufacturing the orally deliverable capsule, the method comprising steps of: (a) providing an empty capsule; (b) providing bioactive nanoparticles, wherein the nanoparticles comprise chitosan, a negatively charged substrate, and at least one bioactive agent; (c) freeze-drying the nanoparticles; and (d) filling the freeze-dried bioactive nanoparticles into the empty capsule, thereby producing an orally deliverable capsule. In one embodiment, the bioactive nanoparticles further comprise magnesium sulfate and TPP.

Some aspects of the invention provide a pharmaceutical composition of nanoparticles for oral administration in a patient, the nanoparticles comprising positively charged chitosan, a negatively charged substrate, wherein the negatively charged substrate is at least partially or substantially totally neutralized with the positively charged chitosan, and at least one bioactive agent loaded within the nanoparticles. In one embodiment, the bioactive agent is a non-insulin exenatide, a non-insulin pramlintide, insulin, insulin analog, or combinations thereof. In one embodiment, the nanoparticles are formed via a simple and mild ionic-gelation method.

In one embodiment of the pharmaceutical composition of the present invention, the substrate is PGA, wherein the PGA may be γ-PGA, α-PGA, PGA derivatives, PGA-DTPA, PGA-complexone conjugates, or salts of PGA. In one embodiment of the pharmaceutical composition of the present invention, the substrate is heparin, wherein the heparin is a low molecular weight heparin.

In one embodiment, a surface of the nanoparticles of the pharmaceutical composition of the present invention is characterized with a positive surface charge, wherein the nanoparticles have a surface charge from about +15 mV to about +50 mV. In another embodiment, the nanoparticles have a mean particle size between about 50 and 400 nanometers. In still another embodiment, at least a portion of the shell portion of the nanoparticles is crosslinked. In a further embodiment, the nanoparticles are in a form of freeze-dried powder. In one embodiment, the nanoparticles of the pharmaceutical composition of the present invention further comprise magnesium sulfate and TPP.

Some aspects of the invention provide a method of delivering a bioactive agent to blood circulation in a patient, comprising: (a) providing nanoparticles according to the pharmaceutical composition of the present invention, wherein the nanoparticles are formed via a simple and mild ionic-gelation method; (b) administering the nanoparticles orally toward the intestine of the patient; (c) urging the nanoparticles to be absorbed onto a surface of an epithelial membrane of the intestine; (d) permeating bioactive agent to pass through an epithelial barrier of the intestine; and (e) releasing the bioactive agent into the blood circulation. In one embodiment, the bioactive agent is selected from the group consisting of exenatide, pramlintide, insulin, insulin analog, and combinations thereof.

Some aspects of the invention provide a nanoparticle delivery system for enhancing the paracellular permeation of at least one bioactive agent, comprising nanoparticles or fragments thereof, the nanoparticles comprising a shell portion that is dominated by positively charged chitosan, a core portion that contains negatively charged substrate, wherein the negatively charged substrate is at least partially reacted with a portion of the positively charged chitosan in the core portion, and the at least one bioactive agent loaded within the nanoparticles, wherein the substrate is PGA or heparin.

In one embodiment, the PGA of the nanoparticle delivery system is γ-PGA, α-PGA, derivatives of PGA or salts of PGA. In another embodiment, a surface of the nanoparticles of the nanoparticle delivery system is characterized with a positive surface charge or zero surface charge. In a further embodiment, the nanoparticles of the nanoparticle delivery system are formed via a simple and mild ionic-gelation method.

In one embodiment, the bioactive agent is insulin or insulin analog. In another embodiment, the bioactive agent is selected from the group consisting of anti-inflammatory drugs, anti-epileptic drugs, Alzheimer's antagonist, anti-HIV drugs, anti-oxidants, anti-neuromyelitis optica drugs, meningitis antagonist, and anti-multiple sclerosis drugs.

Some aspects of the invention provide a method for treating disorders of a tight junction comprising delivering a nanoparticle delivery system to the tight junction, wherein the nanoparticle delivery system comprises nanoparticles or fragments thereof according to a pharmaceutical composition disclosed. In one embodiment, the bioactive agent is selected from the group consisting of anti-epileptic drugs, anti-inflammatory drugs, meningitis antagonist, and anti-oxidant. Some aspects of the invention provide a method of delivering a bioactive agent through a carrier of bioactive nanoparticles of fragments thereof to a brain via intranasal, buccal, sublingual, intravenous, or blood vessel route.

Some aspects of the invention provide a pharmaceutical composition of nanoparticles, the nanoparticles comprising positively charged chitosan, a negatively charged substrate, wherein the negatively charged substrate is at least partially or substantially totally neutralized with the positively charged chitosan, and micelles, wherein at least one bioactive agent is loaded within the micelles. In one embodiment, the substrate is PGA-complexone conjugate. In another embodiment, the micelles are made via an emulsion process, an oil-in-water microemulsion process or self-emulsifying process. In still another embodiment, the at least one bioactive agent is a lipophilic or hydrophobic bioactive agent.

Some aspects of the invention provide a pharmaceutical composition of nanoparticles, the nanoparticles consisting of positively charged chitosan, a negatively charged substrate, optionally a zero-charge compound, and at least one active pharmaceutical ingredient (API) or bioactive agent, wherein the nanoparticles have a mean particle size between about 50 and 400 nanometers. In one embodiment, the chitosan is N-trimethyl chitosan, mono-N-carboxymethyl chitosan (MCC), N-palmitoyl chitosan (NPCS), EDTA-chitosan, low molecular weight chitosan, chitosan derivatives, or combinations thereof. In another embodiment, the negatively charged substrate is selected from the group consisting of γ-PGA, α-PGA, water-soluble salts of PGA, metal salts of PGA, glycosaminoglycans, and a PGA-complexone conjugate.

Some aspects of the invention provide a pharmaceutical composition of nanoparticles consisting of positively charged chitosan, a negatively charged substrate, optionally a zero-charge compound, and at least an active pharmaceutical agent (API) or bioactive agent, wherein the nanoparticles are formulated into a tablet or pill configuration and wherein the tablet or pill is treated with an enteric coating. In one embodiment, the nanoparticles are encapsulated in a capsule, wherein optionally the capsule further comprises a pharmaceutically acceptable carrier, diluent, excipient, a solubilizer, bubbling agent, or emulsifier. In another embodiment, the capsule is treated with an enteric coating, or the capsule further comprises at least one permeation or absorption enhancer. In a further embodiment, the nanoparticles are freeze-dried, thereby the nanoparticles being in a powder form. In one embodiment, the zero-charge compound in the nanoparticles is a permeation or absorption enhancer.

Some aspects of the invention provide a pharmaceutical composition of nanoparticles consisting of positively charged chitosan, a negatively charged substrate, optionally a zero-charge compound, and at least an active pharmaceutical agent (API) or bioactive agent, wherein the at least one API is an anti-diabetic compound, heparin or low molecular weight heparin, or an anti-hemophilic factor.

Some aspects of the invention provide a pharmaceutical composition of nanoparticles consisting of positively charged chitosan, a negatively charged substrate, optionally a zero-charge compound, and at least an active pharmaceutical agent (API) or bioactive agent, wherein the negatively charged substrate is heparin or low molecular weight heparin.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

FIG. 2 shows (a) FT-IR and (b) $^1$H-NMR spectra of the purified γ-PGA obtained from microbial fermentation.

FIG. 23 shows particle complexes (CS/DNA/γ-PGA) size and surface zeta potential.

DETAILED DESCRIPTION OF THE EXEMPLARY EMBODIMENTS

Figure 1:
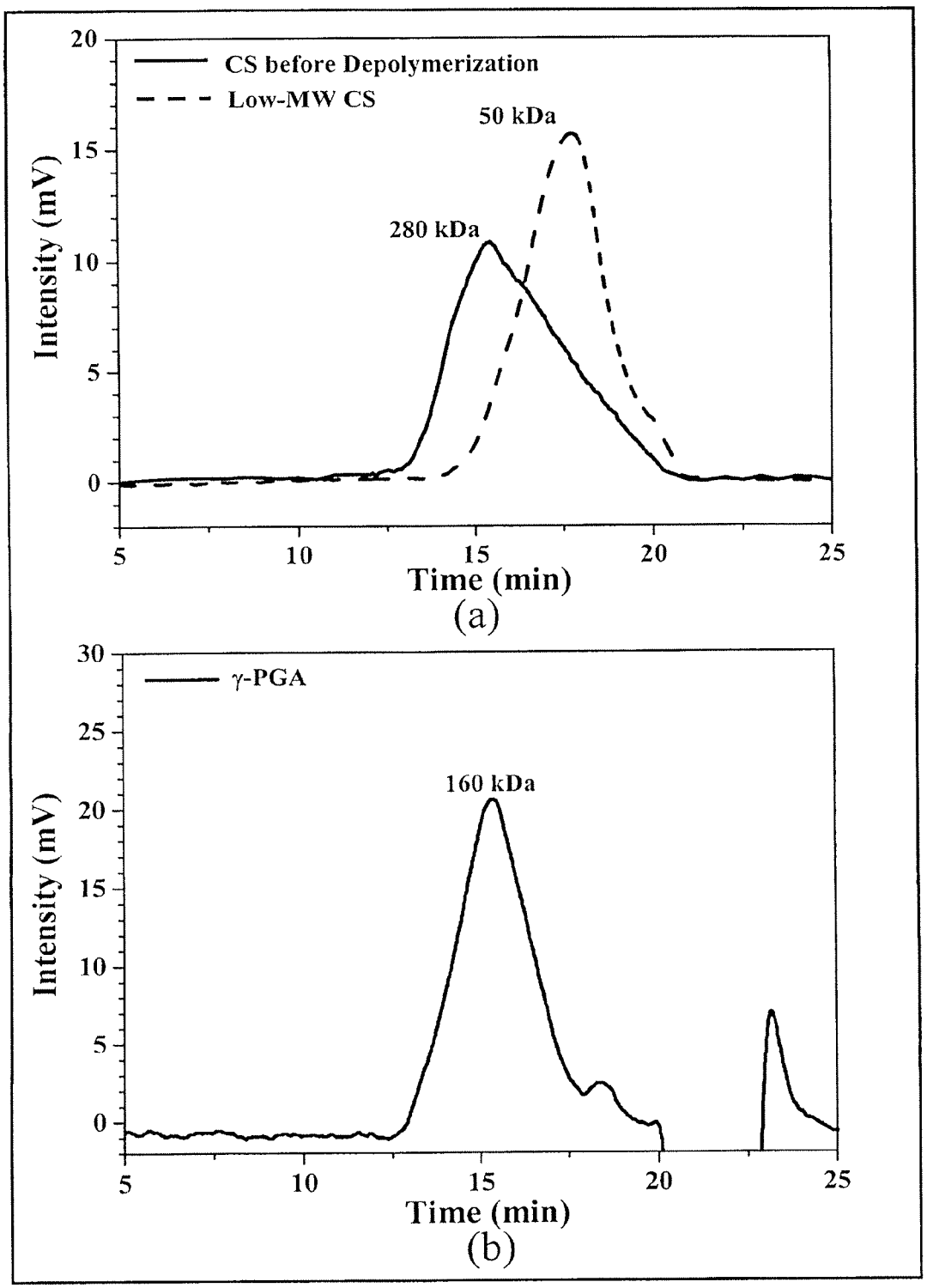
FIG. 1 shows GPC chromatograms of (a) standard-MW CS before depolymerization and the low-MW CS after depolymerization; and (b) the purified γ-PGA obtained from microbial fermentation.

The preferred embodiments of the present invention described below relate particularly to preparation of nanoparticles composed of chitosan/poly-glutamic acid/insulin and their permeability to enhance the intestinal or blood brain paracellular permeation by opening the tight junctions between epithelial cells. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

γ-PGA is a naturally occurring anionic homo-polyamide that is made of L-glutamic acid units connected by amide linkages between α-amino and γ-carboxylic acid groups. It is an exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

Example No. 1

Materials and Methods of Nanoparticles Preparation

CS (MW ~$2.8\times10^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HESS) were purchased from Sigma Chemical Co. (St. Louis, Mo.). Ethanol absolute anhydrous and potassium sodium tartrate were obtained from Merck (Darmstadt, Germany). Nonessential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

Example No. 2

Depolymerization of CS by Enzymatic Hydrolysis

Regular CS was treated with enzyme (cellulase) to produce low-MW CS according to a method described by Qin et al. with some modifications (Food Chem. 2004; 84:107-115). A solution of CS (20 WI) was prepared by dissolving CS in 2% acetic acid. Care was taken to ensure total solubility of CS. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water. The resulting low-MW CS was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μM, 50×7.5 mm and two MIXED 8 μm, 300×7.5 mm, PL Laboratories, UK) and a refractive index (RI) detector (RI2000-F, SFD, Torrance, Calif.). Polysaccharide standards (molecular weights range from 180 to 788,000, Polymer Laboratories, UK) were used to construct a calibration curve. The mobile phase contained 0.01M $NaH_2PO_4$ and 0.5M $NaNO_3$ and was brought to a pH of 2.0. The flow rate of mobile phase was 1.0 ml/min, and the columns and the RI detector cell were maintained at 30° C.

Factors limiting applications of most commercially available CSs are their high molecular weight and thus high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004; 57:101-105). Low-MW CS was used as a non-viral gene delivery system and showed promising results.

FIG. 1a shows GPC chromatograms of both standard-MW (also known as regular-MW) and low-MW CS. It is known that cellulase catalyzes the cleavage of the glycosidic linkage in CS. The low-MW CS used in the study was obtained by precipitating the depolymerized CS solution with aqueous NaOH at pH 7.0-7.2. Thus, obtained low-MW CS had a MW of about 50 kDa (FIG. 1a). In a preferred embodiment, the low molecular weight chitosan has a molecular weight of less than about 40 kDa, but above 10 kDa. Other forms of chitosan may also be applicable, including chitin, chitosan oligosaccharides, and derivatives thereof.

It was observed that the obtained low-MW CS can be readily dissolved in an aqueous solution at pH 6.0, while that before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS (before depolymerization), due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29+0.02 cp) formed nanoparticles with a mean particle size of 218.1±4.1 nm with a polydispersity index of 0.3 (n=5).

Example No. 3

Production and Purification of γ-PGA

γ-PGA was produced by *Bacillus licheniformis* (ATCC 9945, Bioresources Collection and Research Center, Hsinchu, Taiwan) as per a method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (ingredients comprising L-glutamic acid, 20.0 g/l; citric acid, 12.0 g/l; glycerol, 80.0 g/l; $NH_4Cl$, 7.0 g/l; $K_2-IPO_4$, 0.5 g/l; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times.

Subsequently, young mucoid colonies were transferred into 10 ml E medium and grown at 37° C. in a shaking incubator at 250 rpm for 24 hours. Afterward, 500 µl of culture broth was mixed with 50 ml E medium and was transferred into a 2.5-l jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and/or 2M HCl. The dissolved oxygen concentration was initially controlled at 40% of air saturation by supplying air and by controlling the agitation speed up to 1000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in deionized water to remove insoluble impurities by centrifugation for 20 minutes at 24,000×g at 4° C. The aqueous γ-PGA solution was desalted by dialysis (MWCO: 100,000, Spectrum Laboratories, Inc., Laguna Hills, Calif.) against distilled water for 12 hours with water exchanges several times, and finally was lyophilized to obtain pure γ-PGA.

The purified γ-PGA was verified by the proton nuclear magnetic resonance ($^1$H-NMR) and the FT-IR analyses. Analysis of $^1$H-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX 1 FT-IR System, Buckinghamshire, England). The samples were scanned from 400-4000 $cm^{-1}$. The average molecular weight of the purified γ-PGA was determined by the same GPC system as described before. Polyethylene glycol (molecular weights of 106-22,000) and polyethylene oxide (molecular weights of 20,000-1,000,000, PL Laboratories) standards were used to construct a calibration curve. The mobile phase contained 0.01M $NaH_2PO_4$ and 0.2M $NaNO_3$ and was brought to a pH of 7.0.

The purified γ-PGA obtained from fermentation was analyzed by GPC, $^1$H-NMR, and FT-IR. As analyzed by GPC (FIG. 1b), the purified γ-PGA had a MW of about 160 kDa. In the FT-IR spectrum (FIG. 2a), a characteristic peak at 1615 $cm^{-1}$ for the associated carboxylic acid salt (—$COO^-$ antisymmetric stretch) on γ-PGA was observed. The characteristic absorption due to C=O in secondary amides (amide I band) was overlapped by the characteristic peak of —$COO^-$. Additionally, the characteristic peak observed at 3400 $cm^{-1}$ was the N—H stretch of γ-PGA. In the $^1$H-NMR spectrum (FIG. 2b), six chief signals were observed at 1.73 and 1.94 ppm (β-$CH_2$), 2.19 ppm (γ-$CH_2$), 4.14 ppm (α-CH), 8.15 ppm (amide), and 12.58 ppm (COON). These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure.

Example No. 4

Preparation of the CS-γ-PGA Nanoparticles

Nanoparticles were obtained upon addition of γ-PGA aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. FT-IR was used to analyze peak variations of amino groups of low-MW CS and carboxylic acid salts of γ-PGA in the CS-γ-PGA nanoparticles.

Figure 3:
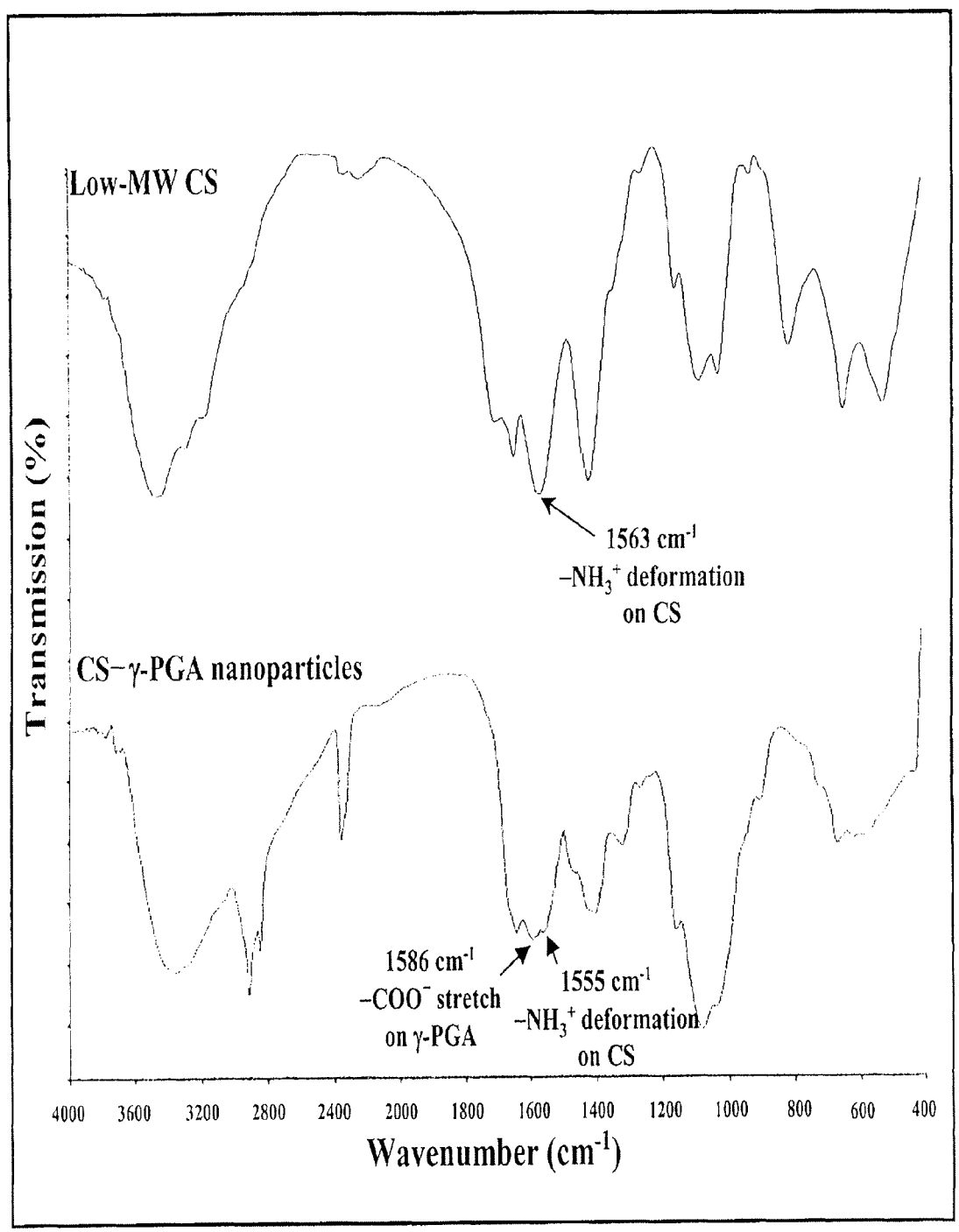
FIG. 3 shows FT-IR spectra of the low-MW CS and the prepared CS-γ-PGA nanoparticles.

As stated, nanoparticles were obtained instantaneously upon addition of a γ-PGA aqueous solution (pH 7.4) into a low-MW CS aqueous solution (pH 6.0) under magnetic stirring at room temperature. FIG. 3 shows the FT-IR spectra of the low-MW CS and the CS-γ-PGA nanoparticles. As shown in the spectrum of CS, the characteristic peak observed at 1563 cm$^{-1}$ was the protonated amino group (—NH$_3^+$ deformation) on CS. In the spectrum of CS-γ-PGA complex, the characteristic peak at 1615 cm$^{-1}$ for —COO$^-$ on γ-PGA disappeared and a new peak at 1586 cm$^{-1}$ appeared, while the characteristic peak of —NH$_3^+$ deformation on CS at 1563 cm$^{-1}$ shifted to 1555 cm$^{-1}$. These observations are attributed to the electrostatic interaction between the negatively charged carboxylic acid salts (—COO$^-$) on γ-PGA and the positively charged amino groups (—NH$_3^+$) on CS. The electrostatic interaction between the two polyelectrolytes (γ-PGA and CS) instantaneously induced the formation of long hydrophobic segments at least segments with a high density of neutral ion-pairs), and thus resulted in highly neutralized complexes that segregated into colloidal nanoparticles.

Example No. 5

Characterization of the CS-γ-PGA Nanoparticles

The morphological examination of the CS-γ-PGA nanoparticles was performed by TEM (transmission electron microscopy) and AFM (atomic force microscopy). The TEM sample was prepared by placing a drop of the nanoparticle solution onto a 400 mesh copper grid coated with carbon. About 2 minutes after deposition, the grid was tapped with a filter paper to remove surface water and positively stained by using an alkaline bismuth solution. The AFM sample was prepared by casting a drop of the nanoparticle solution on a slide glass and then dried in vacuum. The size distribution and zeta potential of the prepared nanoparticles were measured using a Zetasizer (3000HS, Malvern Instruments Ltd., Worcestershire, UK).

During storage, aggregation of nanoparticles may occur and thus leads to losing their structural integrity or forming precipitation of nanoparticles. Therefore, the stability of nanoparticles during storage must be evaluated. In the stability study, the prepared nanoparticles suspended in deionized water (1 mg/ml) were stored at 4° C. and their particle sizes and zeta potential values were monitored by the same Zetasizer as mentioned earlier during storage.

In the preparation of nanoparticles, samples were visually analyzed and three distinct solution systems were identified: clear solution, opalescent suspension, and solution with precipitation of aggregates. Examined by the Zetasizer, nanoparticles were found in the clear solution and the opalescent suspension rather than in the solution with precipitation of aggregates.

The particle sizes and the zeta potential values of CS-γ-PGA nanoparticles, prepared at varying concentrations of γ-PGA and CS, were determined and the results are shown in Tables 1a and 1b. It was found that the particle size and the zeta potential value of the prepared nanoparticles were mainly determined by the relative amount of the local concentration of γ-PGA in the added solution to the surrounding concentration of CS in the sink solution. At a fixed concentration of CS, an increase in the γ-PGA concentration allowed γ-PGA molecules interacting with more CS molecules, and thus formed a lager size of nanoparticles (Table 1a, p<0.05). When the amount of CS molecules exceeded that of local γ-PGA molecules, some of the excessive CS molecules were entangled onto the surfaces of CS-γ-PGA nanoparticles.

Figure 4:
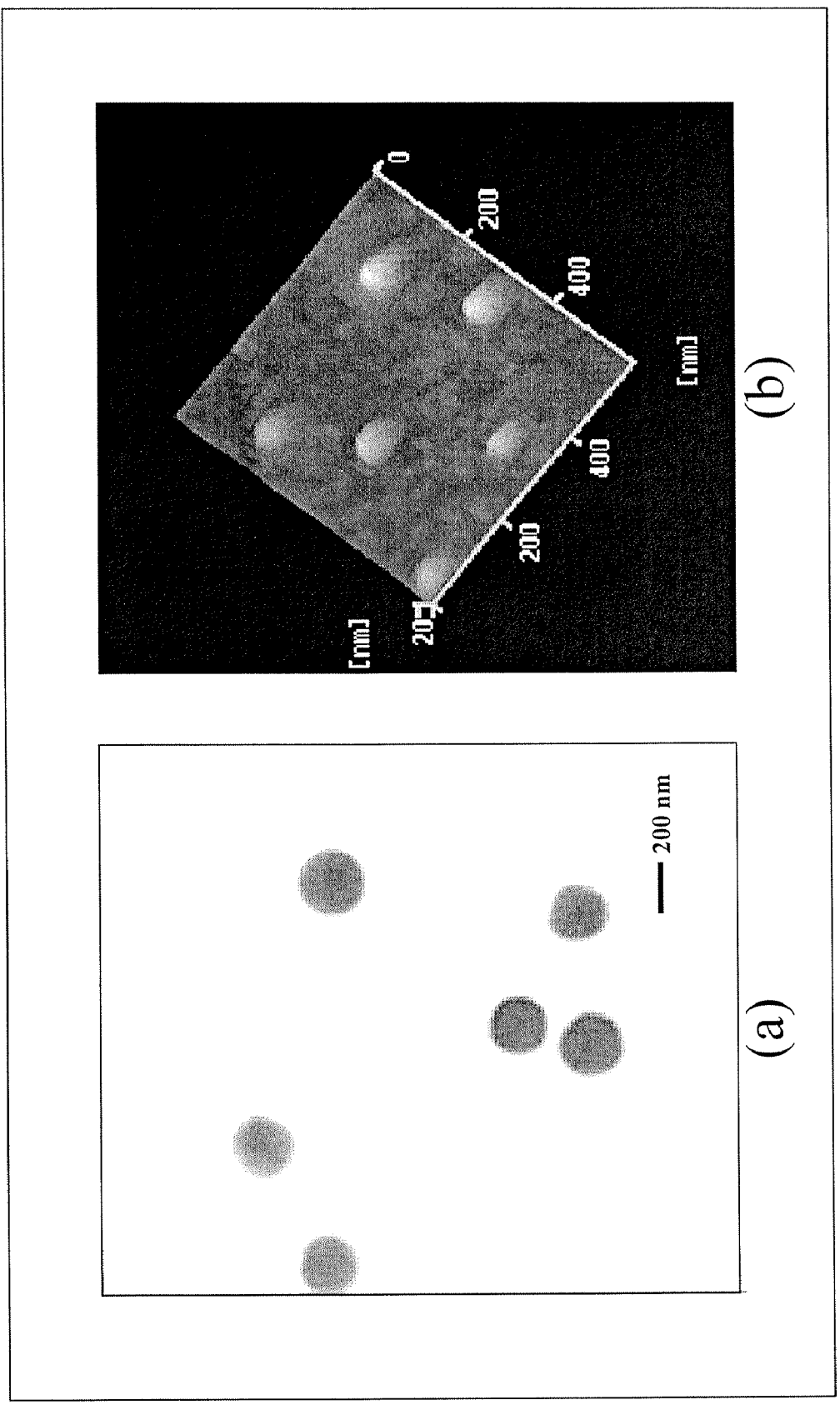
FIG. 4 shows (a) a TEM micrograph of the prepared CS-γ-PGA nanoparticles (0.10% γ-PGA:0.20% CS) and (b) an AFM micrograph of the prepared CS-γ-PGA nanoparticles (0.01% γ-PGA:0.01% CS).

Thus, the resulting nanoparticles may display a structure of a neutral polyelectrolyte-complex core surrounded by a positively charged CS shell (Table 1b) ensuring the colloidal stabilization (Langmuir. 2004; 20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions. The results obtained by the TEM and AFM examinations showed that the morphology of the prepared nanoparticles was spherical in shape with a smooth surface (FIGS. 4a and 4b). Some aspects of the invention relate to nanoparticles having a mean particle size between about 50 and 400 nanometers, preferably between about 100 and 300 nanometers, and most preferably between about 100 and 200 nanometers. The morphology of the nanoparticles shows spherical in shape with a smooth surface at any pH between 2.5 and 6.6. In one embodiment, the stability of the nanoparticles of the present invention at a low pH around 2.5 enables the nanoparticles to be intact when exposed to the gastric acidic medium.

TABLE 1a

Effects of concentrations of γ-PGA and CS on the particle sizes of the prepared CS-γ-PGA nanoparticles
Mean Particle Size (nm, n = 5)

| γ-PGA | CS | | | | |
|---|---|---|---|---|---|
| | 0.01%[a] | 0.05% | 0.10% | 0.15% | 0.20% |
| 0.01%[b] | 79.0 ± 3.0 | 103.1 ± 4.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 4.1 |
| 0.15% | 277.7 ± 3.2 | 264.9 ± 2.1 | 188.6 ± 2.9 | 178.0 ± 2.2 | 301.1 ± 6.4 |
| 0.20% | 284.1 ± 2.1 | 402.2 ± 4.0 | ▲ | 225.5 ± 3.1 | 365.5 ± 5.1 |

[a] concentration of CS (by w/v)
[b] concentration of γ-PGA (by w/v)
▲ precipitation of aggregates was observed TABLE 1b Effects of concentrations of γ-PGA and CS on the zeta potential values of the prepared CS-γ-PGA nanoparticles.
Zeta Potential (mV, n = 5)

| γ-PGA | CS | | | | |
|---|---|---|---|---|---|
| | 0.01%[a] | 0.05% | 0.10% | 0.15% | 0.20% |
| 0.01%[b] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

Figure 5:
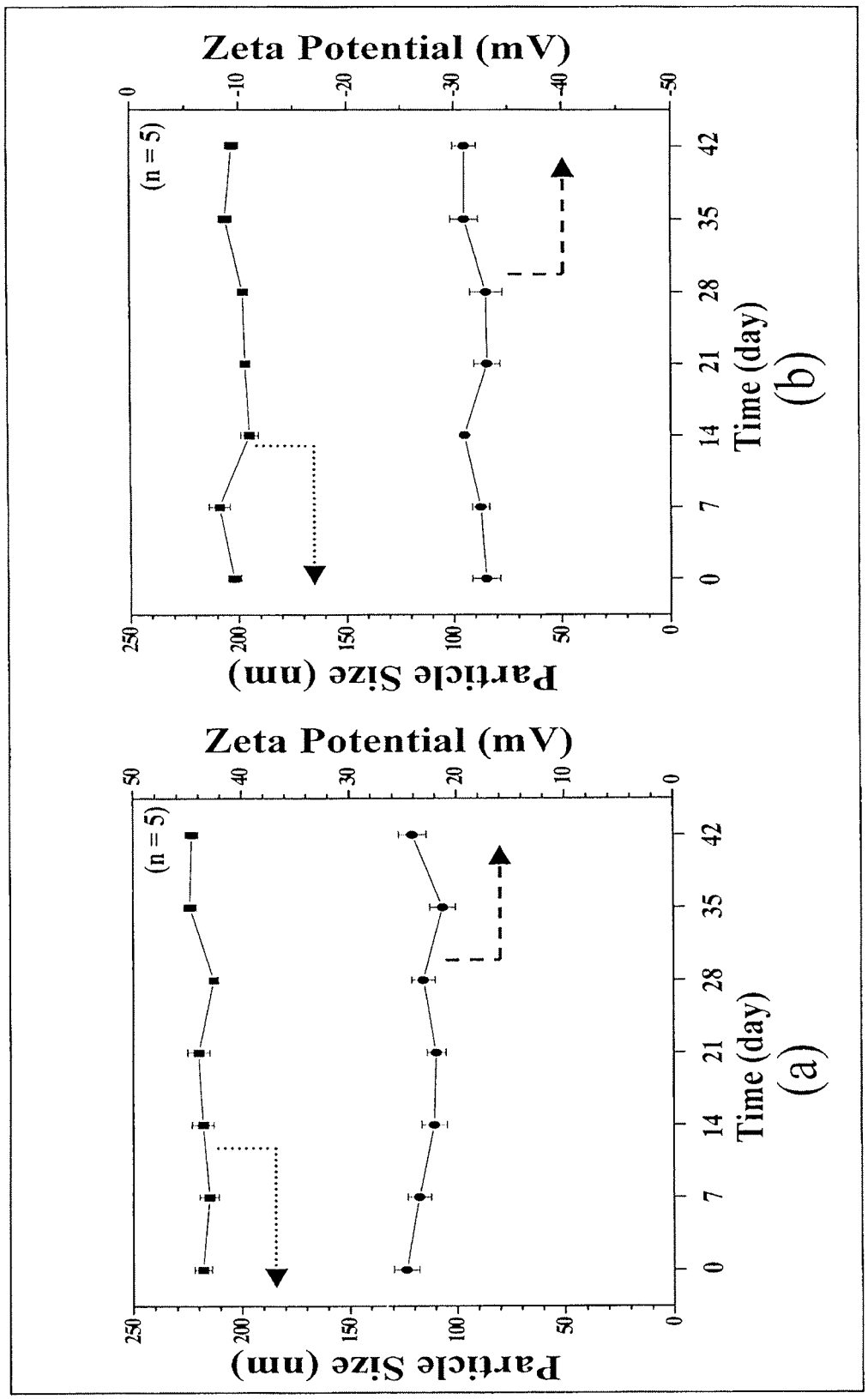
FIG. 5 shows changes in particle size and zeta potential of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks.

[a] concentration of CS (by w/v)
[b] concentration of γ-PGA (by w/v)
▲ precipitation of aggregates was observed Two representative groups of the prepared nanoparticles were selected for the stability study: one with a positive surface charge (0.10% γ-PGA:0.20% CS) and the other with a negative surface charge (0.10% γ-PGA:0.01% CS). FIG. 5 shows changes in particle size (■, mean diameter) and zeta potential (●) of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks. It was found that neither aggregation nor precipitation of nanoparticles was observed during storage for up to 6 weeks, as a result of the electrostatic repulsion between the positively charged CS-γ-PGA nanoparticles (for the former group) or the negatively charged CS-γ-PGA nanoparticles (for the latter group).

Additionally, changes in particle size and zeta potential of the nanoparticles were minimal for both studied groups (FIGS. 5a and 5b). These results demonstrated that the prepared nanoparticles suspended in deionized water were stable during storage.

In a further study, NPs were self-assembled instantaneously upon addition of an aqueous γ-PGA into an aqueous TMC (N-trimethyl chitosan) having a TMC/γ-PGA weight ratio of 6:1 under magnetic stirring at room temperature. Other chitosan derivative, such as mono-N-carboxymethyl chitosan (MCC), has also been useful in self-assembled nanoparticle formation. The chemical formulas of chitosan, N-trimethyl chitosan, and MCC are shown below:

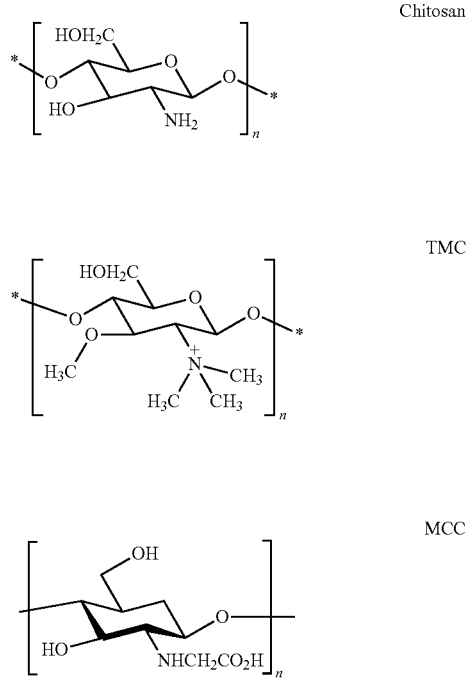

Furthermore, other chitosan derivative, such as NPCS, has also been useful in self-assembled nanoparticle formation. N-palmitoyl CS(NPCS) is made of a hydrophobic palmitoyl group conjugated onto the free amine groups of CS. NPCS is a comblike polyelectrolyte characterized by the presence of alternating charges (protonated amine groups) and hydrophobic side chains.

The amount of positively charged TMC significantly exceeded that of negatively charged γ-PGA; some of excessive TMC molecules were entangled onto the surfaces of NPs, thus displaying a positive surface charge (Table 2). The degree of quaternization on TMC had little effects on the mean particle size and zeta potential of NPs. In Table 2, TMC25, TMC40 and TMC55 indicate an N-trimethyl chitosan with a degree of quaternization of about 25, 40, and 50%, respectively.

Example No. 6 pH-Responsive Characteristics of NPs

The stomach pH is about 1.0 to 2.0 in the presence of food, while the fasting pH of the stomach is 2.5-3.7. The pH values in the duodenum and the jejunum and proximal ileum are 6.0-6.6 and 6.6-7.0, respectively, while the mean pH in the distal ileum and in the body fluid at intercellular spaces between enterocytes is about 7.4. Therefore, characterization of test NPs in response to distinct pH environments must be investigated. TMC is a positively charged polymer and has been used as an intestinal permeation enhancer, and its mechanism of opening tight junctions is similar to that of protonated CS. Additionally, TMC showed no indication of epithelial damage or cytotoxicity. The basic mechanism of the present disclosure is that the orally administered NPs with excessive mucoadhesive TMC on their surfaces may adhere and infiltrate into the mucus of the intestinal tract, and then mediate transiently opening the tight junctions between enterocytes. It is known that the tight junctions opened by absorption enhancers are less than 20 nm in width. Consequently, the NPs infiltrated into the mucus must become unstable (swelling or disintegration); thus their loaded insulin can be released and permeated through the paracellular pathway to the bloodstream.

TABLE 2

Mean particle sizes, zeta potential values and polydispersity indices of nanoparticles (NPs) self-assembled by TMC polymers with different degrees of quaternization and γ-PGA (n = 5 batches). TMC: N-trimethyl chitosan; CS: chitosan; γ-PGA: poly(γ-glutamic acid).

| | Mean Particle Size (nm) | Zeta Potential (mV) | Polydispersity Index |
|---|---|---|---|
| CS/γ-PGA NPs | 104.1 ± 1.2 | 36.2 ± 2.5 | 0.11 ± 0.02 |
| TMC25/γ-PGA NPs | 101.3 ± 3.1 | 30.9 ± 2.1 | 0.13 ± 0.04 |
| TMC40/γ-PGA NPs | 106.3 ± 2.3 | 32.3 ± 2.1 | 0.15 ± 0.14 |
| TMC55/γ-PGA NPs | 114.6 ± 2.3 | 30.6 ± 3.8 | 0.12 ± 0.03 |

It is known that the pKa values of CS (amine groups) and γ-PGA (carboxylic groups) are 6.5 and 2.9, respectively. In the study, NPs were prepared in DI water (pH 6.0). At pH 6.0, CS (TMC25) and γ-PGA were ionized. The ionized CS (TMC25) and γ-PGA could form polyelectrolyte complexes, which resulted in a matrix structure with a spherical shape. At pH 1.2-2.0, most carboxylic groups on γ-PGA were in the form of —COOH. Hence, there was little electrostatic interaction between CS (TMC25) and γ-PGA; thus NPs became disintegrated. Similarly, at pH values above 6.6, the free amine groups on CS (TMC25) were deprotonated; thus leading to the disintegration of NPs. This might limit the efficacy of drug delivery and absorption in the small intestine.

With increasing the degree of quaternization on TMC (TMC40 and TMC55), the stability of NPs in the pH range of 6.6-7.4 increased significantly. However, the swelling of TMC55/γ-PGA NPs at pH 7.4 was minimal (due to the highly quaternized TMC55), which might limit the release of loaded drugs. In contrast, TMC40/γ-PGA NPs swelled significantly with increasing the pH value. TMC40/γ-PGA NPs (or fragments) still retained a positive surface charge with a zeta potential value of 17.3 mV at pH 7.4. Thus, TMC40/γ-PGA/drug NPs had superior stability in a broader pH range to CS/γ-PGA/drug NPs. In one embodiment, at around body fluid pH of about 7.4, the bioactive nanoparticles of the present invention may appear to be in configuration of chitosan-shelled fragments or chitosan-containing fragments. At least a portion of the surface of the chitosan-shelled fragments or chitosan-containing fragments from the bioactive nanoparticles of the present invention shows positive zeta potential characteristics.

The results of molecular dynamic simulations showed that the molecular chains of TMC40 and γ-PGA in their self-assembled complex were tightly entangled to each other at pH 6.0. The surface of the complex was dominated by TMC40 molecules. Relaxations of TMC40 and γ-PGA molecular chains at pH 2.5 resulted in a moderate swelling of the TMC40/γ-PGA complex, while its surface was still dominated by the positively charged TMC molecules, thus retaining a positive surface charge. Similarly, relaxations of TMC40 and γ-PGA molecular chains at pH 7.4 resulted in a significant swelling of the TMC40/γ-PGA complex, while its surface was still dominated by the positively charged TMC molecules, thus retaining a positive surface charge. The swollen TMC40/γ-PGA/drug nanoparticles tend to slightly disintegrate so to form fragments consisting of TMC40/γ-PGA/drug with surface-dominated TMC40. The TMC40/γ-PGA/drug fragments with surface-dominated TMC40 would adhere and infiltrate into the mucus of the epithelial membrane of the blood-brain barrier, and then mediate transiently opening the tight junctions between enterocytes.

Example No. 7

Caco-2 Cell Cultures and TEER Measurements

Caco-2 cells were seeded on the tissue-culture-treated polycarbonate filters (diameter 24.5 mm, growth area 4.7 $cm^2$) in Costar Transwell 6 wells/plates (Corning Costar Corp., NY) at a seeding density of 3×10' cells/insert. MEM (pH 7.4) supplemented with 20% FBS, 1% NEAA, and 40 μg/ml antibiotic-gentamicin was used as the culture medium, and added to both the donor and acceptor compartments. The medium was replaced every 48 hours for the first 6 days and every 24 hours thereafter. The cultures were kept in an atmosphere of 95% air and 5% CO, at 37° C. and were used for the paracellular transport experiments 18-21 days after seeding (TEER values in the range of 600-800 $\Omega cm^2$).

TEER values of the Caco-2 cell monolayers were monitored with a Millicell®-Electrical Resistance System (Millipore Corp., Bedford, Mass.) connected to a pair of chopstick electrodes. To initiate the transport experiments, the culture media in the donor and acceptor compartments were aspirated, and the cells were rinsed twice with pre-warmed transport media (HBSS supplemented with 25 mM glucose, pH 6.0). Following a 30-min equilibration with the transport media at 37° C., the cells were incubated for 2 hours with 2 ml transport media containing 0.5 ml test nanoparticle solutions (0.2 mg/ml) at 37° C. Subsequently, solutions of nanoparticles were carefully removed and cells were washed three times with HBSS and replaced by fresh culture media. The TEER was measured for another 20 hours to study reversibility of the effect of test nanoparticles on Caco-2 cell monolayers.

The intercellular tight junction is one of the major barriers to the paracellular transport of macromolecules (J. Control. Release 1996; 39:131-138; J. Control. Release 1998; 51:35-46). Trans-epithelial ion transport is contemplated to be a good indication of the tightness of the junctions between cells and was evaluated by measuring TEER of Caco-2 cell monolayers in the study. It was reported that the measurement of TEER can be used to predict the paracellular transport of hydrophilic molecules (Eur. J. Pharm. Biopharm. 2004; 58:225-235). When the tight junctions open, the TEER value will be reduced due to the water and ion passage through the paracellular route. Caco-2 cell monolayers have been widely used as an in vitro model to evaluate the intestinal paracellular permeability of macromolecules.

Figure 6:
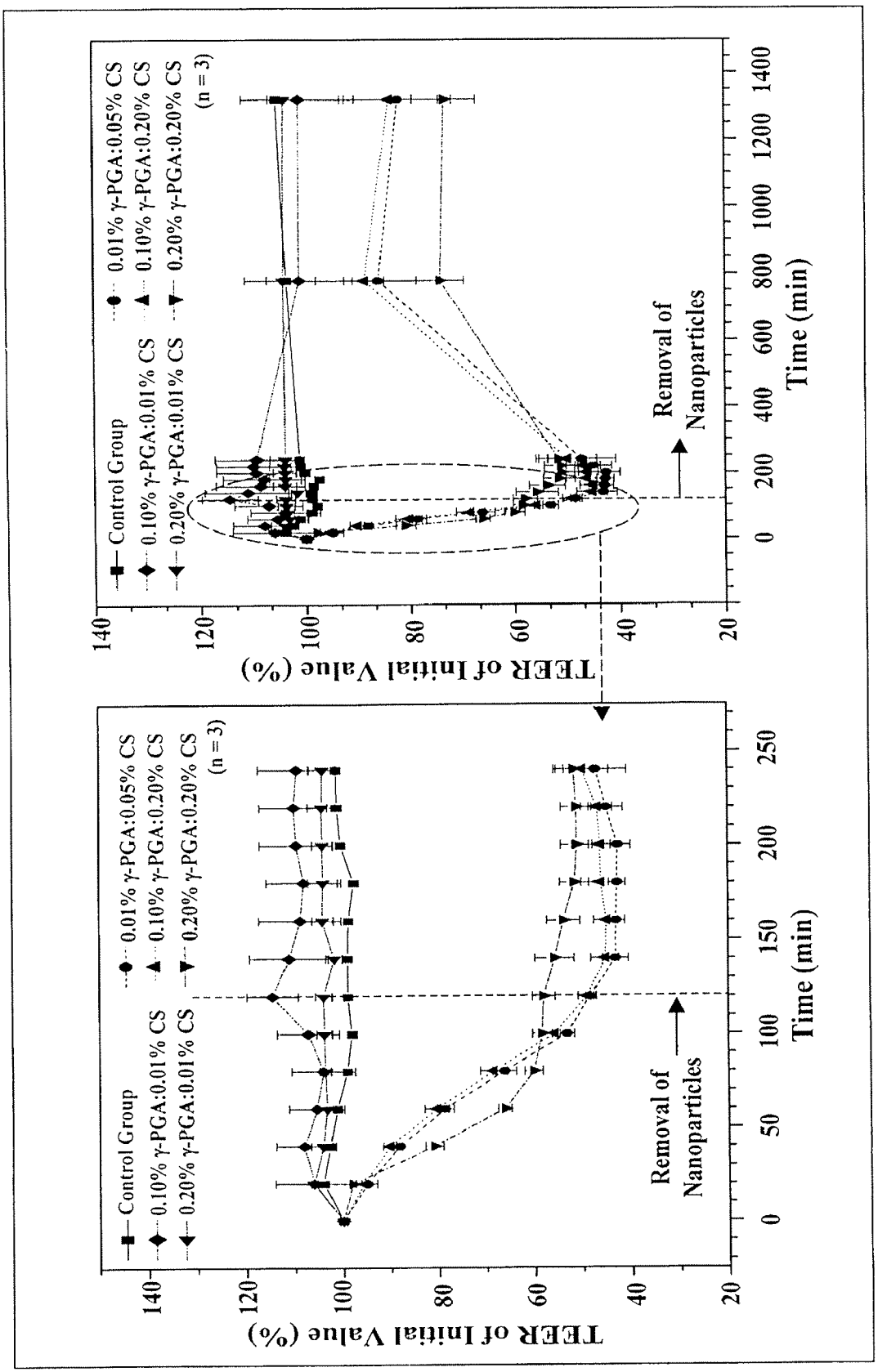
FIG. 6 shows effects of the prepared CS-γ-PGA nanoparticles on the TEER values of Caco-2 cell monolayers.

Effects of the prepared CS-γ-PGA nanoparticles on the TEER values of Caco-2 cell monolayers are shown in FIG. 6. As shown, the prepared nanoparticles with a positive surface charge (CS dominated on the surface, 0.01% γ-PGA:0.05% CS, 0.10% γ-PGA:0.2% CS, and 0.20% γ-PGA:0.20% CS) were able to reduce the values of TEER of Caco-2 cell monolayers significantly ($p<0.05$). After a 2-hour incubation with these nanoparticles, the TEER values of Caco-2 cell monolayers were reduced to about 50% of their initial values as compared to the control group (without addition of nanoparticles in the transport media). This indicated that the nanoparticles with CS dominated on the surfaces could effectively open or loosen the tight junctions between Caco-2 cells, resulting in a decrease in the TEER values. It was reported that interaction of the positively charged amino groups of CS with the negatively charged sites on cell surfaces and tight junctions induces a redistribution of F-actin and the tight junction's protein ZO-1, which accompanies the increased paracellular permeability. It is suggested that an interaction between chitosan and the tight junction protein ZO-1, leads to its translocation to the cytoskeleton.

After removal of the incubated nanoparticles, a gradual increase in TEER values was noticed. This phenomenon indicated that the intercellular tight junctions of Caco-2 cell monolayers started to recover gradually; however, the TEER values did not recover to their initial values (FIG. 6). Kotzé et al. reported that complete removal of a CS-derived polymer, without damaging the cultured cells, was difficult due to the highly adhesive feature of CS (Pharm. Res. 1997; 14:1197-1202). This might be the reason why the TEER values did not recover to their initial values. In contrast, the TEER values of Caco-2 cell monolayers incubated with the nanoparticles with a negative surface charge (γ-PGA dominated on the surface, 0.10% γ-PGA:0.01% CS and 0.20% γ-PGA:0.01% CS, FIG. 6) showed no significant differences as compared to the control group ($p>0.05$). This indicated that γ-PGA does not have any effects on the opening of the intercellular tight junctions.

Transformation of chitosan into nanoparticles significantly promoted its association with the Caco-2 cell monolayers. It also enabled the polymer to be internalized by the cells through clathrin-dependent endocytosis pathway (Pharmaceutical Research 2003; 20:1812-1819). Endocytosis is a process where cells absorb material (molecules such as proteins) from the outside by engulfing it with their cell membrane.

Figure 8:
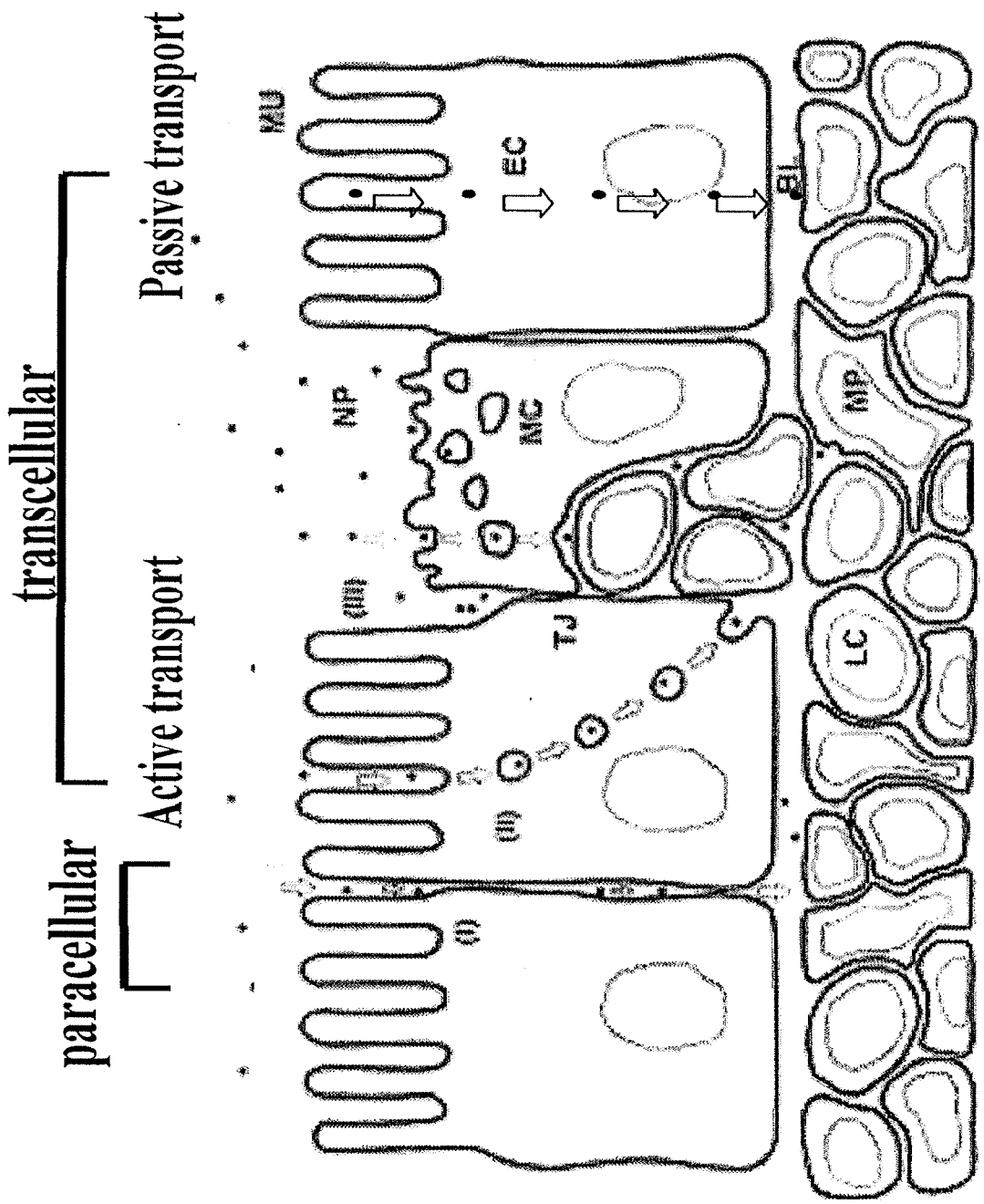
FIG. 8 shows an illustrative protein transport mechanism through a cell layer, including transcellular transport and paracelluler transport.
Figure 9:
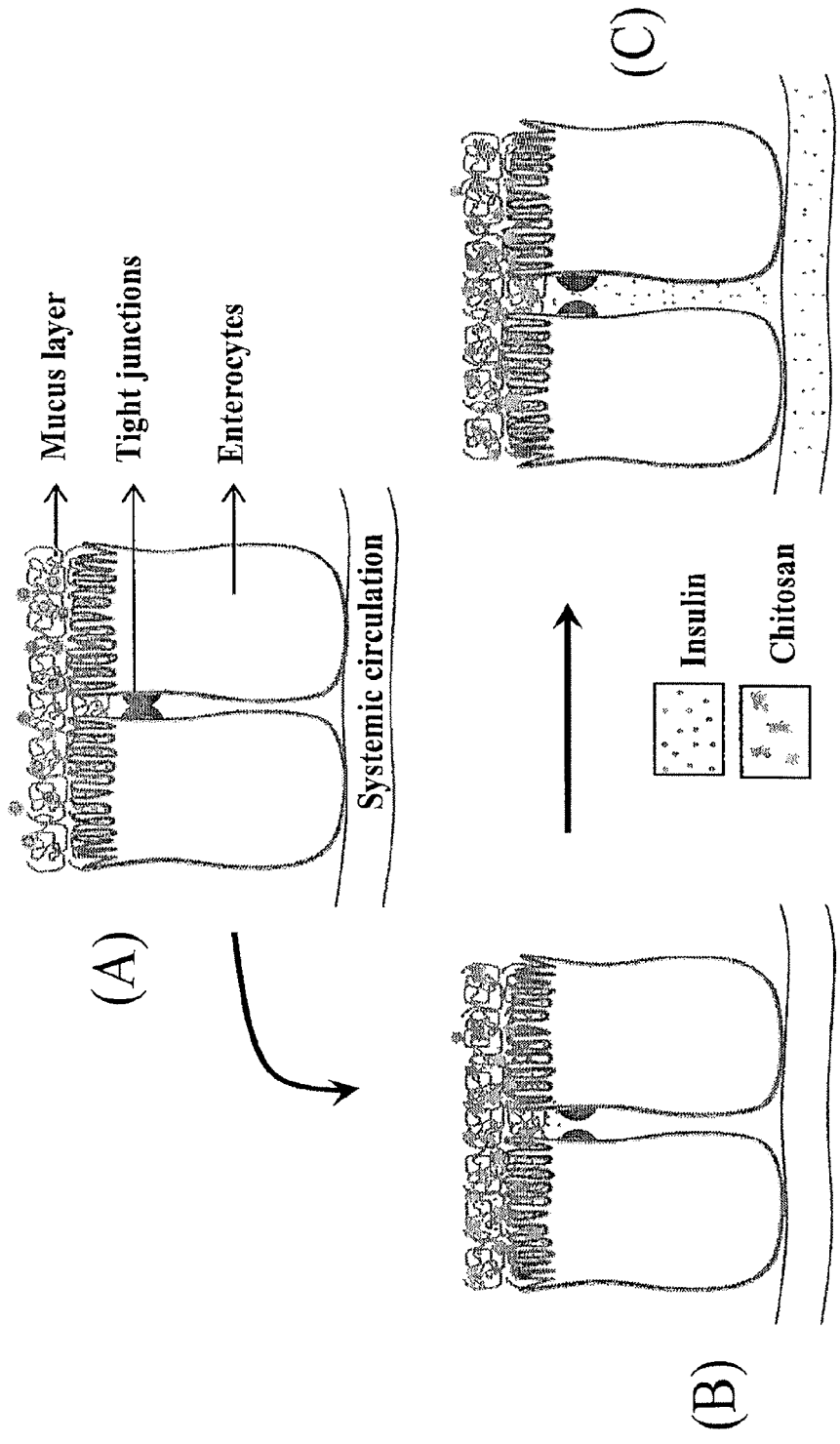
FIGS. 9A-C show a schematic illustration of a paracellular transport mechanism.

FIG. 8 shows an illustrative protein transport mechanism through a cellular layer, including transcellular transport and paracellular transport. FIG. 9 shows a schematic illustration of a paracellular transport mechanism. The transcellular protein or peptide transport may be an active transport or a passive transport mode whereas the paracellular transport is basically a passive mode. Ward et al. reported and reviewed current knowledge regarding the physiological regulation of tight junctions and paracellular permeability (PSTT 2000; 3:346-358). Chitosan as nanoparticle vehicles for oral delivery of protein drugs avoids the enzymatic inactivation in the gastrointestinal conduit. The chitosan component of the present nanoparticles has a special feature of adhering to the mucosal surface and transiently opening the tight junctions between epithelial cells; that is, loosening the tightness of the tight junctions.

FIG. 9(A) shows that after feeding nanoparticles (NPs) orally, NPs adhere and infiltrate into the mucus layer of the epithelial cells. FIG. 9(B) illustrates that the infiltrated NPs transiently and reversibly loosen tight junctions (TJs) while becoming unstable and disintegrated to release insulin or entrapped agent. FIG. 9(c) shows that the released insulin or API permeates through the paracellular pathway into the blood stream. Here, a complexone (EGTA, EDTA, EGTA, and the like) has been shown to transiently and reversibly widen/open the tight junctions by removing $Ca^{2+}$ ions from the basolateral side of epithelial cells. Alternately, chitosan (CS), a nontoxic, soft-tissue compatible, cationic polysaccharide has special features of adhering to the mucosal surface; CS is able to transiently and reversibly widen/loosen TJs between epithelial cells. The TJ width in the small intestine has been demonstrated to be less than 1 nm. It is also known that TJs 'opened' by absorption enhancers are less than 20 nm wide (Nanotechnology 2007; 18:1-11). The term "opened" herein means that any substance less than 20 nm in the close-proximity might have the chance to pass through. TJs constitute the principal barrier to passive movement of fluid, electrolytes, macromolecules and cells through the paracellular pathway.

It was suggested that the electrostatic interaction between the positively charged CS and the negatively charged sites of ZO-1 proteins on cell surfaces at TJ induces a redistribution of cellular F-actin and ZO-1's translocation to the cytoskeleton, leading to an increase in paracellular permeability. As evidenced in FIG. 9, after adhering and infiltrating into the mucus layer of the duodenum, the orally administered nanoparticles may degrade due to the presence of distinct digestive enzymes in the intestinal fluids. Additionally, the pH environment may become neutral while the nanoparticles were infiltrating into the mucosa layer and approaching the intestinal epithelial cells. This further leads to the collapse of nanoparticles due to the change in the exposed pH environment. The dissociated CS from the degraded/collapsed nanoparticles was then able to interact and modulate the function of ZO-1 proteins between epithelial cells (Nanotechnology 2007; 18:1-11). ZO-1 proteins are thought to be a linkage molecule between occludin and F-actin cytoskeleton and play important roles in the rearrangement of cell-cell contacts at TJs.

Example No. 8 fCS-γ-PGA Nanoparticle Preparation and CLSM Visualization

Fluorescence (FITC)-labeled CS-γ-PGA (fCS-γ-PGA) nanoparticles were prepared for the confocal laser scanning microscopy (CLSM) study. The nanoparticles of the present invention display a structure of a neutral polyelectrolyte-complex core surrounded by a positively charged chitosan shell. Synthesis of the FITC-labeled low-MW CS (fCS) was based on the reaction between the isothiocyanate group of FITC and the primary amino groups of CS as reported in the literature (Pharm. Res. 2003; 20:1812-1819). Briefly, 100 mg of FITC in 150 ml of dehydrated methanol were added to 100 ml of 1% low-MW CS in 0.1M acetic acid. After 3 hours of reaction in the dark at ambient conditions, fCS was precipitated by raising the pH to about 8-9 with 0.5MNaOH. To remove the unconjugated FITC, the precipitate was subjected to repeated cycles of washing and centrifugation (40,000×g for 10 min) until no fluorescence was detected in the supernatant. The fCS dissolved in 80 ml of 0.1M acetic acid was then dialyzed for 3 days in the dark against 5 liters of distilled water, with water replaced on a daily basis. The resultant fCS was lyophilized in a freeze dryer. The fCS-γ-PGA nanoparticles were prepared as per the procedure described in Example No. 4.

Subsequently, the transport medium containing fCS-γ-PGA nanoparticles (0.2 mg/ml) was introduced into the donor compartment of Caco-2 cells, which were pre-cultured on the transwell for 18-21 days. The experimental temperature was maintained at 37° C. by a temperature control system (DH-35 Culture Dish Heater, Warner Instruments Inc., Hamden, Conn.). After incubation for specific time intervals, test samples were aspirated. The cells were then washed twice with pre-warmed PBS solution before they were fixed in 3.7% paraformaldehyde (Phar. Res. 2003; 20:1812-1819). Cells were examined under an inversed CLSM (TCS SL, Leica, Germany). The fluorescence images were observed using an argon laser (excitation at 488 nm, emission collected at a range of 510-540 nm).

Figure 7:
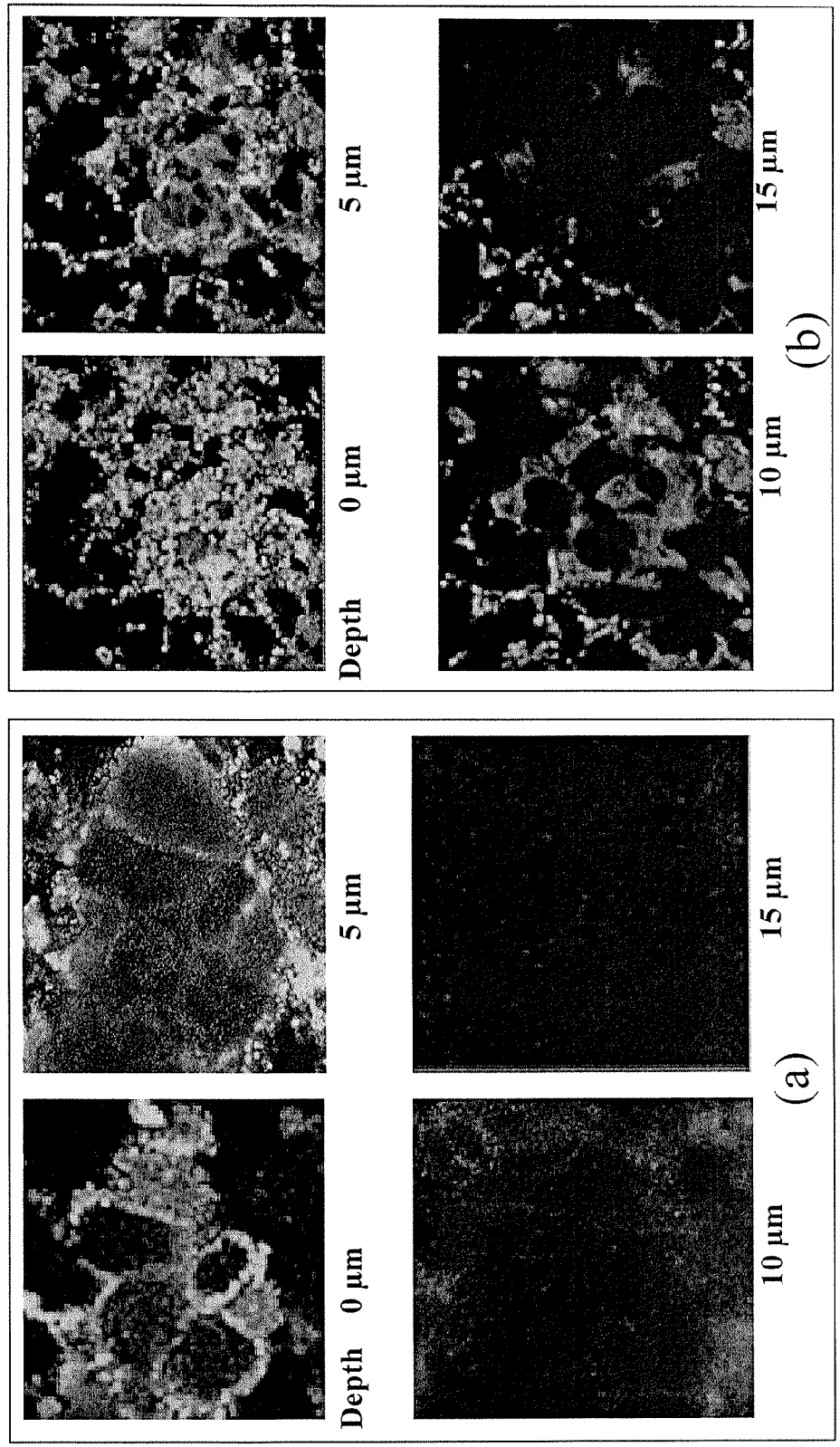
FIG. 7 shows fluorescence images (taken by an inversed confocal laser scanning microscope) of 4 optical sections of a Caco-2 cell monolayer that had been incubated with the fCS-γ-PGA nanoparticles with a positive surface charge (0.10% γ-PGA:0.20% CS) for (a) 20 min and (b) 60 min.

CLSM was used to visualize the transport of the fluorescence-labeled CS-γ-PGA (fCS-γ-PGA) nanoparticles across the Caco-2 cell monolayers. This non-invasive method allows for optical sectioning and imaging of the transport pathways across the Caco-2 cell monolayers, without disrupting their structures. FIGS. 7a and 7b show the fluorescence images of 4 optical sections of a Caco-2 cell monolayer that had been incubated with the fCS-γ-PGA nanoparticles having a positive surface charge (0.10% γ-PGA:0.20% CS, zeta potential: about 21 mV) for 20 and 60 min, respectively. As shown, after 20 min of incubation with the nanoparticles, intense fluorescence signals at intercellular spaces were observed at depths of 0 and 5 pin from the apical (upper) surface of the cell monolayer. The intensity of fluorescence became weaker at levels deeper than 10 μm from the apical surface of the cell monolayer and was almost absent at depths≧15 μm (FIG. 7a).

After 60 minutes of incubation with the nanoparticles, the intensity of fluorescence observed at intercellular spaces was stronger and appeared at a deeper level than those observed at 20 min after incubation. These observations confirmed with our TEER results that the nanoparticles with a positive surface charge (CS dominated on the surface) were able to open the tight junctions between Caco-2 cells and allowed transport of the nanoparticles by passive diffusion via the paracellular pathways.

Example No. 9

In Vivo Study with Fluorescence-Labeled Nanoparticles

Fluorescence (FITC)-labeled CS-γ-PGA (fCS-γ-PGA) nanoparticles were prepared for the confocal laser scanning microscopy (CLSM) study. After feeding rats with fCS-γ-PGA nanoparticles, the rats are sacrificed at a pre-determined time and the intestine is isolated for CLSM examination. The fluorescence images of the nanoparticles were clearly observed by CLSM that penetrates through the mouse intestine at appropriate time and at various depths from the inner surface toward the exterior surface of the intestine, including duodenum, jejunum, and ileum.

Example No. 10

Insulin Loading Capacity in Nanoparticles

Fluorescence (FITC)-labeled γ-PGA was added into chitosan solution to prepare fluorescence (FITC)-labeled, insulin-loaded CS-γ-PGA nanoparticles for in vivo animal study with confocal laser scanning microscopy (CLSM) assessment and bioactivity analysis. The insulin-loaded CS-γ PGA nanoparticles are by using the ionic-gelation method upon addition of insulin mixed with γ-PGA solution into CS solution, followed by magnetic stirring in a container.

Model insulin used in the experiment and disclosed herein is obtained from bovine pancreas (Sigma-Aldrich, St. Louis, Mo.), having a molecular formula of $C_{254}H_{377}N_{65}O_{75}S_6$ with a molecular weight of about 5733.5 and an activity of ≧27 USP units/mg. The insulin contains two-chain polypeptide hormone produced by the β-cells of pancreatic islets. The cc and 13 chains are joined by two interchain disulfide bonds. Insulin regulates the cellular uptake, utilization, and storage of glucose, amino acids, and fatty acids and inhibits the breakdown of glycogen, protein, and fat. The insulin from Sigma-Aldrich contains about 0.5% zinc. Separately, insulin can be obtained from other sources, such as human insulin solution that is chemically defined, recombinant from *Saccharomyces cerevisiae*. Some aspects of the invention relate to nanoparticles with insulin in the core, wherein the insulin may contain intermediate-acting, regular insulin, rapid-acting insulin, sustained-acting insulin that provides slower onset and longer duration of activity than regular insulin, or combinations thereof.

Examples of insulin or insulin analog products include, but not limited to, Humulin® (by Eli Lilly), Humalog® (by Eli Lilly) and Lantus® (by Aventis), and Novolog® Mix 70/30 (by Novo Nordisk). Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed. Humalog is synthesized in a special non-pathogenic laboratory strain of *Escherichia coli* bacteria that has been genetically altered by the addition of the gene for insulin lispro. Humalog has the empirical formula $C_{257}H_{383}N_{65}O_{77}S_6$ and a molecular weight of 5808, identical to that of human insulin. The vials and cartridges contain a sterile solution of Humalog for use as an injection. Humalog injection consists of zinc-insulin lispro crystals dissolved in a clear aqueous fluid. Each milliliter of Humalog injection contains insulin lispro 100 Units, 16 mg glycerin, 1.88 mg dibasic sodium phosphate, 3.15 mg m-cresol, zinc oxide content adjusted to provide 0.0197 mg zinc ion, trace amounts of phenol, and water for injection. Insulin lispro has a pH of 7.0-7.8. Hydrochloric acid 10% and/or sodium hydroxide 10% may be added to adjust pH.

Humulin is used by more than 4 million people with diabetes around the world every day. Despite its name, this insulin does not come from human beings. It is identical in chemical structure to human insulin and is made in a factory using a chemical process called recombinant DNA technology. Humulin L is an amorphous and crystalline suspension of human insulin with a slower onset and a longer duration of activity (up to 24 hours) than regular insulin. Humulin U is a crystalline suspension of human insulin with zinc providing a slower onset and a longer and less intense duration of activity (up to 28 hours) than regular insulin or the intermediate-acting insulins (NPH and Lente).

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ and a molecular weight of 6063.

LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection. In 2006, there were 11.4 million prescriptions of Lantus in the U.S. for basal insulin maintenance.

Novolog® Mix 70/30 (70% insulin aspart protamine suspension and 30% insulin aspart injection [rDNA origin]) is a human insulin analog suspension. Novolog® Mix70/30 is a blood glucose-lowering agent with a rapid onset and an intermediate duration of action. Insulin aspart is homologous with regular human insulin with the exception of a single substitution of the amino acid praline by aspartic acid in position B28, and is produced by recombinant DNA technology utilizing *Saccharomyces cerevisiae* as the production organism. Insulin aspart (Novolog) has the empirical formula $C_{256}H_{381}N_{65}O_{79}S_6$ and a molecular weight of 5826. Novolog® Mix 70/30 is a uniform, white sterile suspension that contains zinc 19.6 μg/ml and other components.

The nanoparticles with two insulin concentrations are prepared at a chitosan to γ-PGA ratio of 0.75 mg/ml to 0.167 mg/ml. Their particle size and zeta potential are shown in Table 3 below.

TABLE 3

| Insulin Conc. (mg/ml) (n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

*control reference without insulin

Figure 11:
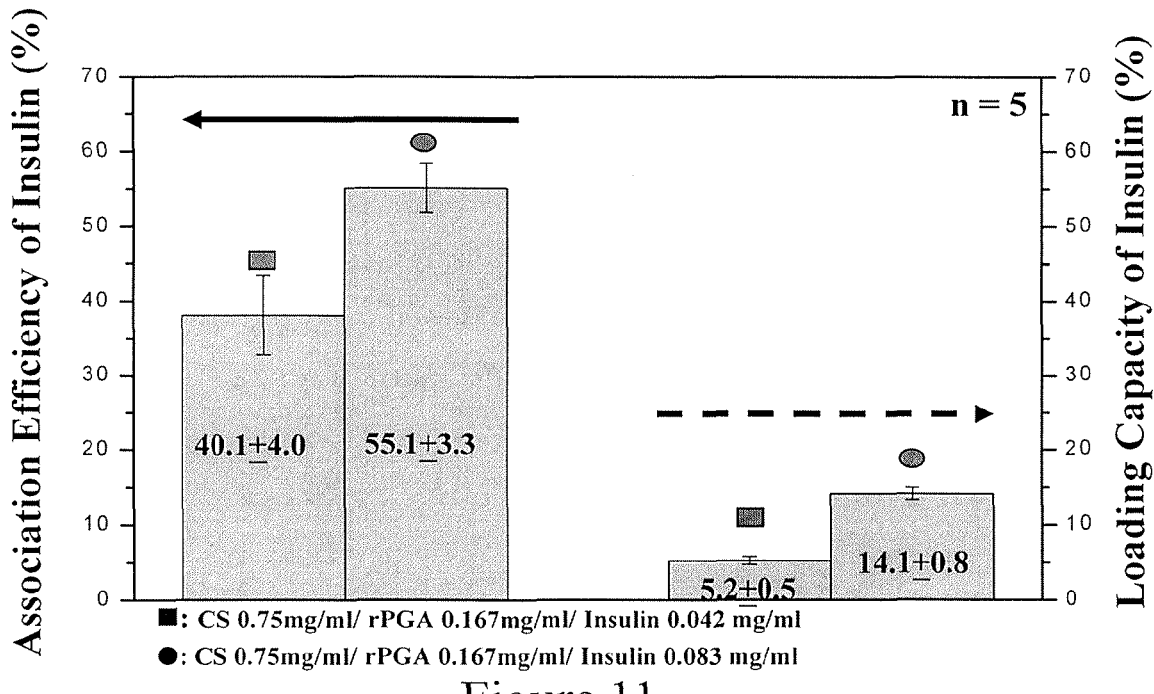
FIG. 11 shows loading capacity and association efficiency of insulin in nanoparticles of chitosan and γ-PGA.
Figure 12:
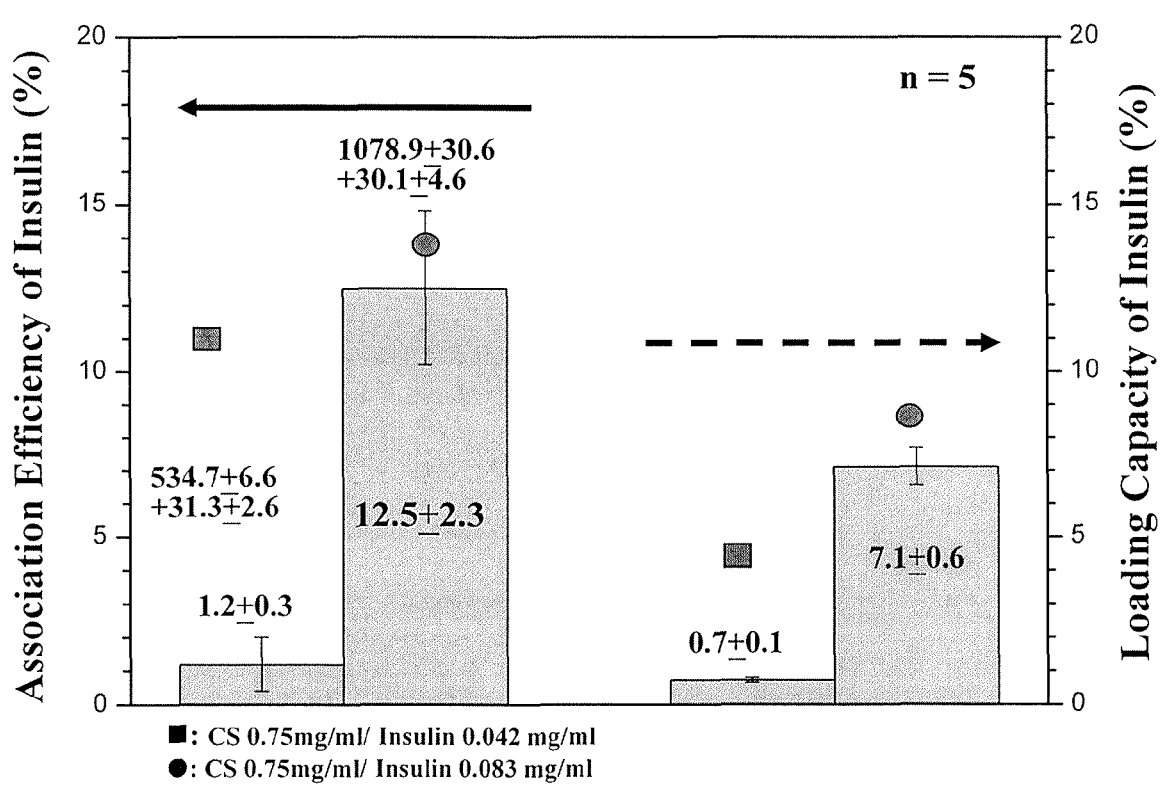
FIG. 12 shows loading capacity and association efficiency of insulin in nanoparticles of chitosan as reference.

Further, their association efficiency of insulin and loading capacity of insulin are analyzed, calculated and shown in FIGS. 11 and 12, according to the following formula:

$$\text{Insulin Association Efficiency } (LE\%) = \frac{\text{(Total amount of insulin} - \text{Insulin in supernatant)}}{\text{Total amount of insulin}} \times 100\%$$

$$\text{Loading Capacity } (LC) = \frac{\text{(Total amount of insulin} - \text{Insulin in supernatant)}}{\text{Weight of recovered particles}} \times 100\%$$

FIG. 11 shows loading capacity and association efficiency of insulin in nanoparticles of chitosan and γ-PGA, whereas FIG. 12 shows loading capacity and association efficiency of insulin in nanoparticles of chitosan alone (in absence of γ-PGA) as reference. The data clearly demonstrates that both the insulin loading capacity and insulin association efficiency are statistically higher for the nanoparticles with γ-PGA in the core. The LE (40~55%) and LC (5.0~14.0%) of insulin for CS-γ PGA nanoparticles was obtained by using ionic-gelation method upon addition of insulin mixed with γ-PGA solution into CS solution, followed by magnetic stirring for nanoparticle separation.

In certain follow-up experiments, nanoparticles having a pharmaceutical composition have been successfully prepared with a negatively charged component comprised of γ-PGA, α-PGA, PGA derivatives, salts of PGA, heparin or heparin analog, glycosaminoglycans, or alginate. The PGA derivatives of the present invention may include, but not limited to, poly-γ-glutamic acid, poly-α-glutamic acid, poly-L-glutamic acid (manufactured by Sigma-Aldrich, St. Louis, Mo.), poly-D-glutamic acid, poly-L-α-glutamic acid, poly-γ-D-glutamic acid, poly-γ-DL-glutamic acid, and PEG or PHEG derivatives of polyglutamic acid, salts of the above-cited PGAs, and the like. Some aspects of the invention relate to nanoparticles comprising a shell component and a core component, wherein at least a portion of the shell component comprises chitosan and wherein the core component is comprised of a negatively charged compound that is conjugated to chitosan, and a bioactive agent.

The nanoparticle of the present invention that contains at least one bioactive agent is generally referred herein as "bioactive nanoparticle" (also known as "therapeutic nanoparticle"). Some aspects of the invention relate to an oral dose of nanoparticles that effectively enhance intestinal or blood brain paracellular transport comprising a negative component (such as γ-PGA, α-PGA, PGA derivatives, heparin, or alginate) and at least one enzyme-resistant agent in the core, wherein the negatively charged substrate is at least partially neutralized with a portion of the positively charged chitosan, wherein the chitosan dominates on a surface of the nanoparticles with positive charges. In one embodiment, the enzyme-resistant agent is complexone, such as diethylene triamine pentaacetic acid (DTPA) or ethylene diamine tetraacetic acid (EDTA), which conjugates with the chitosan substrate or the PGA substrate in the nanoparticle formulation.

Nanoparticles Loaded with DTPA

Some aspects of the invention relate to a pharmaceutical composition of nanoparticle comprising chitosan, PGA-complexone conjugate and a bioactive agent. In one embodiment, the PGA-complexone conjugate may broadly include a conjugate with PGA derivatives such as γ-PGA, a-PGA, derivatives of PGA or salts of PGA, whereas the complexone may cover DTPA (diethylene triamine pentaacetic acid), EDTA (ethylene diamine tetra acetate), IDA (iminodiacetic acid), NTA (nitrilotriacetic acid), EGTA (ethylene glycol tetraacetic acid), BAPTA (1,2-bis(o-aminophenoxy)ethane-N,N,N',N'-tetraacetic acid), DOTA (1,4,7,10-tetraazacyclododecane-N,N,N,N'-tetraacetic acid), NOTA (2,2',2''-(1,4,7-triazonane-1,4,7-triyl)triacetic acid), and the like. A polyamino carboxylic acid (complexone) is a compound containing one or more nitrogen atoms connected through carbon atoms to one or more carboxyl groups.

Diethylene triamine pentaacetic acid (DTPA) is a polyamino carboxylic acid consisting of a diethylenetriamine backbone modified with five carboxymethyl groups. The molecule can be viewed as an expanded version of EDTA. DTPA is used as its conjugate base, often undefined, which has a high affinity for metal cations. In example, upon complexation to lanthanide and actinide ions, DTPA exists as the pentaanionic form, i.e. all five carboxylic acid groups are deprotonated. DTPA has a molecular formula of $C_{14}H_{23}N_3O_{10}$ with molar mass 393.358 g/mole and a chemical formula as:

DTPA Formula

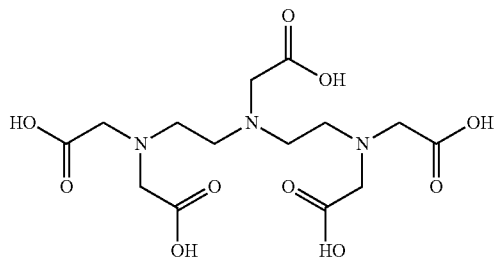

Currently, DTPA is approved by the U.S. Food and Drug Administration (FDA) for chelation of three radioactive materials: plutonium, americium, and curium. DTPA is the parent acid of an octadentate ligand, diethylene triamine pentaacetate. In some situations, all five acetate arms are not attached to the metal ion. In one aspect of the present invention, DTPA has been conjugated to γ-PGA through hexanediamine ((γ-PGA)-DTPA) as illustrated below:

(γ-PGA)-DTPA

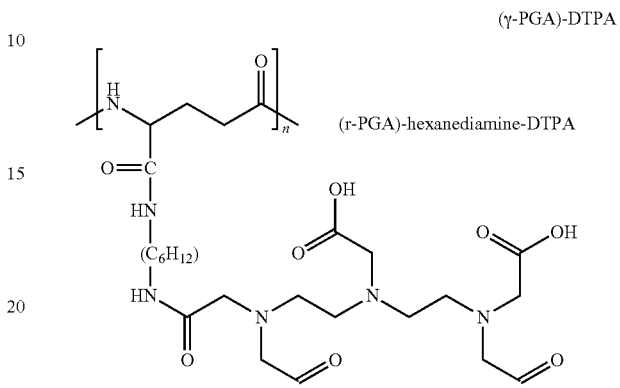

(r-PGA)-hexanediamine-DTPA

In one aspect of the invention, (γ-PGA)-DTPA is one species of the PGA-complexone conjugates used in the current pharmaceutical composition of nanoparticles. The overall degree of substitution of DTPA in (γ-PGA)-DTPA conjugate is generally in the range of about 1-70%, preferably in the range of about 5-40%, and most preferably in the range of about 10-30%. DTPA does not build up in the body or cause long-term health effects.

Nanoparticles comprising chitosan, PGA-complexone conjugates and at least one bioactive agent using the simple and mild ionic-gelation process described herein has demonstrated the desired paracellular transport efficacy with TEER measurements in the Caco-2 cell cultures model as described in Example No. 7.

Example No. 11

Enzyme Inhibition Study with (γ-PGA)-DTPA Conjugate

Figure 22:
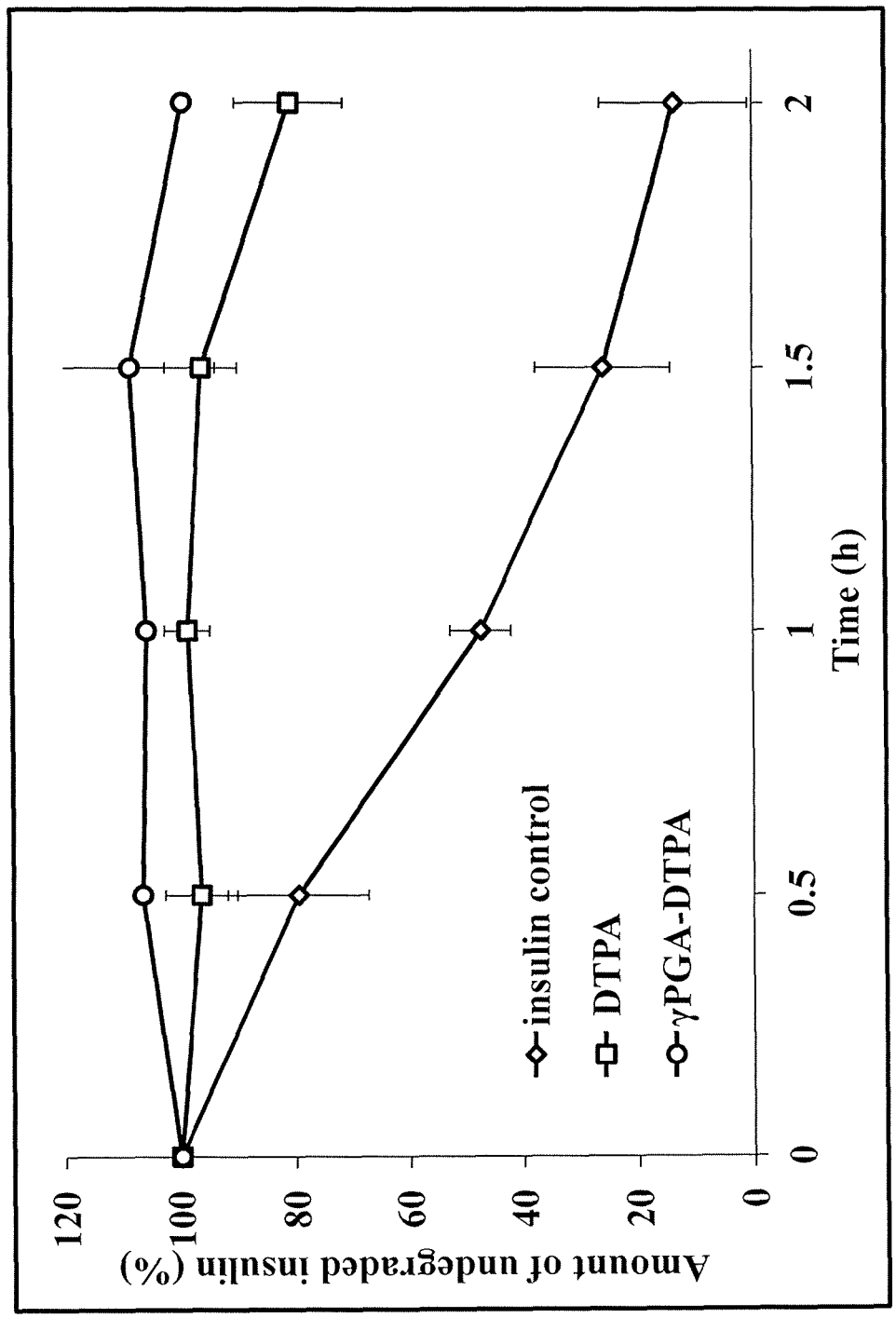
FIG. 22 shows experimental data on enzyme inhibition study with (γ-PGA)-DTPA conjugate.

Brush border membrane bounded enzymes were used to simulate a contacting membrane at the bottom of a donor compartment, wherein the insulin-loaded medium (Krebs-Ringer buffer) in the donor compartment was used as the starting material at time zero. Three elements were used in this enzyme inhibition study to assess the enzymatic degradation of insulin versus time by brush border membrane bounded enzymes. They were (a) insulin 1 mg/ml as control; (b) DTPA 5 mg/ml; and (c) (γ-PGA)-DTPA 5 mg/ml. As shown in FIG. 22, both DTPA and (γ-PGA)-DTPA substantially protect or maintain the insulin activity or viable content over the experimental duration up to 2 hours. Some aspects of the present invention provide a pharmaceutical composition of nanoparticles, the nanoparticles comprising a shell portion that is dominated by positively charged chitosan, a core portion that comprises complexone and one negatively charged substrate, wherein the substrate is PGA, wherein the negatively charged substrate is at least partially neutralized with a portion of the positively charged chitosan in the core portion, and at least one bioactive agent loaded within the nanoparticles. In one embodiment, the PGA is conjugated with the complexone to form PGA-complexion conjugates within the nanoparticles.

Some aspects of the invention provide a method of enhancing enzymatic resistance of a bioactive agent in oral administration by encapsulating the bioactive agent in nanoparticles, wherein the nanoparticles have a pharmaceutical formulation and/or composition as described in this disclosure and in claims. In one embodiment, the nanoparticles are further loaded with pharmaceutically acceptable carrier, diluent, or excipient in tablets, pills, capsules, and the like.

Some aspects of the invention relate to a dose of nanoparticles that effectively enhance intestinal or blood brain paracellular transport comprising a polyanionic component (such as γ-PGA, α-PGA, PGA-DTPA, PGA derivatives, heparin, heparin analogs, low molecular weight heparin, glycosaminoglycans, or alginate) in the core and low molecular weight chitosan in the shell, wherein the chitosan dominates on a surface of the nanoparticles with surface positive charges. In use, firstly, encapsulate the Alzheimer's drug in the chitosan shell nanoparticle as described herein, wherein the nanoparticle is partially crosslinked (optionally) to enhance its biodurability. Then intra-venously inject the nanoparticles, whereby the nanoparticles pass to the brain in blood circulation. The chitosan shell of the nanoparticles adheres to the surface adjacent the tight junction in the brain. Thereafter, the chitosan nanoparticle opens the tight junction, wherein the Alzheimer's drug is released after passing the tight junction for therapeutic treatment. In one embodiment, the nanoparticles are in a spherical shape having a mean particle size of about 50 to 250 nanometers, preferably 150 nanometers to 250 nanometers.

In one example, intravenous administration of the nanoparticles comprising chitosan shell substrate, polyanionic core substrate and at least one bioactive agent for treating Alzheimer's disease in a patient is typically performed with 10 mg to 40 mg of active agent per day over a period of one month to one year. The bioactive agent is selected from the group consisting of donepezile, rivastignine, galantamine, and/or those trade-named products, such as memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis).

Some aspects of the invention relate to a nanoparticle with a core substrate comprising polyglutamic acids such as water soluble salt of polyglutamic acids (for example, ammonium salt) or metal salts of polyglutamic acid (for example, lithium salt, sodium salt, potassium salt, magnesium salt, and the like). In one embodiment, the form of polyglutamic acid may be selected from the group consisting of poly-α-glutamic acid, poly-L-α-glutamic acid, poly-γ-glutamic acid, poly-D-glutamic acid, poly-γ-D-glutamic acid, poly-γ-DL-glutamic acid, poly-L-glutamic acid (manufactured by Sigma-Aldrich, St. Louis, Mo.), and PEG or PHEG derivatives of polyglutamic acid. Alginate is generally non-biodegradable; however, it is stipulated that an alginate particle with about 30-50 kDa molecular weight is kidney inert. Heparin with negatively charged side-groups has a general chemical structure as shown below:

Some aspects of the invention relate to the negatively charged glycosaminoglycans (GAGs) as the core substrate of the present nanoparticles. GAGs may be used to complex with a low-molecular-weight chitosan to form drug-carrier nanoparticles. GAGs may also conjugate with the protein drugs as disclosed herein to enhance the bonding efficiency of the core substrate in the nanoparticles. Particularly, the negatively charged core substrate (such as GAGs, heparin, PGA, alginate, and the like) of the nanoparticles of the present invention may conjugate with chondroitin sulfate, hyaluronic acid, PDGF-BB, BSA, EGF, MK, VEGF, KGF, bFGF, aFGF, MK, PTN, etc.

Calceti et al. reported an in vivo evaluation of an oral insulin-PEG delivery system (Eur J Pharma Sci 2004; 22:315-323). Insulin-PEG was formulated into mucoadhesive tablets constituted by the thiolated polymer poly(acrylic acid)-cysteine. The therapeutic agent was sustained released from these tablets within 5 hours. In vivo, by oral administration to diabetic mice, the glucose levels were found to decrease significantly over the time. Further, Krauland et al. reported another oral insulin delivery study of thiolated chitosan-insulin tablets on non-diabetic rats (J. Control. Release 2004, 95:547-555). The delivery tablets utilized 2-Iminothiolane covalently linked to chitosan to form chitosan-TBA (chitosan-4-thiobutylamidine) conjugate. After oral administration of chitosan-TBA-insulin tablets to non-diabetic conscious rats, the blood glucose level decreased significantly for 24 hours; supporting the observation of sustained insulin release of the presently disclosed nanoparticles herein through intestinal absorption. In a further report by Morcol et al. (Int. J. Pharm. 2004; 277:91-97), an oral delivery system comprising calcium phosphate-PEG-insulin-casein particles displays a prolonged hypoglycemic effect after oral administration to diabetic rats.

Pan et al. disclosed chitosan nanoparticles improving the intestinal absorption of insulin in vivo (Int J Pharma 2002; 249:139-147) with insulin-chitosan nanoparticles at a particle size of 250-400 nm, a polydispersity index smaller than 0.1, positively charged and stable. After administering the insulin-chitosan nanoparticles, it was found that the hypoglycemic was prolonged with enhanced pharmacological bioavailability. Their data confirmed our observation as shown in FIGS. 11 and 12; however, the insulin loading capacity and insulin association efficiency of the present invention are substantially higher for the chitosan-insulin nanoparticles with γ-PGA in the core as the core substrate.

Example No. 12

Insulin Nanoparticle Stability

Figure 13:
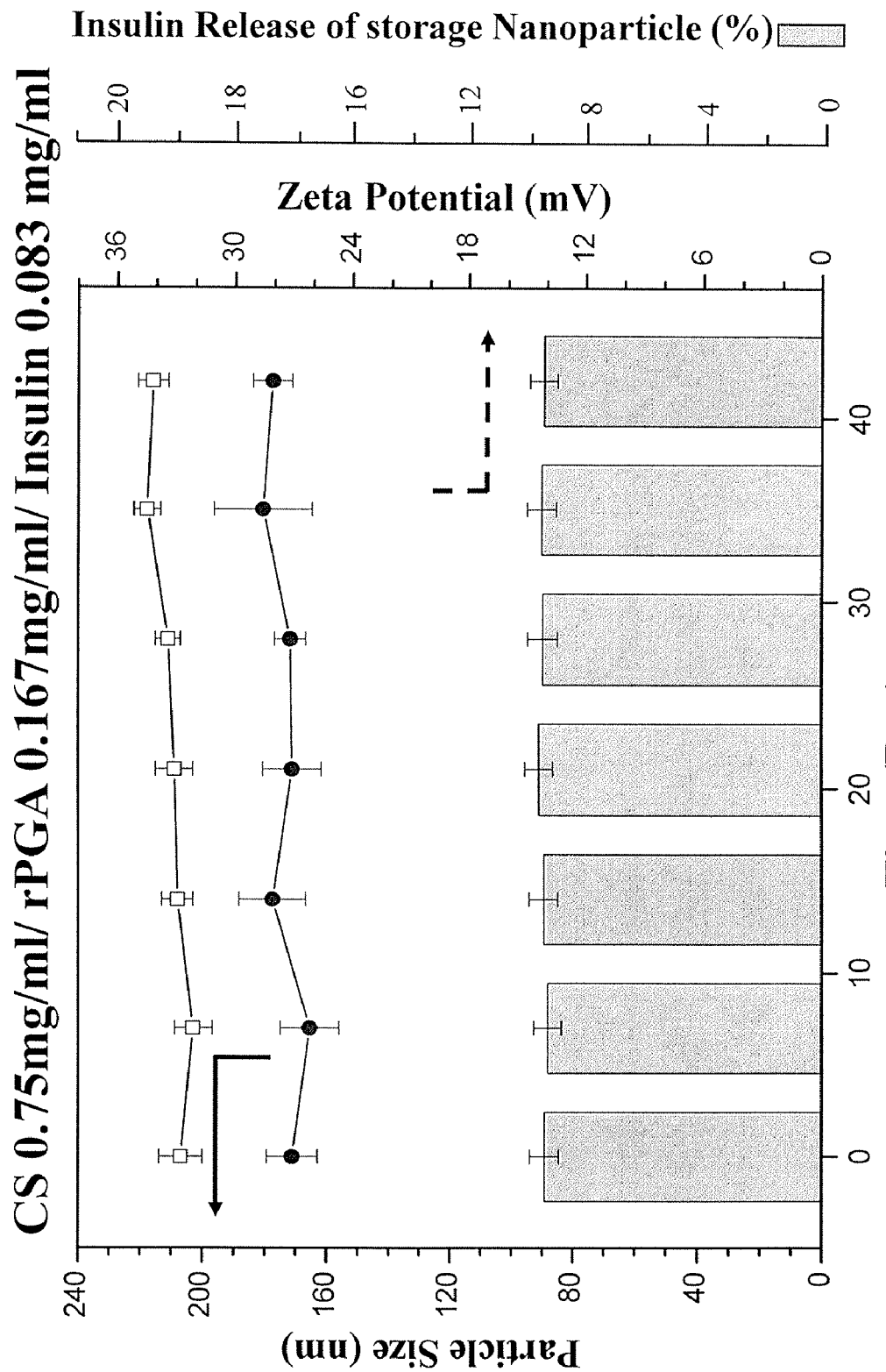
FIG. 13 shows the stability of insulin-loaded nanoparticles.

FIG. 13 shows the stability of insulin-loaded nanoparticles of the present invention with an exemplary composition of CS 0.75 mg/ml, γ-PGA 0.167 mg/ml, and insulin 0.083 mg/ml. The prepared insulin-loaded nanoparticles suspended in deionized water are stable during storage up to 40 days. First (in FIG. 13), the insulin content in the nanoparticle storage

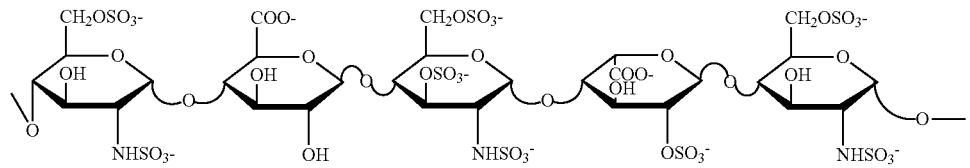

solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap or capsule configuration that further isolates the nanoparticles from environmental effects, such as sunlight, heat, air conditions, and the like. Some aspects of the invention provide a gelcap pill or capsule containing a dosage of insulin nanoparticles effective amount of the insulin to treat or manage the diabetic patients, wherein the stability of the insulin-containing nanoparticles is at least 40 days, preferably more than 6 months, and most preferably more than a couple of years.

By "effective amount of the insulin", it is meant that a sufficient amount of insulin will be present in the dose to provide for a desired therapeutic, prophylatic, or other biological effect when the compositions are administered to a host in the single dosage forms. The capsule of the present invention may preferably comprise two-part telescoping gelatin capsules. Basically, the capsules are made in two parts by dipping metal rods in molten gelatin solution. The capsules are supplied as closed units to the pharmaceutical manufacturer. Before use, the two halves are separated, the capsule is filled with powder (either by placing a compressed slug of powder into one half of the capsule, or by filling one half of the capsule with loose powder) and the other half of the capsule is pressed on. The advantage of inserting a slug of compressed powder is that control of weight variation is better. The capsules may be enterically coated before filling the powder or after filling the powder and securing both parts together.

Thus, for convenient and effective oral administration, pharmaceutically effective amounts of the nanoparticles of this invention can be tabletted with one or more excipient, encased in capsules such as gel capsules, and suspended in a liquid solution and the like. In one embodiment, the capsules further comprise a pharmaceutically acceptable carrier, diluent, or excipient, wherein the excipient may comprise a solubilizer, bubbling agent, or emulsifier. A bubbling agent is a compound that generates gas upon contacting with liquid, such as sodium bicarbonate plus citric acid powder or Ac-Di-Sol. The nanoparticles can be suspended in a deionized solution or the like for parenteral administration. The nanoparticles may be formed into a packed mass for ingestion by conventional techniques. For instance, the nanoparticles may be encapsulated as a "hard-filled capsule" or a "soft-elastic capsule" using known encapsulating procedures and materials. The encapsulating material should be highly soluble in gastric fluid so that the particles are rapidly dispersed in the stomach after the capsule is ingested. Each unit dose, whether capsule or tablet, will preferably contain nanoparticles of a suitable size and quantity that provides pharmaceutically effective amounts of the nanoparticles. The applicable shapes and sizes of capsules may include round, oval, oblong, tube or suppository shape with sizes from 0.75 mm to 80 mm or larger. The volume of the capsules can be from 0.05 cc to more than 5 cc. In one embodiment, the interior of capsules is treated to be hydrophobic or lipophilic.

Example No. 13

In Vitro Insulin Release Study

Figure 14:
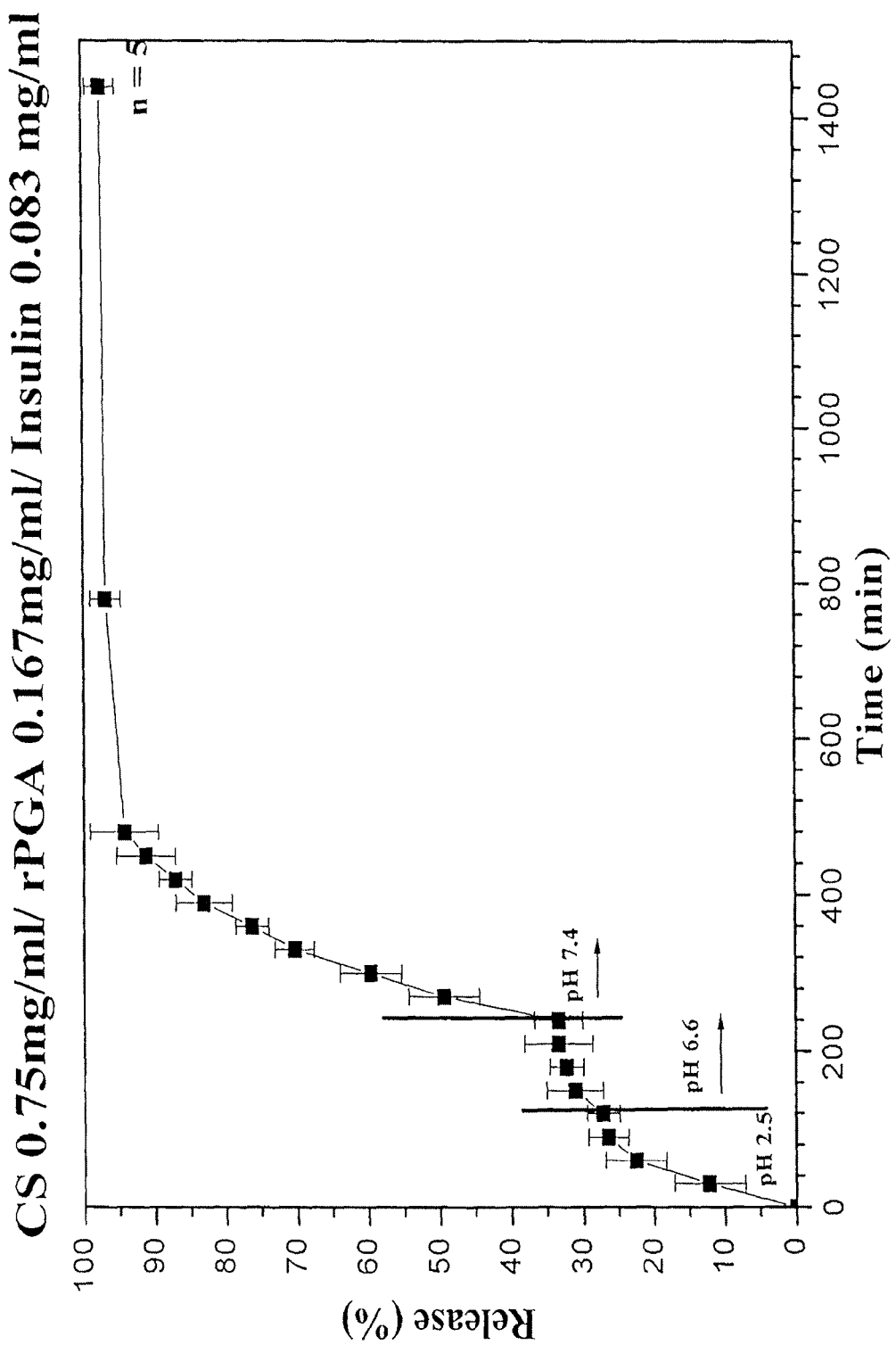
FIG. 14 shows a representative in vitro study with insulin drug release profile in a pH-adjusted solution.

FIG. 14 show a representative protein drug (for example, insulin) release profile in a pH-adjusted solution for pH-sensitivity study with an exemplary composition of CS 0.75 mg/ml, γ-PGA 0.167 mg/ml, and insulin 0.083 mg/ml in nanoparticles. In one embodiment, the exemplary composition may include each component at a concentration range of ±10% as follows: CS 0.75 mg/ml (a concentration range of 0.67 to 0.83 mg/ml), γ-PGA 0.167 mg/ml (a concentration range of 0.150 to 0.184 mg/ml), and insulin 0.083 mg/ml (a concentration range of 0.075 to 0.091 mg/ml). First, solution of the insulin-loaded nanoparticles was adjusted to pH 2.5 to simulate the gastric environment in a DISTEK-2230A container at 37° C. and 100 rpm. Samples (n=5) were taken at a pre-determined particular time interval and the particle-free solution was obtained by centrifuging at 22,000 rpm for 30 minutes to analyze the free or released insulin in solution by HPLC. Until the free insulin content in the sample solution approaches about constant of 26% (shown in FIG. 14), the pH was adjusted to 6.6 to simulate the entrance portion of the intestine. The net released insulin during this particular time interval is about (from 26% to 33%) 7%. In other words, the nanoparticles are quite stable (evidenced by minimal measurable insulin in solution) for both the pH 2.5 and pH 6.6 regions. To further simulate the exit portion of the intestine, the insulin-containing nanoparticle solution is adjusted to pH 7.4. The remaining insulin (about 67%) is released from the nanoparticles. As discussed above, the insulin in nanoparticles would be more effective to penetrate the intestine wall in paracellular transport mode than the free insulin because of the nanoparticles of the present invention with chitosan at the outer surface (preferential mucosal adhesion on the intestinal wall) and positive charge (enhancing paracellular tight junction transport).

Example No. 14

In Vivo Study with Insulin-Loaded Fluorescence-Labeled Nanoparticles

In the in vivo study, rats were injected with streptozotocin (STZ 75 mg/kg intraperitoneal) in 0.01M citrate buffer (pH 4.3) to induce diabetes rats. The blood from the rat's tail was analyzed with a commercially available glucometer for blood glucose. The blood glucose level on Wistar male rats at no fasting (n=5) is measured at 107.2±8.1 mg/dL for normal rats while the blood glucose level is at 469.7±34.2 mg/dL for diabetic rats. In the animal study, diabetic rats were fasting for 12 hours and subjected to four different conditions: (a) oral deionized water (DI) administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 15:
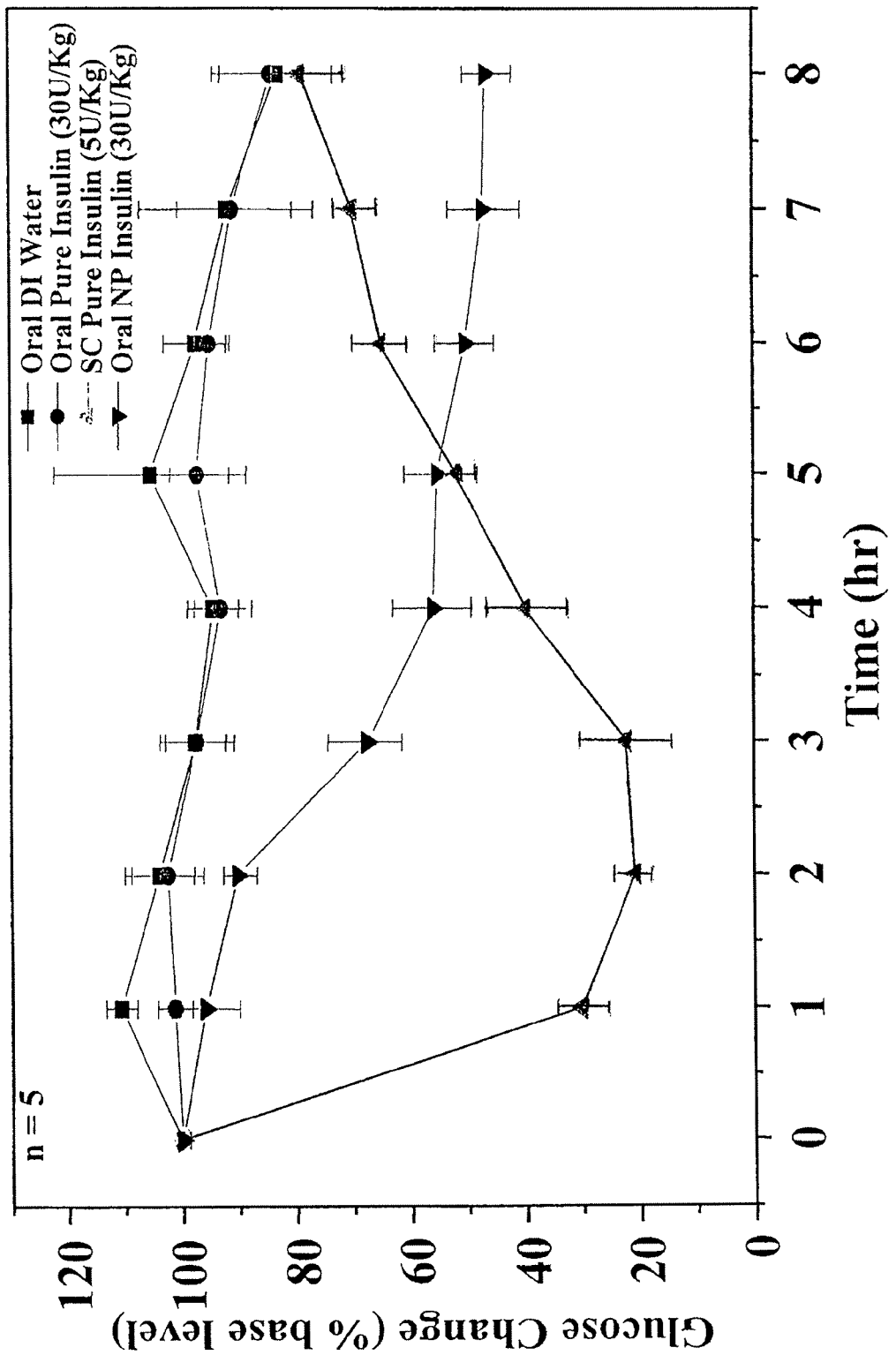
FIG. 15 shows the effect of insulin of orally administered insulin-loaded nanoparticles on hypoglycemia in diabetic rats.

FIG. 15 shows glucose change (hypoglycemic index) versus time of the in vivo animal study (n=5). The glucose change as a percentage of base lines for both oral DI administration and oral insulin administration over a time interval of 8 hours appears relatively constant within the experimental measurement error range. It is illustrative that substantially all insulin from the oral administration route has been decomposed in rat stomach. As anticipated, the glucose decrease for the SC insulin injection route appears in rat blood in the very early time interval and starts to taper off after 3 hours in this exemplary study. The most important observation of the study comes from the oral administration route with insulin-loaded nanoparticles.

The blood glucose begins to decrease from the base line at about 2 hours after administration and sustains at a lower glucose level at more than 8 hours into study. It implies that the current insulin-loaded nanoparticles may modulate the glucose level in animals in a sustained or prolonged effective mode. Some aspects of the invention provide a method of treating diabetes of a patient comprising orally administering insulin-containing nanoparticles with a dosage effective amount of the insulin to treat the diabetes, wherein at least a portion of the nanoparticles comprises a positively charged shell substrate and a negatively charged core substrate. In one embodiment, the dosage effective amount of the insulin to treat the diabetes comprises an insulin amount of between about 15 units to 45 units per kilogram body weight of the patient, preferably 20 to 40 units, and most preferably at about 25 to 35 units insulin per kilogram body weight.

Some aspects of the invention relate to a novel nanoparticle system that is composed of a low-MW CS and γ-PGA with CS dominated on the surfaces being configured to effectively open the tight junctions between Caco-2 cell monolayers. The surface of the nanoparticles is characterized with a positive surface charge. In one embodiment, the nanoparticles of the invention enables effective intestinal delivery for bioactive agent, including peptide, polypeptide, protein drugs, other large hydrophilic molecules, and the like. Such polypeptide drugs can be any natural or synthetic polypeptide that may be orally administered to a human patient.

Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds.

The bioactive agent of the present invention may also be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines.

In another embodiment, the nanoparticles of the invention increase the absorption of bioactive agents across the blood-brain barrier and/or the gastrointestinal barrier. In still another embodiment, the nanoparticles with chitosan at an outer layer and surface positive charge serve as an enhancer in enhancing paracellular drug (bioactive agent) transport of an administered bioactive agent when the bioactive agent and nanoparticles are orally administered in a two-component system, or orally administered substantially simultaneously.

Example No. 15

Paracellular Transport and Enhancers

Chitosan and its derivatives may function as intestinal absorption enhancers (that is, paracellular transport enhancers). Chitosan, when protonated at an acidic pH, is able to increase the paracellular permeability of peptide drugs across mucosal epithelia. Some aspects of the invention provide co-administration of nanoparticles of the present invention and at least one paracellular transport enhancer (in non-nanoparticle form or nanoparticle form). In one embodiment, the nanoparticles can be formulated by co-encapsulation of the at least one paracellular transport enhancer and at least one bioactive agent, optionally with other components. In one embodiment, the nanoparticles further comprise at least one permeation enhancer. The enhancer may be selected from the group consisting of $Ca^{2+}$ chelators, EDTA (ethylenediaminetetraacetic acid), bile salts, anionic surfactants, medium-chain fatty acids, phosphate esters, and chitosan or chitosan derivatives. EDTA refers to the chelating agent with the formula $(HO_2CCH_2)_2NCH_2CH_2N(CH_2CO_2H)_2$. It is approved by the FDA as a preservative in packaged foods, vitamins, and baby food. In one embodiment, the nanoparticles of the present invention comprises a positively charged shell substrate and a negatively charged core substrate, for example, nanoparticles composed of γ-PGA and chitosan that is characterized with a substantially positive surface charge.

In some embodiment, the nanoparticles or particulate complexes of the present invention and optionally the at least one paracellular transport enhancer are encapsulated in a soft gel, pill, enteric coated pill, enteric coated tablet, or enteric coated capsule. The enhancers and the nanoparticles would arrive at the tight junction about the same time for enhancing opening the tight junction. In another embodiment, the at least one paracellular transport enhancer is co-enclosed within the shell of the nanoparticles of the present invention. Therefore, some broken nanoparticles would release enhancers to assist the nanoparticles to open the tight junctions of the epithelial layers. In an alternate embodiment, the at least one enhancer is enclosed within a second nanoparticle having positive surface charges, particularly a chitosan type nanoparticle. When the drug-containing first nanoparticles of the present invention are co-administered with the above-identified second nanoparticles orally, the enhancers within the second nanoparticles are released in the intestinal tract to assist the drug-containing first nanoparticles to open and pass the tight junction.

Example No. 16

Nanoparticles with Exenatide

Exenatide is a member of the class of drugs known as incretin mimetics. Exenatide and pramlintide belong to non-insulin injectables for treatment of diabetes. Exenatide has a molecular formula of $C_{184}H_{282}N_{50}O_{60}S$ with a molecular mass of about 4186.6 g/mol and an CAS no. 141732-76-5. Exenatide is suitable to be incorporated in a core portion of chitosan-shelled nanoparticles, wherein the core portion may include positively charged chitosan and negatively charged core substrate, such as γ-PGA or α-PGA, optionally with additional TPP and $MgSO_4$ in the core portion. In preparation, nanoparticles were obtained upon addition of a mixture of γ-PGA plus exenatide aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Exenatide is wholly or substantially totally encapsulated in the core portion of the nanoparticles. Supernatants were discarded and nanoparticles were resuspended in deionized water as the solution products. In one embodiment, it may further be encapsulated in capsules. In one embodiment, the interior surface of the capsule is treated to be lipophilic or hydrophobic. In another embodiment, the exterior surface of the capsule is enteric-coated. In a preferred embodiment, the nanoparticles are further freeze-dried, optionally being mixed with trehalose or with hexan-1,2,3,4,5,6-hexyl in a freeze-drying process.

Glucagon-like peptide-1 (GLP-1) is derived from the transcription product of the proglucagon gene. The major source of GLP-1 in the body is the intestinal L cell that secretes GLP-1 as a gut hormone. The biologically active forms of GLP-1 are GLP-1-(7-37) and GLP-1-(7-36)$NH_2$. GLP-1 secretion by L cells is dependent on the presence of nutrients in the lumen of the small intestine. The secretagogues (agents that cause or stimulate secretion) of this hormone include major nutrients like carbohydrate, protein and lipid. Once in the circulation, GLP-1 has a half-life of less than 2 minutes, due to rapid degradation by the enzyme dipeptidyl peptidase-4 (DPP-4). Commercial GLP-1 ELISA kits are generally available for GLP-1 assay.

Exenatide (marketed as Byetta) is the first of a new class of medications (incretin mimetics) approved for the treatment of type 2 diabetes. It is manufactured and marketed by Amylin Pharmaceuticals and Eli Lilly and Company. Exenatide is a synthetic version of exendin-4, a hormone in the saliva of the Gila monster, a lizard native to several Southwestern American states. It displays properties similar to human GLP-1. Exenatide is a 39-amino-acid peptide that mimics the GLP-1 incretin, an insulin secretagogue with glucoregulatory effects. While it may lower blood glucose levels on its own, it can also be combined with other medications such as pioglitazone, metformin, sulfonylureas, and/or insulin (not FDA approved yet) to improve glucose control. The approved use of exenatide is with either sulfonylureas, metformin or thiazolinediones. The medication is injected subcutaneously twice per day using a pre-filled pen device.

Typical human responses to exenatide include improvements in the initial rapid release of endogenous insulin, suppression of pancreatic glucagon release, delayed gastric emptying, and reduced appetite—all of which function to lower blood glucose. Whereas some other classes of diabetes drugs such as sulfonylureas, thiazolinediones, and insulin are often associated with weight gain, Byetta often is associated with significant weight loss. Unlike sulfonylureas and meglitinides, exenatide increases insulin synthesis and secretion in the presence of glucose only, lessening the risk of hypoglycemia. Byetta is also being used by some physicians to treat insulin resistance.

Example No. 17

Nanoparticles with Pramlintide

Pramlintide is a synthetic amylin analogue (marketed as Symlin). Amylin is a natural, pancreatic islet peptide that is normally secreted with insulin in response to meals. It has several beneficial effects on glucose homeostasis: suppression of glucagon secretion, delaying of gastric emptying, and the promotion of satiety. It is currently given before meals, in a separate subcutaneous injection but usually in conjunction with insulin. Pramlintide has a molecular formula of $C_{171}H_{269}N_{51}O_{53}S_2$ with a molecular mass of about 3951.4 g/mol and an CAS no. 151126-32-8. Pramlintide (positively charged) is currently delivered as an acetate salt. Pramlintide is suitable to be incorporated in a core portion of a chitosan-shelled nanoparticles, wherein the core portion may include positively charged chitosan and negatively charged core substrate, such as γ-PGA or α-PGA, optionally with additional TPP and $MgSO_4$ in the core portion. In other words, pramlintide may replace at least a portion of positively charged chitosan in the core portion by interacting with negatively core substrate, such as PGA, heparin or the like. In preparation, nanoparticles were obtained upon addition of a mixture of γ-PGA plus pramlintide aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Pramlintide is wholly or substantially totally encapsulated in the core portion of the nanoparticles. Supernatants were discarded and nanoparticles were resuspended in deionized water as the solution products. In one embodiment, it may further be encapsulated in capsules. In one embodiment, the interior surface of the capsule is treated to be lipophilic or hydrophobic. In another embodiment, the exterior surface of the capsule is enteric-coated. In a preferred embodiment, the nanoparticles are further freeze-dried, optionally being mixed with trehalose or with hexan-1,2,3,4,5,6-hexyl in a freeze-drying process.

Pramlintide is an analogue of amylin, a small peptide hormone that is released into the bloodstream by the β-cells of the pancreas along with insulin, after a meal. Like insulin, amylin is deficient in individuals with diabetes. By augmenting endogenous amylin, pramlintide aids in the absorption of glucose by slowing gastric emptying, promoting satiety via hypothalamic receptors (different receptors than for GLP-1), and inhibiting inappropriate secretion of glucagon, a catabolic hormone that opposes the effects of insulin and amylin.

Example No. 18

Nanoparticles with Complexed Calcitonin

Calcitonin is a protein drug that serves therapeutically as calcium regulators for treating osteoporosis (J. Pharm. Pharmacol. 1994; 46:547-552). Calcitonin has a molecular formula of $C_{145}H_{240}N_{44}O_{48}S_2$ with a molecular weight of about 3431.9 and an isoelectric point of 8.7. The net charge for calcitonin at pH7.4 is positive that is suitable to complex or conjugate with negatively charged core substrate, such as γ-PGA or α-PGA. In preparation, nanoparticles were obtained upon addition of a mixture of γ-PGA plus calcitonin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Calcitonin is wholly or substantially totally encapsulated in the core portion of the nanoparticles. Supernatants were discarded and nanoparticles were resuspended in deionized water as the solution products, further encapsulated in capsules or further treated with an enteric coating.

Example No. 19

Nanoparticles with Conjugated Vancomycin

Vancomycin is a protein drug that serves therapeutically as antibiotic against bacterial pathogens. Vancomycin has a molecular formula of $C_{66}H_{75}N_9O_{24}$ with a molecular weight of about 1485.7 and an isoelectric point of 5.0. The net charge for vancomycin at pH7.4 is negative that is suitable to complex or conjugate with a portion of negatively charged shell substrate, such as chitosan. In preparation, nanoparticles were obtained upon addition of a mixture of γ-PGA plus vancomycin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature, wherein CS concentration is provided sufficiently to conjugate vancomycin, to counterbalance γ-PGA, and exhibit positive surface charge for the nanoparticles. Nanoparticles were collected by ultracentrifugation at 38,000 rpm for 1 hour. Vancomycin is wholly or substantially totally encapsulated in the core portion of the nanoparticles. Supernatants were discarded and nanoparticles were resuspended in deionized water as the solution products, further encapsulated in capsules or further treated with an enteric coating on capsules.

Some aspects of the invention relate to a method of enhancing intestinal or blood brain paracellular transport of bioactive agents configured and adapted for delivering at least one bioactive agent in a patient comprising administering nanoparticles composed of γ-PGA and chitosan, wherein the nanoparticles are loaded with a therapeutically effective amount or dose of the at least one bioactive agent. The nanoparticle of the present invention is an effective intestinal delivery system for peptide and protein drugs and other large hydrophilic molecules. In a further embodiment, the bioactive agent is selected from the group consisting of proteins, peptides, nucleosides, nucleotides, antiviral agents, antineoplastic agents, antibiotics, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL2), interferon, colony stimulating factor (CSF), tumor necrosis factor (TNF) and melanocyte-stimulating hormone. In a further embodiment, the bioactive agent is an Alzheimer antagonist.

Example No. 20

Nanoparticles with Heparin Core Substrate

Heparin is a negatively charged drug that serves therapeutically as anti-coagulant. Heparin is generally administered by intravenous injection. Some aspects of the invention relate to heparin nanoparticles for oral administration or subcutaneous administration. In a further embodiment, heparin serves as at least a portion of the core substrate with chitosan as shell substrate, wherein heparin conjugate at least one bioactive agent as disclosed herein. In preparation, nanoparticles were obtained upon addition of heparin Leo aqueous solution (2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature. Nanoparticles were collected by ultracentrifugation at 38,000 rpm for 1 hour. Heparin is wholly or substantially totally encapsulated in the core portion of the nanoparticles. Table 4 shows the conditions of solution preparation and the average nanoparticle size.

TABLE 4

| Conditions | Heparin conc. @ 2 ml | Chitosan conc. @ 10 ml | Particle size (nm) |
| --- | --- | --- | --- |
| A | 200 iu/ml | 0.09% | 298.2 ± 9.3 |
| B | 100 iu/ml | 0.09% | 229.1 ± 4.5 |

TABLE 4-continued

| Conditions | Heparin conc. @ 2 ml | Chitosan conc. @ 10 ml | Particle size (nm) |
| --- | --- | --- | --- |
| C | 50 iu/ml | 0.09% | 168.6 ± 1.7 |
| D | 25 iu/ml | 0.09% | 140.1 ± 2.3 |

To evaluate the pH stability of the heparin-containing nanoparticles from Example no. 20, the nanoparticles from Condition D in Table 4 are subjected to various pH for 2 hours (sample size=7). Table 5 shows the average size, size distribution (polydispersity index: PI) and zeta potential (Zeta) of the nanoparticles at the end of 2 hours under various pH environments. The data shows the nanoparticles are relatively stable. In one embodiment, the nanoparticles of the present invention may include heparin, heparin sulfate, small molecular weight heparin, and heparin derivatives.

TABLE 5

| pH | 1.5 | 2.6 | 6.6 | 7.4 | Deionized water @ 5.9 |
| --- | --- | --- | --- | --- | --- |
| Size (nm) | 150 ± 9 | 160 ± 12 | 153 ± 2 | 154 ± 4 | 147 ± 5 |
| PI | 0.54 ± 0.03 | 0.50 ± 0.04 | 0.08 ± 0.02 | 0.32 ± 0.03 | 0.37 ± 0.02 |
| Zeta (+) | 15 ± 2 | 33 ± 6 | 15 ± 0.1 | 11 ± 0.2 | 18 ± 4 |

In a further embodiment, a growth factor such as bFGF with pharmaceutically effective amount is added to heparin Leo aqueous solution before the pipetting step in Example No. 20. In our laboratory, growth factors and proteins with pharmaceutically effective amount have been successfully conjugated with heparin to form nanoparticles of the present invention with chitosan as the shell substrate, wherein the growth factor is selected from the group consisting of Vascular Endothelial Growth Factor (VEGF), Vascular Endothelial Growth Factor 2 (VEGF2), basic Fibroblast Growth Factor (bFGF), Vascular Endothelial Growth Factor 121 (VEGF121), Vascular Endothelial Growth Factor 165 (VEGF165), Vascular Endothelial Growth Factor 189 (VEGF189), Vascular Endothelial Growth Factor 206 (VEGF206), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PD-WHF), epidermal growth factor, insulin-like growth factor, acidic Fibroblast Growth Factor (aFGF), human growth factor, and combinations thereof; and the protein is selected from the group consisting of haemagglutinin (HBHA), Pleiotrophin, buffalo seminal plasma proteins, and combinations thereof.

In a co-pending application, U.S. patent application Ser. No. 10/916,170 filed Aug. 11, 2004, it is disclosed that a biomaterial with free amino groups of lysine, hydroxylysine, or arginine residues within biologic tissues is crosslinkable with genipin, a crosslinker (Biomaterials 1999; 20:1759-72). It is also disclosed that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC(N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release.

By modifying the chitosan structure to alter its charge characteristics, such as grafting the chitosan with methyl, N-trimethyl, alkyl (for example, ethyl, propyl, butyl, isobutyl, etc.), polyethylene glycol (PEG), or heparin (including low molecular weight heparin, regular molecular weight heparin, and genetically modified heparin), the surface charge density (zeta potential) of the CS-γ PGA nanoparticles may become more pH resistant or hydrophilic. In one embodiment, the chitosan is grafted with polyacrylic acid.

By way of illustration, trimethyl chitosan chloride might be used in formulating the CS-γ PGA nanoparticles for maintaining its spherical biostability at a pH lower than pH 2.5, preferably at a pH as low as 1.0. Some aspects of the invention provide a drug-loaded chitosan-containing biological material crosslinked with genipin or other crosslinking agent as a biocompatible drug carrier for enhancing biostability at a pH lower than pH 2.5, preferably within at a pH as low as 1.0.

Freeze-Dried Nanoparticles

A pharmaceutical composition of nanoparticles of the present invention may comprise a first component of at least one bioactive agent, a second component of chitosan (including regular molecular weight and low molecular weight chitosan), and a third component that is negatively charged. In one embodiment, the second component dominates on a surface of the nanoparticle. In another embodiment, the chitosan is N-trimethyl chitosan. In still another embodiment, the low molecular weight chitosan has a molecular weight lower than that of a regular molecular weight chitosan. The nanoparticles may further comprise tripolyphosphate and magnesium sulfate. For example, a first solution of (2 ml 0.1% γ-PGA aqueous solution @pH 7.4+0.05% Insulin+0.1% Tripolyphosphate (TPP)+0.2% MgSO4) is added to a base solution (10 ml 0.12% chitosan aqueous solution @pH 6.0) as illustrated in Example no. 4 under magnetic stirring at room temperature. Nanoparticles were collected by ultracentrifugation at 38,000 rpm for 1 hour. The bioactive agent, the third component, tripolyphosphate and magnesium sulfate are wholly or substantially totally encapsulated in the core portion of the nanoparticles. Supernatants were discarded and nanoparticles were resuspended in deionized water for freeze-drying preparation. Other operating conditions or other bioactive agent (such as protein, peptide, siRNA, growth factor, the one defined and disclosed herein, and the like) may also apply.

Several conventional coating compounds that form a protective layer on particles are used to physically coat or mix with the nanoparticles before a freeze-drying process. The coating compounds may include trehalose, mannitol, glycerol, and the like. Trehalose, also known as mycose, is an alpha-linked (disaccharide) sugar found extensively but not abundantly in nature. It can be synthesized by fungi, plants and invertebrate animals. It is implicated in anhydrobiosis—the ability of plants and animals to withstand prolonged periods of desiccation. The sugar is thought to form a gel phase as cells dehydrate, which prevents disruption of internal cell organelles by effectively splinting them in position. Rehydration then allows normal cellular activity to resume without the major, generally lethal damage, which would normally follow a dehydration/rehydration cycle. Trehalose has the added advantage of being an antioxidant.

Trehaloze has a chemical formula as $C_{12}H_{22}O_{11}.2H_2O$. It is listed as CAS no. 99-20-7 and PubChem 7427. The molecular structure for trehalose is shown below.

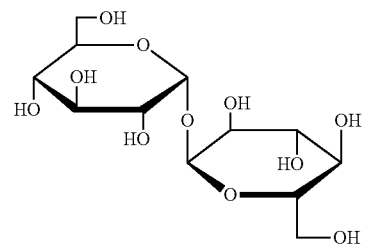

Trehalose was first isolated from ergot of rye. Trehalose is a non-reducing sugar formed from two glucose units joined by a 1-1 alpha bond giving it the name of α-D-glucopyranosyl-(1→1)-α-D-glucopyranoside. The bonding makes trehalose very resistant to acid hydrolysis, and therefore stable in solution at high temperatures even under acidic conditions. The bonding also keeps non-reducing sugars in closed-ring form, such that the aldehyde or ketone end-groups do not bind to the lysine or arginine residues of proteins (a process called glycation). Trehalose has about 45% the sweetness of sucrose. Trehalose is less soluble than sucrose, except at high temperatures (>80° C.). Trehalose forms a rhomboid crystal as the dihydrate, and has 90% of the calorific content of sucrose in that form. Anhydrous forms of trehalose readily regain moisture to form the dihydrate. Trehalose has also been used in at least one biopharmaceutical formulation, the monoclonal antibody trastuzumab, marketed as Herceptin. It has a solubility of 68.9 g/100 g $H_2O$ at 20° C.

Mannitol or hexan-1,2,3,4,5,6-hexyl $(C_6H_8(OH)_6)$ is an osmotic diuretic agent and a weak renal vasodilator. Chemically, mannitol is a sugar alcohol, or a polyol; it is similar to xylitol or sorbitol. However, mannitol has a tendency to lose a hydrogen ion in aqueous solutions, which causes the solution to become acidic. For this, it is not uncommon to add a substance to adjust its pH, such as sodium bicarbonate. Mannitol has a chemical formula as $C_6H_{14}O_6$. It is listed as CAS no. 69-65-8 and PubChem 453. The molecular structure for mannitol is shown below.

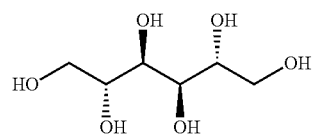

Glycerol is a chemical compound with the formula HOCH₂CH(OH)CH₂OH. This colorless, odorless, viscous liquid is widely used in pharmaceutical formulations. Also commonly called glycerin or glycerine, it is a sugar alcohol and fittingly is sweet-tasting and of low toxicity. Glycerol has three hydrophilic alcoholic hydroxyl groups that are responsible for its solubility in water and its hygroscopic nature. Glycerol has a chemical formula as $C_3H_5(OH)_3$. It is listed as CAS no. 56-81-5. The molecular structure for glycerol is shown below.

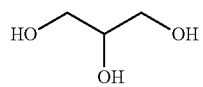

Example No. 21

Freeze-Drying Process for Nanoparticles

Nanoparticles (at 2.5% concentration) were mixed with solution from four types of liquid at a 1:1 volume ratio for about 30 minutes until fully dispersed. The mixed particle-liquid was then freeze-dried under a lyophilization condition, for example, at about −80° C. and <25 mmHg pressure for about 6 hours. The parameters in a selected lyophilization condition may vary slightly from the aforementioned numbers. The four types of liquid used in the experiment include: (A) DI water; (B) trehalose; (C) mannitol; and (D) glycerol, whereas the concentration of the liquid (A) to liquid (C) in the solution was set at 2.5%, 5% and/or 10%. After a freeze-drying process, the mixed particle-liquid was rehydrated with DI water at a 1:5 volume ratio to assess the integrity of nanoparticles in each type of liquid. The results are shown in Table 6. By comparing the particle size, polydispersity index and zeta-potential data, only the nanoparticles from the freeze-dried particle-trehalose runs (at 2.5%, 5%, and 10% concentration level) show comparable properties as compared to those of the before-lyophilization nanoparticles. Under the same data analysis, the nanoparticles from the freeze-dried particle-mannitol runs (at 2.5%, and 5% concentration level) show somewhat comparable properties as compared to those of the before-lyophilization nanoparticles.

TABLE 6

Properties of nanoparticles before and after an exemplary freeze-drying process.

| | | A: DI Water | | |
|---|---|---|---|---|
| NPs solution | | A:DI water + NPs (volume 1:1), freeze-dried | | |
| Conc. | 2.50% | Conc. | | |
| Size (nm) | 266 | Size (nm) | | 9229.1 |
| Kcps | 352.2 | Kcps | | 465.3 |
| PI | 0.291 | PI | | 1 |
| Zeta Potential | 25.3 | Zeta Potential | | |
| | | B: Trehalose | | |
| B:Trehalose + NPs (volume 1:1), freeze-dried | | | | |
| Conc. | 2.50% | | 5.00% | 10.00% |
| Size (nm) | 302.4 | | 316.7 | 318.9 |
| Kcps | 363.7 | | 327.7 | 352.2 |
| PI | 0.361 | | 0.311 | 0.266 |
| Zeta Potential | 25.6 | | 24.6 | 24.7 |

TABLE 6-continued

Properties of nanoparticles before and after an exemplary freeze-drying process.

| C: Mannitol | | | |
|---|---|---|---|
| C: Mannitol + NPs (volume 1:1), freeze-dried | | | |
| Conc. | 2.50% | | 5.00% |
| Size (nm) | 420.1 | | 487.5 |
| Kcps | 305.4 | | 303.7 |
| PI | 0.467 | | 0.651 |
| Zeta Potential | 24.4 | | 25.3 |
| D: Glycerol | | | |
| D: Glycerol + NPs (volume 1:1), freeze-dried | | | |
| Conc. | 2.50% | 5.00% | 10.00% |
| Size (nm) | 6449.1 | 7790.3 | 1310.5 |
| Kcps | 796.1 | 356.1 | 493.3 |
| PI | 1 | 1 | 1 |
| Zeta Potential | | | |

Figure 16:
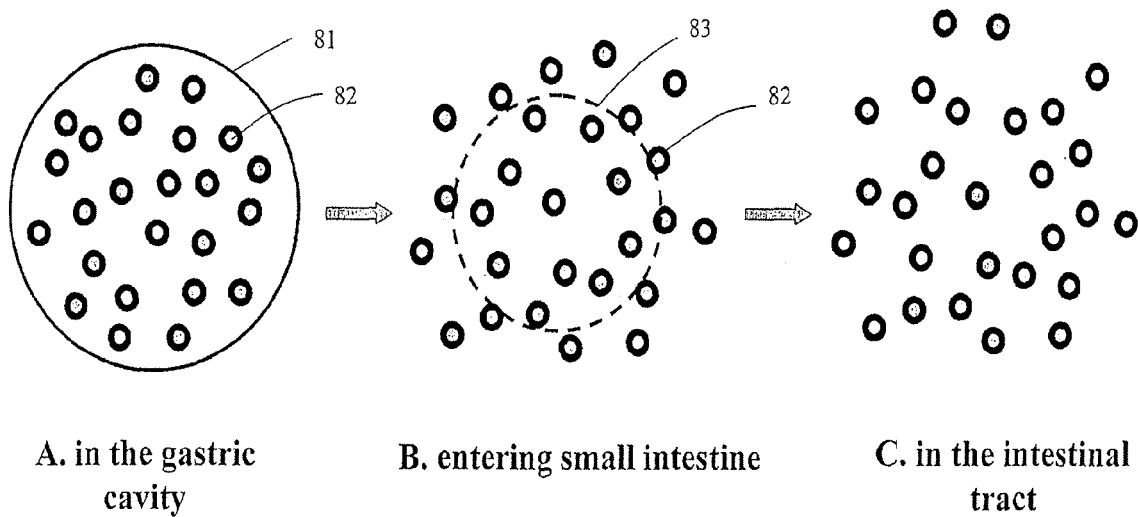
FIGS. 16A-C show a proposed mechanism of nanoparticles released from the enteric coated capsules.

FIG. 16 shows an illustrative mechanism of nanoparticles released from the enteric-coated capsules. FIG. 16(A) shows the phase of nanoparticles in the gastric cavity, wherein the freeze-dried nanoparticles 82 are encapsulated within an initial enteric coating or coated capsule 81. FIG. 16(B) shows a schematic of the nanoparticles during the phase of entering small intestine, wherein the enteric coat and its associated capsule starts to dissolve 83 and a portion of nanoparticles 82 is released from the capsule and contacts fluid. FIG. 16(C) shows the phase of nanoparticles in the intestinal tract, wherein the nanoparticles revert to a wet state having chitosan at its surface. In an alternate embodiment, nanoparticles may be released from alginate-calcium coating. In preparation, nanoparticles are first suspended in a solution that contains calcium chloride, wherein the calcium ions are positively charged. With a pipette, alginate with negatively charged carboxyl groups is slowly added to the calcium chloride solution. Under gentle stirring, the alginate-calcium starts to conjugate, gel, and coat on the nanoparticle surface. In simulated oral administration of the alginate-calcium coated nanoparticles, nanoparticles start to separate from the coating when they enter the small intestines.

Example No. 22

Freeze-Dried Nanoparticles in Animal Evaluation

In the in vivo study, rats as prepared and conditioned according to Example no. 14 were used in this evaluation. In the animal evaluation study, diabetic rats were fasting for 12 hours and subjected to three different conditions: (a) oral deionized water (DI) administration as negative control; (b) oral insulin-loaded lyophilized nanoparticles administration, whereas the nanoparticles have an insulin loading content of at least 4.4% and an insulin loading efficiency of at least 48.6% and are loaded in a capsule with surface enteric coating; and (c) subcutaneous (SC) insulin injection at 5 U/kg as positive control. The blood glucose concentration from rat's tail was measured over the time in the study.

Figure 19:
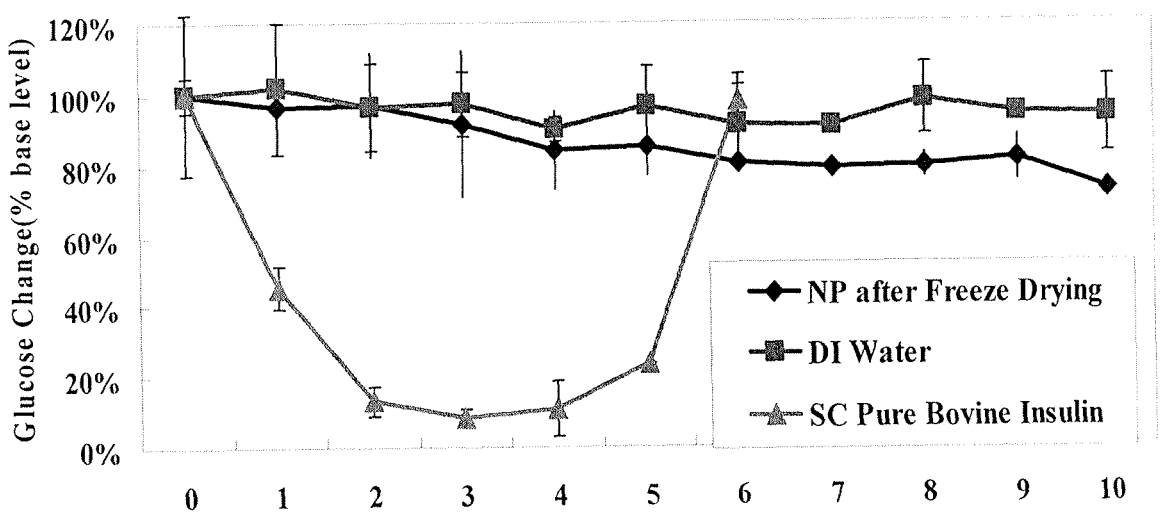
FIG. 19 shows the effect of orally administered insulin-loaded nanoparticles on 'glucose reduction %' in diabetic rats, wherein the freeze-dried nanoparticles were loaded in an enterically coated capsule upon delivery.

FIG. 19 shows glucose change (hypoglycemic index) versus time of the in vivo animal study (n=5). The glucose change as a percentage of base lines for oral DI administration (control) over a time interval of 10 hours appears relatively constant within the experimental measurement error range. As anticipated, the glucose decrease for the SC insulin injection route appears in rat blood in the very early time interval and starts to taper off after 2 hours in this exemplary study and ends at about 6 hours. The glucose decrease for the orally administered insulin-loaded NPs continued until the end of sampling time at 10 hours.

The blood glucose begins to decrease from the base line at about 3 hours after administration and sustains at a lower glucose level at more than 10 hours into study. It implies that the current insulin-loaded nanoparticles may modulate the glucose level in animals in a sustained or prolonged effective mode. Some aspects of the invention provide a method of treating diabetes of a patient comprising orally administering insulin-containing nanoparticles with a dosage effective amount of the insulin to treat the diabetes, wherein at least a portion of the nanoparticles comprises a positively charged shell substrate and a negatively charged core substrate. In one embodiment, the dosage effective amount of the insulin to treat the diabetes comprises an insulin amount of between about 15 units to 45 units per kilogram body weight of the patient, preferably 20 to 40 units, and most preferably at about 25 to 35 units insulin per kilogram body weight. In one embodiment, the lyophilized nanoparticles may be fed as is to an animal without being loaded in an enterically coated capsule.

It is known that Zn (zinc) is usually added in the biosynthesis and storage of insulin. Some aspects of the invention relate to a nanoparticle characterized by enhancing intestinal or blood brain paracellular transport, the nanoparticle comprising a first component of at least one bioactive agent, a second component of low molecular weight chitosan, and a third component that is negatively charged, wherein a stabilizer is added to complex the at least one bioactive agent to the negatively charged third component. In one embodiment, the stabilizer is zinc or calcium.

Example No. 23

Nanoparticles with Enhanced Insulin Loading

Figure 10:
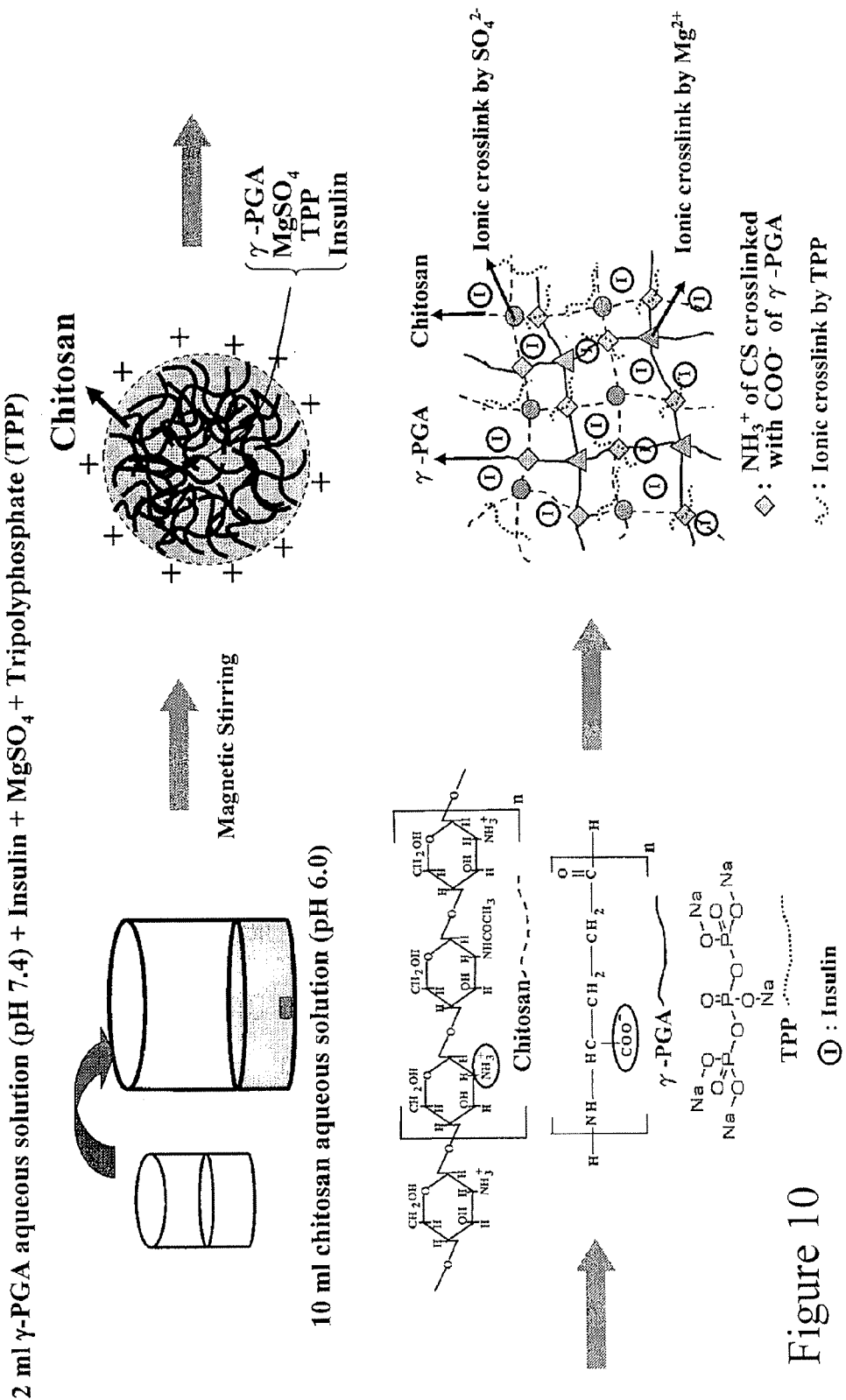
FIG. 10 shows insulin-loaded nanoparticles with a core composition consisted of γ-PGA, $MgSO_4$, sodium tripolyphosphate (TPP), and insulin.

Some aspects of the invention relate to a novel nanoparticle comprising a shell substrate of chitosan and a core substrate consisting of at least one bioactive agent, $MgSO_4$, TPP, and a negatively charged substrate that is neutralized with chitosan in the core. FIG. 10 shows insulin-loaded nanoparticles with a core composition comprised of γ-PGA, $MgSO_4$, sodium tripolyphosphate (TPP), and insulin. Nanoparticles were obtained upon addition of core component, using a pipette (0.5-5 ml, PLASTIBRAND®, BrandTech Scientific Inc., Germany), into a CS aqueous solution (pH 6.0, 10 ml) at certain concentrations under magnetic stirring at room temperature. Nanoparticles were collected by ultracentrifugation at 38,000 rpm for 1 hour. Supernatants were discarded and nanoparticles were resuspended in deionized water for further studies. In one embodiment, nanoparticles are encapsulated in a gelcap or are lyophilized before being loaded in a gelcap or in a tablet. The sodium tripolyphosphate has a chemical formula of $Na_5P_3O_{10}$ as shown below:

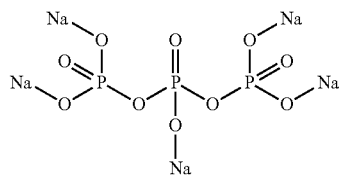

In the example, the core composition may be varied and evaluated with a preferred composition of 2 ml γ-PGA aqueous solution at pH 7.4 plus insulin, $MgSO_4$ and TPP, resulting in a ratio of CS:γ-PGA:TPP:MgSO4:insulin=6.0:1.0:1.0:2.0: 0.05. Thus, the nanoparticles show characteristics with chitosan shell and a core composition consisted of γ-PGA, $MgSO_4$, TPP, and insulin and have an average loading efficiency of 72.8% insulin and an average loading content of 21.6% insulin.

In the enhanced drug loading of the present example, there provides two or more distinct ionic crosslink mechanisms. In one embodiment, the nanoparticles of the present invention may have a structure or matrix of interpenetrated ionic-crosslinks (that is, elongate ionic-crosslink chains) including a first ionic-crosslink chain of $NH_3$ of CS with $COO^-$ of γ-PGA, a second ionic-crosslink chain of $NH_3^+$ of CS with $SO_4^{2-}$ of $MgSO_4$, a third ionic-crosslink chain of $Mg^{2+}$ of $MgSO_4$ with $COO^-$ of γ-PGA, and/or a fourth ionic-crosslink chain of $Na_3P_3O_{10}^{2-}$ of TPP with $NH_3^+$ of CS or $Mg^{2+}$ of $MgSO_4$.

Some aspects of the invention relate to a nanoparticle composition for oral administration with the insulin loading efficiency and content at higher than 45% and 14% (preferably up to about 73% and 22%), respectively. The prepared nanoparticles (NPs) are stable in the range of pH 2.0 to 7.1. This broad range is to maintain the chitosan-shelled nanoparticle and/or chitosan-shelled nanoparticulate fragments transiently stable in most of the intestine region (including duodenum, jejunum, and ileum) for enhanced membrane adsorption and paracellular permeability of active ingredient (for example, insulin, exenatide or pramlintide). Some aspects of the invention provide a chitosan-shelled nanoparticle with a core composition comprised of γ-PGA, $MgSO_4$, TPP, and at least one bioactive agent, such as insulin, exenatide or pramlintide for treatment of diabetes. In an alternate embodiment, some aspects of the invention provide a chitosan-shelled nanoparticle with a core composition consisted of γ-PGA, $MgSO_4$, TPP, and at least one bioactive agent. In one embodiment, negatively charged γ-PGA may conveniently be substituted by another negatively charge substrate, such as heparin. In an experiment following the experimental conditions of Example no. 23 by substituting insulin with exenatide, chitosan-shelled nanoparticles with a core composition comprised of γ-PGA, $MgSO_4$, TPP, and exenatide have been prepared that exhibit similar physical and mechanical properties as compared to the ones with insulin.

Figure 21:
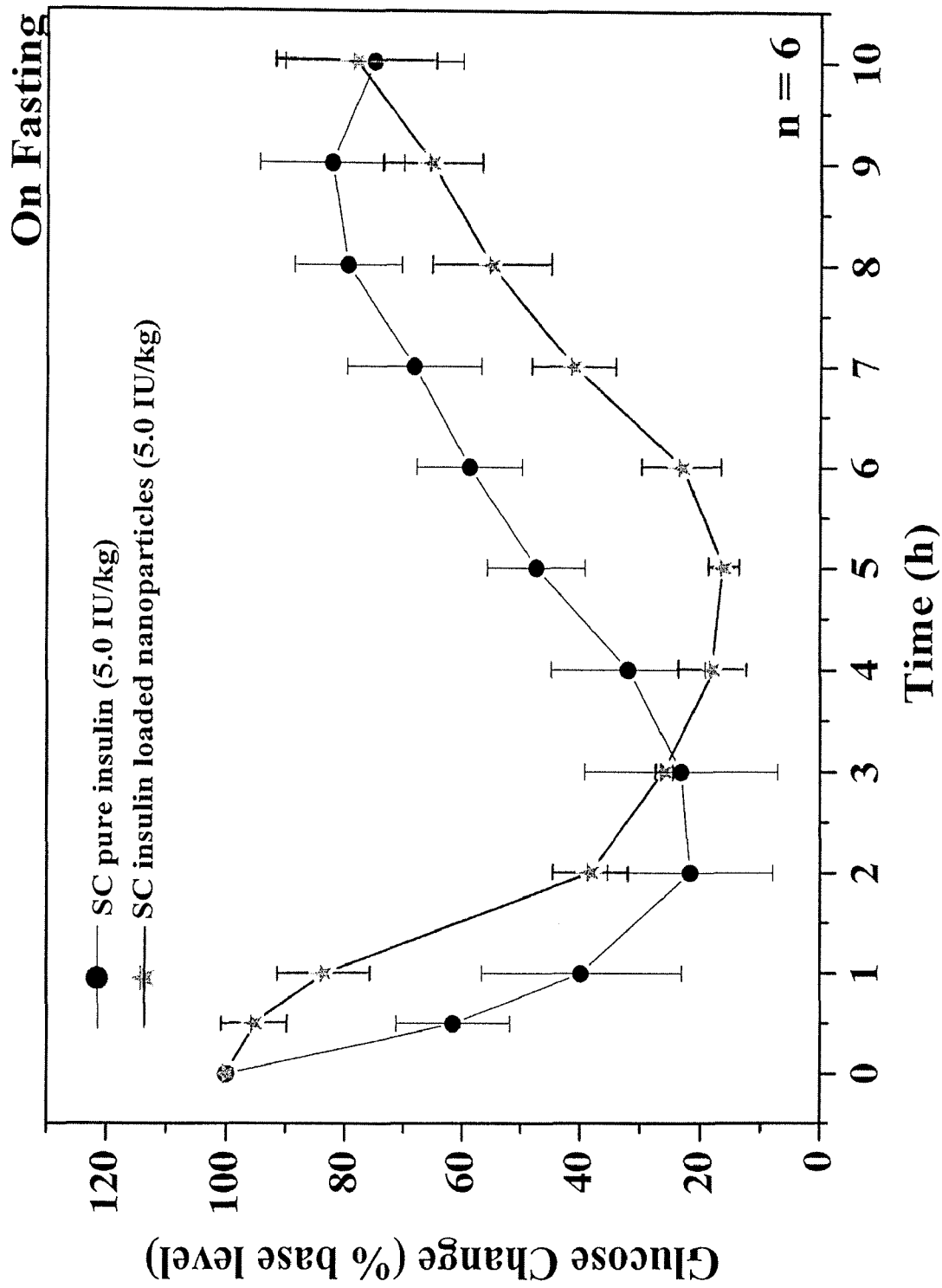
FIG. 21 shows an in vivo subcutaneous study using insulin injectables and insulin-containing nanoparticles.

FIG. 21 shows an in vivo subcutaneous study using insulin injectables and insulin-containing nanoparticles. The insulin-containing nanoparticles exhibit different pharmacodynamics and/or pharmacokinetics in a sustained releasing manner. Some aspects of the invention relate to a pharmaceutical composition of nanoparticles for subcutaneous or blood vessel administration in a patient, the nanoparticles comprising a shell portion that is dominated by positively charged chitosan, a core portion that contains negatively charged substrate, wherein the negatively charged substrate is at least partially neutralized with a portion of the positively charged chitosan in the core portion, and at least one bioactive agent loaded within the nanoparticles.

In one embodiment, the delivery route is via nasal instillation, buccal absorption, sublingual or oral absorption. In another embodiment, the delivery route is via endocytosis of chitosan-shelled nanoparticles or chitosan-shelled nanoparticulate fragments by the cells in a transcellular mode. Chitosan nanoparticles promoted cellular uptake of its cargo via endocytosis, a phenomenon not seen when chitosan was presented as a soluble solution (Pharmaceutical Research 2003; 20:1812-1819). In our lab, we have enabled endocytosis data with chitosan-shelled bioactive nanoparticles or fragments. Endocytosis is a process where cells absorb material (molecules such as proteins) from the outside by engulfing it with their cell membrane. It is used by all cells of the body because most substances important to them are large polar molecules, and thus cannot pass through the hydrophobic plasma membrane or cell membrane. The bioactive nanoparticle fragments herein are generally in the range of about 10 to 150 nm, preferably in the range of about 20 to 100 nm, and most preferably in the range of about 20 to 50 nm.

Some aspects of the invention relate to a method of delivering a bioactive agent to blood circulation in a patient, comprising: (a) providing nanoparticles according to a preferred embodiment of the pharmaceutical composition of the present invention, wherein the nanoparticles are formed via a simple and mild ionic-gelation method; (b) administering the nanoparticles orally toward the intestine of the patient via stomach; (c) urging the nanoparticles to be absorbed onto a surface of an epithelial membrane of the intestine via mucoadhesive chitosan-shelled nanoparticles; (d) permeating bioactive agent to pass through an epithelial barrier of the intestine; and (e) releasing the bioactive agent into the blood circulation. In one embodiment, the bioactive agent is selected from the group consisting of exenatide, pramlintide, insulin, insulin analog, and combinations thereof. In another embodiment, the bioactive agent permeates through the tight junctions of the epithelial membrane when chitosan-shelled nanoparticles break up and release the bioactive agent at vicinity of the tight junctions.

Some aspects of the invention relate to a method for inducing a redistribution of tight junction's ZO-1 protein, leading to translocation of the ZO-1 protein to cytoskeleton that accompanies increased paracellular transport in a patient, the method comprising administering into the patient bioactive nanoparticles with a dosage effective to induce the redistribution, wherein the bioactive nanoparticles comprise a shell substrate of chitosan and a core substrate that comprises poly(glutamic acid) and the bioactive agent that is selected from the group consisting of exenatide, pramlintide, insulin, insulin analog, and combinations thereof.

Blood-Brain Barrier and Tight Junctions

The blood-brain barrier (BBB) is a membrane structure in the central nervous system (CNS) that restricts the passage of various chemical substances and microscopic objects (e.g. bacteria) between the bloodstream and the neural tissue itself, while still allowing the passage of substances essential to metabolic function. This "barrier" results from the selectivity of the tight junctions between endothelial cells in CNS vessels that restricts the passage of solutes. At the interface between blood and brain, endothelial cells and associated astrocytes are joined together by structures called tight junctions. The tight junction is composed of smaller subunits, frequently dimers that are transmembrane proteins such as occludin, claudins, junctional adhesion molecule (JAM), ESAM and others. Each of these transmembrane proteins is anchored into the endothelial cells by another protein complex that includes ZO-1 and associated proteins. The blood-brain barrier is composed of high-density cells restricting passage of substances from the bloodstream much more than endothelial cells in capillaries elsewhere in the body.

Some diseases associated with the blood-brain barrier may include Meningitis, which is inflammation of the membranes that surround the brain and spinal cord (these membranes are also known as meninges). Meningitis is most commonly caused by infections with various pathogens, examples of which are *Staphylococcus aureus* and *Haemophilus influenza*. When the meninges are inflamed, the blood-brain barrier may be disrupted. This disruption may increase the penetration of various substances (including antibiotics) into the brain. Some aspects of the invention relate to a method for delivering therapeutic nanoparticles of the present invention incorporating meningitis antagonist or anti-inflammatory drugs as a bioactive agent to the tight junction of a brain-blood barrier site for treatment of meningitis.

Another disease associated with brain-blood barrier may be Epilepsy, which is a common neurological disease characterized by frequent and often untreatable seizures. Several clinical and experimental data have implicated failure of blood-brain barrier function in triggering chronic or acute seizures. These findings have shown that acute seizures are a predictable consequence of disruption of the BBB by either artificial or inflammatory mechanisms. In addition, expression of drug resistance molecules and transporters at the BBB are a significant mechanism of resistance to commonly used anti-epileptic drugs. Some aspects of the invention relate to a method for delivering therapeutic nanoparticles of the present invention incorporating anti-epileptic drugs or anti-inflammatory drugs/medicine as a bioactive agent to the tight junction of a brain-blood barrier site for treatment of epilepsy.

Another disease associated with brain-blood barrier is Multiple Sclerosis (MS), which is considered an auto-immune disorder in which the immune system attacks the myelin protecting the nerves in the central nervous system. Normally, a person's nervous system would be inaccessible for the white blood cells due to the blood-brain barrier. However, it has been shown using MRI (Magnetic Resonance Imaging) that, when a person is undergoing an MS "attack," the blood-brain barrier has broken down in a section of the brain or spinal cord, allowing white blood cells called T lymphocytes to cross over and destroy the myelin. It has been suggested that, rather than being a disease of the immune system, MS is a disease of the blood-brain barrier. It is believed that oxidative stress plays an important role into the breakdown of the barrier; anti-oxidants such as lipoic acid may be able to stabilize a weakening blood-brain barrier. Some aspects of the invention relate to a method for delivering therapeutic nanoparticles of the present invention incorporating anti-oxidants or anti-inflammatory medicine as a bioactive agent to the tight junction of a brain-blood barrier site for treatment of multiple sclerosis.

One disease associated with brain-blood barrier is Neuromyelitis optica, also known as Devic's disease, which is similar to and often confused with multiple sclerosis. Patients with neuromyelitis optica have high levels of antibodies against a protein called aquaporin-4. Some aspects of the invention relate to a method for delivering therapeutic nanoparticles of the present invention incorporating anti-neuromyelitis optica drugs or anti-inflammatory medicine as a bioactive agent to the tight junction of a brain-blood barrier site for treatment of Devic's disease.

One disease associated with brain-blood barrier is Late-stage neurological trypanosomiasis, or sleeping sickness, which is a condition in which *trypanosoma* protozoa are found in brain tissue. It is not yet known how the parasites infect the brain from the blood, but it is suspected that they cross through the choroid plexus, a circumventricular organ. Some aspects of the invention relate to a method for delivering therapeutic nanoparticles of the present invention incorporating anti-neurological trypanosomiasis drugs or anti-inflammatory medicine as a bioactive agent to the tight junction of a brain-blood barrier site for treatment of Late-stage neurological trypanosomiasis.

One disease associated with brain-blood barrier is Progressive multifocal leukoencephalopathy (PML), which is a demyelinating disease of the central nervous system caused by reactivation of a latent papovavirus (the JC polyomavirus)

infection, that can cross the BBB. Some aspects of the invention relate to a method for delivering therapeutic nanoparticles of the present invention incorporating anti-virus (such as papovarus) drugs as a bioactive agent to the tight junction of a brain-blood barrier site for treatment of PML.

One disease associated with brain-blood barrier is HIV Encephalitis. It is believed that HIV can cross the blood-brain barrier inside circulating monocytes in the bloodstream ("Trojan horse theory"). Once inside, these monocytes become activated and are transformed into macrophages. Activated monocytes release virions into the brain tissue proximate to brain microvessels. These viral particles likely attract the attention of sentinel brain microglia and initiate an inflammatory cascade that may cause tissue damage to the BBB. This inflammation is HIV encephalitis (HIVE). Instances of HIVE probably occur throughout the course of AIDS and is a precursor for HIV-associated dementia (HAD). Some aspects of the invention relate to a method for delivering therapeutic nanoparticles of the present invention incorporating anti-HIV drugs or anti-inflammatory medicine as a bioactive agent to the tight junction of a brain-blood barrier site for treatment of HIV.

Among all diseases associated with blood-brain barrier, the most critical is Alzheimer's Disease (AD). New evidence indicates that disruption of the blood-brain barrier in AD patients allows blood plasma containing amyloid beta (Aβ) to enter the brain where the Aβ adheres preferentially to the surface of astrocytes. These findings have led to the hypotheses that (i) breakdown of the blood-brain barrier allows access of neuron-binding autoantibodies and soluble exogenous Aβ42 to brain neurons and (ii) binding of these autoantibodies to neurons triggers and/or facilitates the internalization and accumulation of cell surface-bound Aβ42 in vulnerable neurons through their natural tendency to clear surface-bound autoantibodies via endocytosis. Eventually the astrocyte is overwhelmed, dies, ruptures, and disintegrates, leaving behind the insoluble Aβ42 plaque. Thus, in some patients, Alzheimer's disease may be caused (or more likely, aggravated) by a breakdown in the blood-brain barrier. Some aspects of the invention relate to a method for delivering therapeutic nanoparticles of the present invention incorporating anti-Alzheimer's drugs (i.e., Alzheimer's antagonist) or anti-inflammatory medicine as a bioactive agent to the tight junction of a brain-blood barrier site for treatment of AD. In one embodiment, the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, and tacrine hydrochloride.

Example No. 24

Bioactive Nanoparticles Delivery Through Tight Junctions

One possible route of a drug administered by the nasal pathway is to enter the olfactory mucosa, followed by entering the brain tissue via cerebrospinal fluid (CSF). The mammalian nasal cavity is lined with three types of epithelia: squamous, respiratory and olfactory. The main part of the nasal cavity is covered by a typical airway epithelium. CSF is secreted at the four choroids plexi, located in the lateral and third and fourth ventricles. CSF is an isotonic aqueous solution with the concentrations of the major solutes practically identical to those found in the plasma, except for $K^+$ and $Ca^{2+}$. Paracellular passage, followed by transport through the olfactory perineural space, that may be continuous with a subarachnoid extension that surrounds the olfactory nerve as it penetrates the cribriform plate, has been suggested (Arch Otolaryngology 1985; 105:180-184). Therefore, substances may enter the brain after paracellular passage by flushing with CSF re-entering again into the brain extracellular space at the cribriform plate.

The olfactory system is unique because the primary neurons of the olfactory pathway project directly to the cerebral cortex. Consequently, the olfactory epithelium allows the influx of some drugs into the olfactory bulb using axonal transport, and further movement into the central nervous system. The entry of drugs into the olfactory bulb is also possible probably by direct diffusion into the surrounding CSF. The distribution of drugs from the nasal membrane into the CSF appears to be controlled by a combination of their molecular properties. For protein or peptides, the controlling mechanism involves the tight junctions of epithelia at the outer layer of the olfactory bulbs. The chitosan-shelled bioactive nanoparticles or fragments of the present invention possess the molecular properties of enhanced permeating through the tight junctions as described above. It is generally accepted that the nasal route circumvents the first-pass liver metabolism and elimination associated with oral drug delivery. Some aspects of the invention relate to a method of delivering a bioactive agent into CSF comprising providing bioactive nanoparticles or fragments intranasally, wherein the bioactive nanoparticles or fragments comprise a shell substrate composed mostly of chitosan, a core substrate that comprises the bioactive agent and a negatively charged substrate that is at least partially neutralized with a portion of the positively charged chitosan in the core portion.

Example No. 25

Nanoparticles with Enhanced Nasal Absorption

In contrast to oral administration, nasally administered drugs are only transported over a very short distance, remain only about 15 minutes in the nasal cavity and are not exposed to low pH value and degrading enzymes. Fernandez-Urrusuno et al. reported enhanced nasal absorption of insulin using chitosan/TPP/insulin nanoparticles (Pharmaceutical Research 1999; 16:1576-1581), with a mean particle size in the range of 300 nm to 400 nm and a positive zeta potential (from +54 mV to +25 mV). The chitosan/TPP/insulin nanoparticles have demonstrated its effect on glucose reduction in animals by nasal instillation. The chitosan/TPP/insulin nanoparticles as reported have shown intensified contact of insulin with the absorptive epithelium as compared to chitosan solution. It was suggested that the chitosan/TPP/insulin nanoparticles cross the nasal epithelium, thus working as peptide carriers to the systemic circulation.

In one embodiment, the nanoparticles of the present invention may be administered to humans and other animals for therapy by any suitable route of administrations including orally, nasally, as by, for example, a spray, parenterally, and topically, as by powders or drops, including orally, buccally and sublingually. Nasal sprays can be used for transmucosal administration. Some aspects of the invention relate to a nanoparticle system consisting of chitosan (or chitosan derivative, such as TMC and the like), PGA (γ-PGA, α-PGA, derivatives or salts of PGA, and the like) and at least one bioactive agent and a method of delivering the above-mentioned nanoparticle system or chitosan-shelled nanoparticulate fragments via intranasal, oral, buccal or sublingual administration into the systemic circulation. In one preferred embodiment, the systemic circulation herein is for delivering the at least one bioactive to brain via chitosan-shelled nanoparticles or chitosan-shelled nanoparticulate fragments of the present invention. The bioactive nanoparticle fragments herein are generally in the range of about 10 to 150 nm, preferably in the range of about 20 to 100 nm, and most preferably in the range of about 20 to 50 nm.

Example No. 26

Bioactive Nanoparticles Delivery Through Systemic Blood Circulation

The mean pH in the body fluid in intercellular spaces between enterocytes is about 7.4. Epithelia or endothelia constitute the structural basis of the blood-tissue barriers such as the blood-brain, blood-nerve, blood-retina, blood aqueous and placental barriers. Tight junctions connecting the epithelial or endothelial cells or syncytial cell layers prevent the free exchange of substances between the blood and the compartments guarded by the barrier, and only limited substances are allowed to pass through it. Many researchers have reported unique connection between the nose and the brain and intranasal delivery of drugs to the brain bypassing the blood-brain barrier (Eur J Pharm Sci 2000; 11:1-18; Neuroscience 2004; 127:481-496).

The nasal epithelium displays a relatively high permeability to drugs, due to the presence of a dense blood vessel network. The advantages of this route of administration are also a rapid absorption and onset of the pharmacological response, avoidance of hepatic first-pass metabolism, high systemic availability and an easy administration route suitable for self-medication. Recently several studies have indicated that hydrophilic or relatively large molecules such as proteins, viruses or dextrans with a molecular weight up to 20 KDa can be directly transported from the nasal cavity to the CSF using neuronal anterograde and retrograde transport, and that the transport of large molecules to the CSF is dependent on their molecular weights. Thus a drug administered by the nasal route may enter either the blood of the general circulation and into CSF via choroids plexus blood-brain barrier into the brain as described above.

The respiratory epithelium is a pseudostratified, columnar epithelium with an abundance of secretory cells lying on a basement membrane. It is considered the main site for drug absorption into the systemic circulation. Intranasally delivered drugs show a rapid rise to peak blood concentrations, due to a high permeability of the nasal epithelia for relatively large molecules and to the presence of an important microvasculature. As relatively large, water-soluble peptides possess a significant nasal bioavailability, it has been suggested that the transepithelial pathway for these peptides is paracellular, i.e., through intercellular junctional zones (Eur J Pharm Sci 2001; 14:69-74). Absorption enhancers are frequently used to obtain higher bioavailability of a drug with limited nasal absorption. Some aspects of the invention relate to bioactive nanoparticles or fragments with chitosan (an absorption enhancer) dominated at the surface, showing a positive surface charge.

Chitosan-based transport system was reported for overcoming the blood-brain barrier. Several examples illustrate intravenous administration of a mixture of chain-like chitosan to which a peptide was bound for treating tumor diseases or other indications in the brain. The experimental data cited in this publication indicate that the drug absorption in the neuronal cells can be proven by studies in mice that had the transport system containing chain-like chitosan. Some aspects of the present invention provide a method of delivering a bioactive agent to CSF comprising providing bioactive nanoparticles or fragments intranasally, wherein the bioactive nanoparticles or fragments comprise a shell substrate of mostly chitosan, a core substrate that comprises PGA and the bioactive agent. In one embodiment, the bioactive nanoparticles or fragments enters a blood vessel between the nasal cavity and the CSF with a relatively short systemic circulation, as compared to a long systemic circulation via conventional intravenous injection.

In one embodiment of the present invention, the bioactive agent is associated with or entrapped within micelles before being loaded into the nanoparticle structure. In another embodiment, the bioactive agent is lipophilic or hydrophobic (i.e., non-hydrophilic), such as Omega-3, Omega-6, Omega-9, shark liver oil, and the like. After being associated with micelles (via a physical, chemical, or a biochemical means), the lipophilic or hydrophobic bioactive agent becomes encapsulatable through the affinity of micelles toward the inactive ingredients of chitosan and a negative charged substrate of the nanoparticles. Lipophilicity refers to the ability of a chemical compound to dissolve in fats, oils, lipids, and non-polar solvents such as hexane or toluene. These non-polar solvents are themselves lipophilic—the axiom that like dissolves like generally holds true. Thus, lipophilic substances tend to dissolve in other lipophilic substances, while hydrophilic (water-loving) substances tend to dissolve in water and other hydrophilic substances.

Lipophilicity, hydrophobicity, and non-polarity are often used interchangeably. However, the terms "lipophilic" and "hydrophobic" are not synonymous. Lipophilic substances interact within themselves and with other substances through the London dispersion force. They have little to no capacity to form hydrogen bonds. When a molecule of a lipophilic substance is enveloped by water, surrounding water molecules enter into an 'ice-like' structure over the greater part of its molecular surface, the thermodynamically unfavorable event that drives oily substances out of water. Thus, lipophilic substances tend to be water insoluble.

Example No. 27

Nanoparticles Having Bioactive Agents Associated with Micelles

Some aspects of the invention relate to bioactive nanoparticles for enhancing the permeation of at least one bioactive agent, the nanoparticles or collapsed nanoparticles (or fragments thereof as defined herein comprising a portion of collapsed nanoparticles with associated portion of the at least one bioactive agent) comprising a shell portion that is dominated by positively charged chitosan, a core portion that contains negatively charged substrate, wherein the negatively charged substrate is at least partially neutralized and/or reacted with a portion of the positively charged chitosan in the core portion, and the at least one bioactive agent loaded within the nanoparticles. In one embodiment, the at least one bioactive agent is hydrophobic or lipophilic, which is associated in micelles or loaded within micelles before being encapsulated in nanoparticles. In one embodiment, the micelles are made via an emulsion process, an oil-in-water microemulsion process or self-emulsifying formulation. In another embodiment, the self-emulsifying micelle system is a mixture of oil, surfactant, co-surfactant and lipophilic or hydrophobic drugs. In one embodiment, the resulting nanoparticle with substantial CS-γ-PGA uniform network across the shell portion and the core portion enables more compact nanoparticle framework and higher API loading.

Example No. 28

Micelles in Bioactive Nanoparticles

Figure 20:
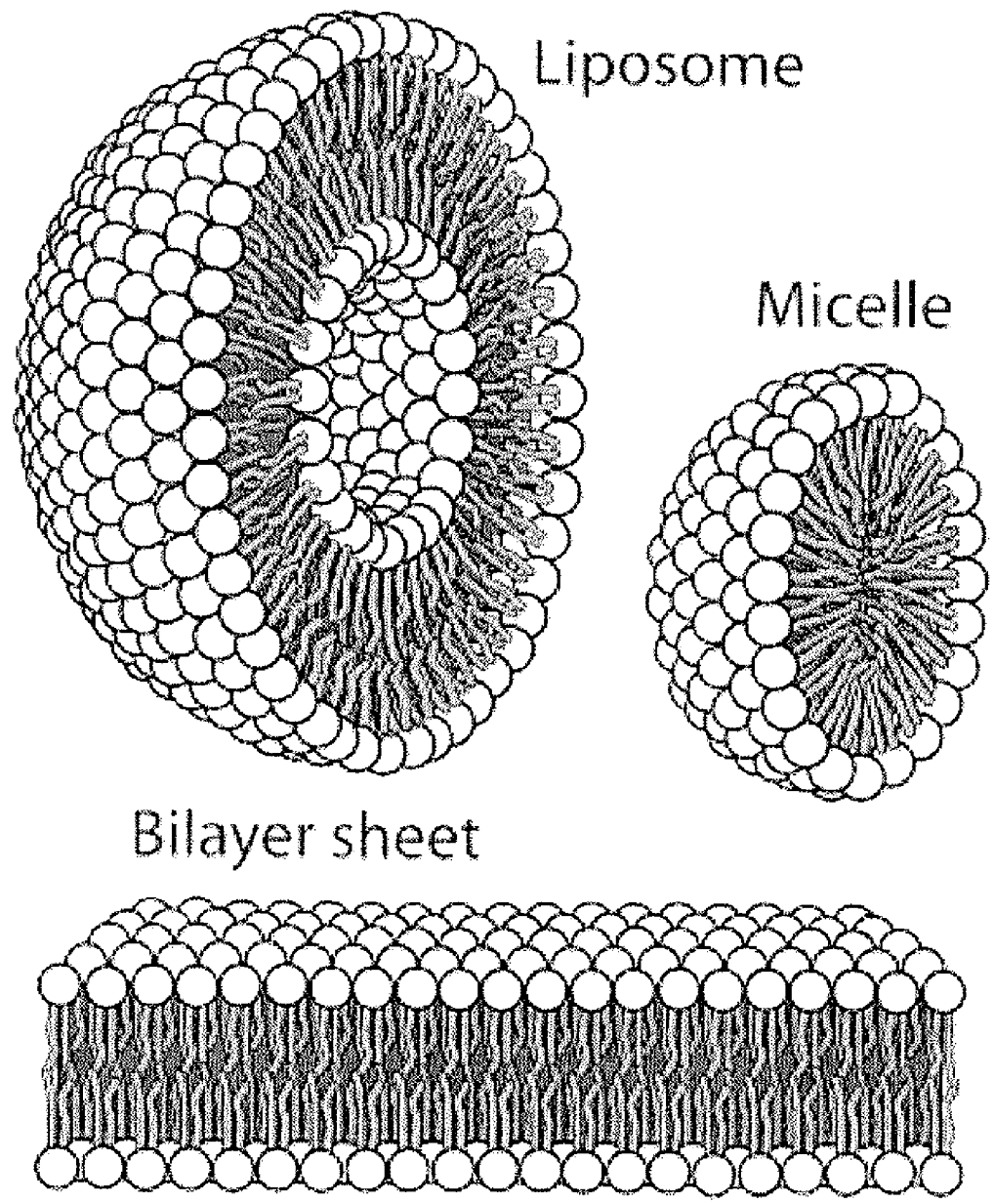
FIG. 20 shows cross-section of the different structures that phospholipids can take in an aqueous solution. The circles are the hydrophilic heads and the wavy lines are the fatty acyl side chains.

A micelle is an aggregate of surfactant molecules dispersed in a liquid colloid. A typical micelle in aqueous solution forms an aggregate with the hydrophilic "head" regions in contact with surrounding solvent, sequestering the hydrophobic single tail regions in the micelle centre (see FIG. 20). This phase is caused by the insufficient packing issues of single tailed lipids in a bilayer. The difficulty filling all the volume of the interior of a bilayer, while accommodating the area per head group forced on the molecule by the hydration of the lipid head group leads to the formation of the micelle. This type of micelle is known as a normal phase micelle (oil-in-water micelle). Inverse micelles have the headgroups at the centre with the tails extending out (water-in-oil micelle). Micelles are approximately spherical in shape. Other phases, including shapes such as ellipsoids, cylinders, and bilayers are also possible. The shape and size (typically a few nanometers) of a micelle is a function of the molecular geometry of its surfactant molecules and solution conditions such as surfactant concentration, temperature, pH, and ionic strength. The process of forming micelles is known as micellization and forms part of the phase behavior of many lipids according to their polymorphism.

The ability of a soapy solution to act as a detergent has been recognized for centuries. The existence of "colloidal ions" or the highly mobile, spontaneously formed clusters came to be called micelles. Individual surfactant molecules that are in the system but are not part of a micelle are called "monomers." Lipid micelles represent a molecular assembly in which the individual components are thermodynamically in equilibrium with monomers of the same species in the surrounding medium. In water, the hydrophilic "heads" of surfactant molecules are always in contact with the solvent, regardless of whether the surfactants exist as monomers or as part of a micelle. However, the lipophilic "tails" of surfactant molecules have less contact with water when they are part of a micelle—this being the basis for the energetic drive for micelle formation. In a micelle, the hydrophobic tails of several surfactant molecules assemble into an oil-like core the most stable form of which has no contact with water. By contrast, surfactant monomers are surrounded by water molecules that create a "cage" of molecules connected by hydrogen bonds. This water cage is similar to a clathrate and has an ice-like crystal structure and can be characterized according to the hydrophobic effect. The extent of lipid solubility is determined by the unfavorable entropy contribution due to the ordering of the water structure according to the hydrophobic effect.

Micelles composed of ionic surfactants have an electrostatic attraction to the ions that surround them in solution, the latter known as counterions. Although the closest counterions partially mask a charged micelle (by up to 90%), the effects of micelle charge affect the structure of the surrounding solvent at appreciable distances from the micelle. Ionic micelles influence many properties of the mixture, including its electrical conductivity. Adding salts to a colloid containing micelles can decrease the strength of electrostatic interactions and lead to the formation of larger ionic micelles. This is more accurately seen from the point of view of an effective change in hydration of the system.

Micelles only form when the concentration of surfactant is greater than the critical micelle concentration (CMC), and the temperature of the system is greater than the critical micelle temperature, or Kraft temperature. The formation of micelles can be understood using thermodynamics: micelles can form spontaneously because of a balance between entropy and enthalpy. In water, the hydrophobic effect is the driving force for micelle formation, despite the fact that assembling surfactant molecules together reduces their entropy. At very low concentrations of the lipid, only monomers are present in true solution. As the concentration of the lipid is increased, a point is reached at which the unfavorable entropy considerations, derived from the hydrophobic end of the molecule, become dominant. At this point, the lipid hydrocarbon chains of a portion of the lipids must be sequestered away from the water. Therefore, the lipid starts to form micelles. Broadly speaking, above the CMC, the entropic penalty of assembling the surfactant molecules is less than the entropic penalty of caging the surfactant monomers with water molecules. Also important are enthalpy considerations, such as the electrostatic interactions that occur between the charged parts surfactants.

In a non-polar solvent, it is the exposure of the hydrophilic head groups to the surrounding solvent that is energetically unfavorable, giving rise to a water-in-oil system. In this case, the hydrophilic groups are sequestered in the micelle core and the hydrophobic groups extend away from the centre. These inverse micelles are proportionally less likely to form on increasing headgroup charge, since hydrophilic sequestration would create highly unfavorable electrostatic interactions.

When surfactants are present above the CMC, they can act as emulsifiers that will allow a compound that is normally insoluble (in the solvent being used) to dissolve. This occurs because the insoluble species can be incorporated into the micelle core, which is itself solubilized in the bulk solvent by virtue of the head groups' favorable interactions with solvent species. The most common example of this phenomenon is detergents, which clean poorly soluble lipophilic material (such as oils and waxes) that cannot be removed by water alone. Detergents also clean by lowering the surface tension of water, making it easier to remove material from a surface. The emulsifying property of surfactants is also the basis for emulsion polymerization.

Figure 17:
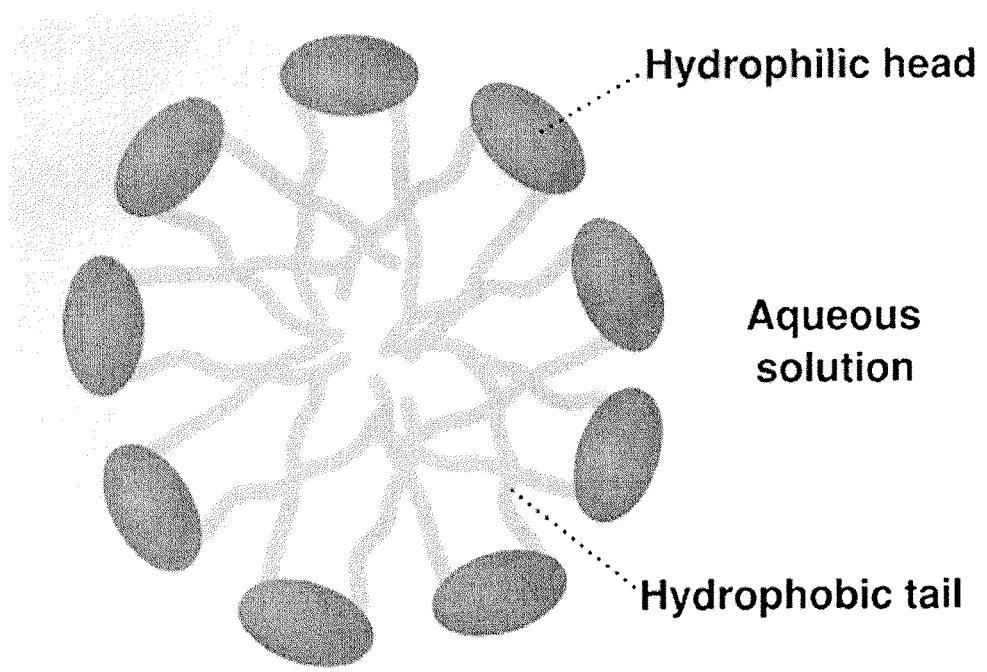
FIG. 17 shows scheme of a micelle formed by phospholipids in an aqueous solution.
Figure 18:
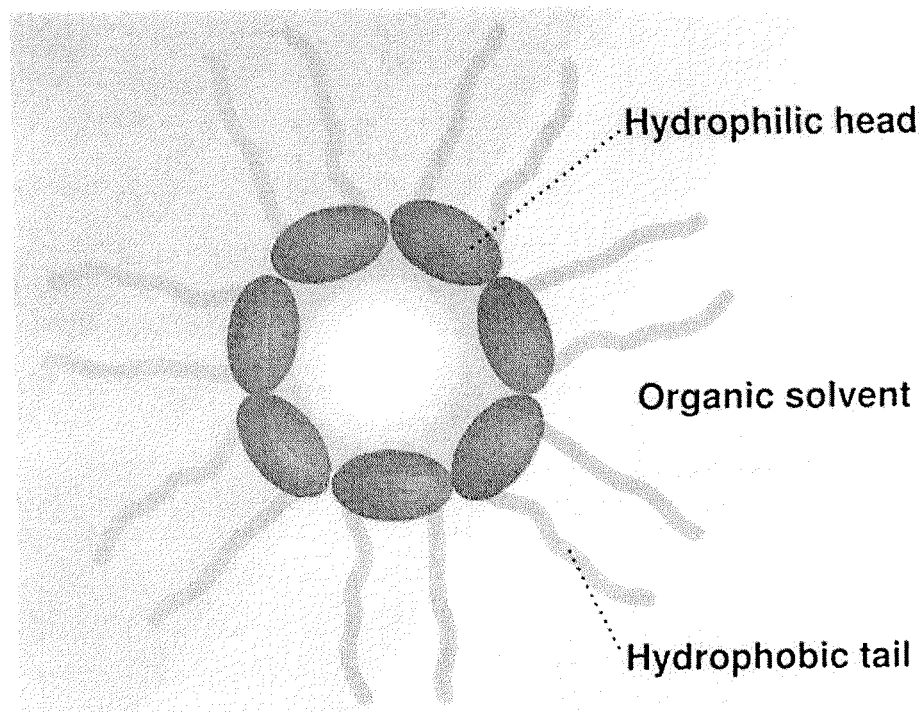
FIG. 18 shows scheme of a micelle formed by phospholipids in an organic solvent.

Micelle formation is essential for the absorption of fat-soluble vitamins and complicated lipids within the human body. Bile salts formed in the liver and secreted by the gall bladder allow micelles of fatty acids to form. This allows the absorption of complicated lipids (e.g., lecithin) and lipid soluble vitamins (A, D, E and K) within the micelle by the small intestine. FIG. 17 shows scheme of a micelle formed by phospholipids in an aqueous solution, whereas FIG. 18 shows scheme of a micelle formed by phospholipids in an organic solvent. In one embodiment, either scheme of micelles may be feasible to be encapsulated in a nanoparticle formulation as disclosed in the present invention.

Example No. 29

Emulsifying Process for Micelles Formation

An emulsion is a mixture of two or more immiscible (unblendable) liquids. One liquid (the dispersed phase) is dispersed in the other (the continuous phase). Many emulsions are oil/water emulsions, with dietary fats being one common type of oil encountered in everyday life. Examples of emulsions include butter and margarine, milk and cream, and vinaigrettes; the photo-sensitive side of photographic film, magmas and cutting fluid for metal working. In butter and margarine, fat surrounds droplets of water (a water-in-oil emulsion). In milk and cream, water surrounds droplets of fat (an oil-in-water emulsion). In certain types of magma, globules of liquid NiFe may be dispersed within a continuous phase of liquid silicates. Emulsification is the process by which emulsions are prepared.

Emulsions are thermodynamically unstable liquid/liquid dispersions that are stabilized, in general, by surfactants. Surfactants are usually added to emulsion systems, assembling in the interface of the emulsion droplets, thus providing a protective membrane that prevents the droplets from flocculating or coalescing and thus enhancing the droplets formation and stability. Emulsion dispersion is not about reactor blends for which one polymer is polymerized from its monomer in the presence of the other polymers; emulsion dispersion is a novel method of choice for the preparation of homogeneous blends of thermoplastic and elastomer. In emulsion dispersion system the preparation of well-fined polymers droplets maybe acquired by the use of water as dispersing medium. The surfactant molecules adsorb on the surface of emulsion by creating a dispersion of droplets, which reduces interfacial tension and retards particle flocculation during mixing. The molecules of surfactant have polar and non-polar parts which act as an intermediary to combine polar and non-polar polymers; the intermolecular interactions between the polar and the non-polar polymer segments resemble the macroscopic hydrocarbon-water interface.

Emulsions tend to have a cloudy appearance, because the many phase interfaces (the boundary between the phases is called the interface) scatter light that passes through the emulsion. Emulsions are unstable and thus do not form spontaneously. Energy input through shaking, stirring, homogenizing, or spray processes are needed to form an emulsion. Over time, emulsions tend to revert to the stable state of the phases comprising the emulsion. Surface-active substances (surfactants) can increase the kinetic stability of emulsions greatly so that, once formed, the emulsion does not change significantly over years of storage. Vinaigrette is an example of an unstable emulsion that will quickly separate unless shaken continuously. This phenomenon is called coalescence, and happens when small droplets recombine to form bigger ones.

Emulsions are part of a more general class of two-phase systems of matter called colloids. Although the terms colloid and emulsion are sometimes used interchangeably, emulsion tends to imply that both the dispersed and the continuous phase are liquid. There are three types of emulsion instability: flocculation, where the particles form clumps; creaming, where the particles concentrate towards the surface (or bottom, depending on the relative density of the two phases) of the mixture while staying separated; and breaking and coalescence where the particles coalesce and form a layer of liquid. Whether an emulsion turns into a water-in-oil emulsion or an oil-in-water emulsion depends on the volume fraction of both phases and on the type of emulsifier. Generally, the Bancroft rule applies: emulsifiers and emulsifying particles tend to promote dispersion of the phase in which they do not dissolve very well; for example, proteins dissolve better in water than in oil and so tend to form oil-in-water emulsions (that is they promote the dispersion of oil droplets throughout a continuous phase of water).

The basic color of emulsions is white. If the emulsion is dilute, the Tyndall effect will scatter the light and distort the color to blue; if it is concentrated, the color will be distorted towards yellow. This phenomenon is easily observable on comparing skimmed milk (with no or little fat) to cream (high concentration of milk fat). Microemulsions and nanoemulsions tend to appear clear due to the small size of the disperse phase.

An emulsifier (also known as an emulgent) is a substance that stabilizes an emulsion, frequently a surfactant. Examples of food emulsifiers are egg yolk (where the main emulsifying chemical is lecithin), honey, and mustard, where a variety of chemicals in the mucilage surrounding the seed hull act as emulsifiers; proteins and low-molecular weight emulsifiers are common as well. In some cases, particles can stabilize emulsions as well through a mechanism called Pickering stabilization. Both mayonnaise and Hollandaise sauce are oil-in-water emulsions that are stabilized with egg yolk lecithin. Detergents are another class of surfactant, and will physically interact with both oil and water, thus stabilizing the interface between oil or water droplets in suspension. This principle is exploited in soap to remove grease for the purpose of cleaning. A wide variety of emulsifiers are used in pharmacy to prepare emulsions such as creams and lotions. Common examples include emulsifying wax, cetearyl alcohol, polysorbate 20, and cetearth 20.

Sometimes the inner phase itself can act as an emulsifier, and the result is nanoemulsion—the inner state disperses into nano-size droplets within the outer phase. A well-known example of this phenomenon, the ouzo effect, happens when water is poured in a strong alcoholic anise-based beverage, such as ouzo, pastis, arak or raki. The anisolic compounds, which are soluble in ethanol, now form nano-sized droplets and emulgate within the water. The color of such diluted drink is opaque and milky.

Microemulsions are clear, stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o). In ternary systems such as microemulsions, where two immiscible phases (water and 'oil') are present with a surfactant, the surfactant molecules may form a monolayer at the interface between the oil and water, with the hydrophobic tails of the surfactant molecules dissolved in the oil phase and the hydrophilic head groups in the aqueous phase. As in the binary systems (water/surfactant or oil/surfactant), self-assembled structures of different types can be formed, ranging, for example, from (inverted) spherical and cylindrical micelles to lamellar phases and discontinuous microemulsions, which may coexist with predominantly oil or aqueous phases.

The microemulsion region is usually characterized by constructing ternary-phase diagrams. Three components are the basic requirement to form a microemulsion: an oil phase, an aqueous phase and a surfactant. If a cosurfactant is used, it may sometimes be represented at a fixed ratio to surfactant as a single component, and treated as a single "pseudo-component". The relative amounts of these three components can be represented in a ternary phase diagram. Gibbs phase diagrams can be used to show the influence of changes in the volume fractions of the different phases on the phase behavior of the system. The three components composing the system are each found at an apex of the triangle, where their corresponding volume fraction is 100%. Moving away from that corner reduces the volume fraction of that specific component and increases the volume fraction of one or both of the two other components. Each point within the triangle represents a possible composition of a mixture of the three components or pseudo-components, which may consist (ideally, according to the Gibbs' phase rule) of one, two or three phases. These points combine to form regions with boundaries between them, which represent the "phase behavior" of the system at constant temperature and pressure.

Some aspects of the invention provide a formulation of micelles and methods of formulating micelles, the micelles comprising a basic structure as described above and at least one hydrophobic or lipophilic bioactive agent enclosed within (called 'bioactive micelles'). One aspect of the invention further provides a pharmaceutical composition of nanoparticles, the nanoparticles comprising a shell portion that is dominated by positively charged chitosan, a core portion that comprises one negatively charged substrate, wherein the negatively charged substrate is at least partially neutralized with a portion of the positively charged chitosan in the core portion, and micelles, wherein at least one bioactive agent is loaded within the micelles. The micelles are less than about 100 nanometers, preferably less than about 20 nanometers, and most preferably less than about 10 nanometers.

Example No. 30

Chitosan/DNA Complexes Coated by Anionic Compound

In a non-viral carrier for gene delivery, a particle complex (or particulate complex) system comprised of the core CS/DNA complex and the outer coating of an anionic polymer, for example poly(γ-glutamic acid) (γ-PGA) makes the particulate complex more compact because γ-PGA was entangled tightly with the excess CS emanating from the surface of core CS/DNA complexes (also known as test complexes). In one embodiment, the particulate complex is in a nanoparticle or nanoparticle-like configuration. In another embodiment, the core CS/DNA complex is manufactured via a simple and mild ionic gelation method similar to the method as disclosed in Example No. 4, wherein CS is a cationic amine-containing polysaccharide and DNA is a negatively-charged substrate. In one embodiment, the particulate complexes have a mean particle size between about 50 and 400 nanometers.

Some aspects of the invention relate to a method of manufacturing a bioactive agent-containing particulate complex comprising the steps of (a) forming the core complex by mixing the positively charged chitosan and a first negatively charged substrate in a gelation process, including the bioactive agent; (b) coating a second negatively charged substrate onto the surface of the core complex to form the particulate complex suspension in solution, and (c) separate the bioactive agent-containing particulate complexes from the solution. In one embodiment, the bioactive agent is DNA, whereas DNA is a negatively charged substrate. In another embodiment, the first or second negatively charged substrate is γ-PGA, which is selected from the group consisting of γ-PGA, α-PGA, PGA derivatives, PGA-DTPA, acetylated γ-PGA and salts of PGA. In another exemplary embodiment, the particulate complex is CS/DNA/γ-PGA complex. γ-PGA can be in different conformational states, including α-helix, β-sheet, random coil, helix-coil transition and enveloped aggregation. In DI water (pH 6.0), γ-PGA molecules are mainly in the form of linear random-coil conformation and show a polyanionic characteristic, allowing themselves to entangle tightly with the excess CS emanating from the surface of the core complex, thus making the particulate complex more compact. In one embodiment, the particulate complexes are treated with an enteric polymer.

FIG. 23 shows the particle size and zeta potential of the particulate complexes in aqueous media, where the core complexes coated with γ-PGA had a smaller particle size than their counterpart (core complex in the absence of γ-PGA coating). It was evident that γ-PGA coating significantly reduced their surface charge. With increasing the coating of γ-PGA, the zeta potential of the particulate complexes decreased appreciably and reached its minimum value (approximately −27 mV) at an (N/P)/C ratio of (10/1)/12. Further increasing the amount of γ-PGA onto the core complex did not significantly alter the surface charge of the particulate complexes, as shown in the cases of (N/P)/C ratios of (10/1)/20 and (10/1)/40. In one embodiment as shown in FIG. 23, the surface zeta potential of the particulate complexes may be positive, neutral, or negative values.

With γ-PGA coating on core CS/DNA complex, the extent of complexes internalization and their transfection efficiency were evidently enhanced. The endocytosis inhibition study indicates that the γ-glutamyl transpeptidase (GGT) present on cell membranes was responsible for the uptake of core complexes. In one embodiment, when entangled with CS, the free N-terminal γ-glutamyl unit of γ-PGA on complexes was exposed and thus be accommodated within the γ-glutamyl binding pocket of the membrane GGT. After internalization of the particulate complex, as both γ-PGA and DNA in the complexes carried negative charges, the electrostatic repulsion between the two might lead to the disintegration of the complexes. Such a structure disruption may facilitate the intracellular release of DNA, thus augmenting their transfection efficiency.

Some aspects of the invention relate to CS/DNA/γ-PGA particulate complexes that significantly enhance the cellular uptake of complexes, consequently augmenting their gene expressing level. Some aspects of the invention relate to a composition of particulate complexes, the complexes consisting of a core portion of positively charged chitosan, a first negatively charged substrate, optionally a zero-charge compound and one bioactive agent, and an outer portion of a second negatively charged substrate wherein the particulate complexes have a mean complex size between about 50 and 400 nanometers. In one embodiment, the first negatively charged substrate is DNA, RNA, a small interfering ribonucleic acid (siRNA), or the like. In one embodiment, the bioactive agent is selected from the group consisting of hormone, growth hormone, and human growth hormone. In one embodiment, the core portion further comprises micelles, wherein the micelles are oil-in-water micelles, water-in-oil micelles, or hybrid micelles.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of delivering at least one bioactive agent to an animal subject with enhanced cellular uptake of said at least one bioactive agent by said subject, the method comprising: (a) loading said bioactive agent in particulate complexes, wherein the particulate complexes comprise a core portion of positively charged chitosan, an outer portion of a negatively charged substrate, optionally a zero-charge compound, and said bioactive agent loaded in the core portion, wherein said particulate complexes have a mean complex size between about 50 and 400 nanometers; and (b) delivering said particulate complexes via a parenteral route to said animal subject.

2. The method of claim 1, wherein said chitosan is N-trimethyl chitosan, mono-N-carboxymethyl chitosan (MCC), N-palmitoyl chitosan (NPCS), EDTA-chitosan, low molecular weight chitosan, chitosan derivatives, or combinations thereof.

3. The method of claim 1, wherein said at least one bioactive agent is DNA, RNA, or a small interfering ribonucleic acid (siRNA).

4. The method of claim 1, wherein said core portion further comprises micelles.

5. The method of claim 4, wherein the micelles are oil-in-water micelles, water-in-oil micelles, or hybrid micelles.

6. The method of claim 1, wherein said negatively charged substrate is selected from the group consisting of γ-PGA, α-PGA, PGA-complexone conjugate, water-soluble salts of PGA, metal salts of PGA, and glycosaminoglycans.

7. The method of claim 1, wherein said particulate complexes are freeze-dried, thereby said particulate complexes being in a powder form.

8. The method of claim 1, wherein said particulate complexes are mixed with trehalose and then freeze-dried, thereby said particulate complexes being in a powder form.

9. The method of claim 1, wherein said particulate complexes are treated with an enteric polymer.

10. The method of claim 1, wherein said bioactive agent is selected from the group consisting of proteins, peptides, nucleosides, nucleotides, antiviral agents, antineoplastic agents, antibiotics, and anti-inflammatory drugs.

11. The method of claim 1, wherein said bioactive agent is an agent for treating Alzheimer's disease selected from the group consisting of memantine hydrochloride, donepezil hydrochloride, rivastigmine tartrate, galantamine hydrochloride, insulin, and tacrine hydrochloride.

12. The method of claim 1, wherein said bioactive agent is selected from the group consisting of anti-epileptic drugs, anti-HIV drugs, anti-oxidants, anti-neuromyelitis optica drugs, meningitis antagonist, and anti-multiple sclerosis drugs.

13. The method of claim 1, wherein said bioactive agent is an anti-diabetic compound.

14. The method of claim 1, wherein said one bioactive agent is heparin or low molecular weight heparin.

15. The method of claim 1, wherein said bioactive agent is selected from the group consisting of hormone growth hormone, and human growth hormone.

16. The method of claim 1, wherein said bioactive agent is selected from the group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor, anti tumor necrosis factor, erythropoietin, and melanocyte-stimulating hormone.

17. The method of claim 1, wherein said particulate complexes are manufactured via a simple and mild ionic gelation method.

18. The method of claim 1, wherein said cellular uptake is via an endocytosis method.

19. The method of claim 1, wherein said bioactive agent is a gene.

20. The method of claim 1, wherein a surface zeta potential of the particulate complexes is with a positive, neutral, or negative value.

* * * * *